US010940150B2

(12) United States Patent
Schroeder et al.

(10) Patent No.: US 10,940,150 B2
(45) Date of Patent: Mar. 9, 2021

(54) THYMINE DERIVATIVES AND QUINAZOLINE-DIONE DERIVATIVES FOR THE INHIBITION OF HSP27

(71) Applicant: TECHNISCHE UNIVERSITAET DRESDEN, Dresden (DE)

(72) Inventors: Michael Schroeder, Dresden (DE); Yixin Zhang, Dresden (DE); Joerg-Christian Heinrich, Dresden (DE); Joachim Haupt, Bobritzsch-Hilbersdorf (DE); Sainitin Donakonda, Andhra Pradesh (IN); Petra Lennig, Dresden (DE)

(73) Assignee: Technische Universitaet Dresden, Dresden (DE)

( * ) Notice: Subject to any disclaimer, the term of this patent is extended or adjusted under 35 U.S.C. 154(b) by 3 days.

(21) Appl. No.: 15/329,722

(22) PCT Filed: Jul. 28, 2015

(86) PCT No.: PCT/EP2015/067312
§ 371 (c)(1),
(2) Date: Jan. 27, 2017

(87) PCT Pub. No.: WO2016/016268
PCT Pub. Date: Feb. 4, 2015

(65) Prior Publication Data
US 2018/0207160 A1    Jul. 26, 2018

(30) Foreign Application Priority Data

Jul. 28, 2014    (DE) .................... 10 2014 214 798.0
Jul. 28, 2014    (DE) .................... 10 2014 214 799.9

(51) Int. Cl.
| A61K 31/513 | (2006.01) |
| A61K 31/5415 | (2006.01) |
| A61P 35/00 | (2006.01) |
| A61K 45/06 | (2006.01) |
| A61K 31/708 | (2006.01) |
| A61K 31/522 | (2006.01) |

(52) U.S. Cl.
CPC .......... *A61K 31/513* (2013.01); *A61K 31/522* (2013.01); *A61K 31/5415* (2013.01); *A61K 31/708* (2013.01); *A61K 45/06* (2013.01); *A61P 35/00* (2018.01)

(58) Field of Classification Search
None
See application file for complete search history.

(56) References Cited

U.S. PATENT DOCUMENTS

| 5,116,823 | A | * | 5/1992 | Calabresi | A61K 31/505 |
| | | | | | 514/274 |
| 6,525,032 | B2 | | 2/2003 | Mantell et al. | |
| 6,995,145 | B1 | * | 2/2006 | Au | A61K 31/70 |
| | | | | | 514/42 |
| 7,977,343 | B2 | | 7/2011 | Buchstaller et al. | |
| 8,617,823 | B2 | | 12/2013 | Rubin-Bejerano et al. | |
| 2001/0020089 | A1 | | 9/2001 | Mantell et al. | |
| 2005/0137185 | A1 | | 6/2005 | Lee et al. | |
| 2007/0275986 | A1 | | 11/2007 | Becq et al. | |
| 2010/0160352 | A1 | | 6/2010 | Buchstaller et al. | |
| 2011/0070192 | A1 | | 3/2011 | Tse et al. | |
| 2011/0166096 | A1 | | 7/2011 | Fahrig et al. | |
| 2012/0195911 | A1 | | 8/2012 | Martynov et al. | |
| 2012/0294846 | A1 | | 11/2012 | Bonniaud et al. | |
| 2013/0150429 | A1 | | 6/2013 | Gleave et al. | |
| 2014/0057864 | A1 | | 2/2014 | Kim | |

FOREIGN PATENT DOCUMENTS

| CN | 1878556 | 12/2006 |
| CN | 103443085 | 12/2013 |
| DE | 601 19 492 T2 | 11/2006 |
| DE | 10 2005 037 733 | 2/2007 |
| DE | 10 2008 035 299 | 2/2010 |
| JP | 2010-215669 | 9/2010 |
| WO | 01/72779 | 10/2001 |
| WO | 2006/120481 | 11/2006 |
| WO | 2007/034185 | 3/2007 |
| WO | 2008/146008 | 12/2008 |
| WO | 2009/156182 | 12/2009 |
| WO | 2012/125521 | 9/2012 |
| WO | 2012/130166 | 10/2012 |

(Continued)

OTHER PUBLICATIONS

Hernandez et al. Journal of Bioorganic and Medicinal Chemistry Letters, 13, 3027-3030 (2003) (Year: 2003).*
Hernandez et al. in Journal of Medicinal Chemistry 45, 4254-4263 (2002) (Year: 2002).*
Weber et al. in Cancer Communications 2(4), 129-133 (1990) (Year: 1990).*
Pereira et al. in Anti-Cancer Agents in Medicinal Chemistry, 13(1), 186-192 (2013) (Year: 2013).*
Laubach et al. in Cancer Care and Management 107-117 (2009) (Year: 2009).*
Graham-Pole et al. in Journal of Clinical Oncology 4(7):1110-3 (1986) (Year: 1986).*

(Continued)

*Primary Examiner* — Dennis Heyer
(74) *Attorney, Agent, or Firm* — Grüneberg and Myers PLLC

(57) ABSTRACT

The present invention relates to novel HSP27 inhibitors, in particular thymine derivatives according to general formula (VI), (VII) or (VII) and phenothiazine derivatives according to formula (V), and to their use as drugs for the selective inhibition of the heat shock protein HSP27 (HSPB1), in particular for use in the treatment of carcinomas or cystic fibrosis, said inhibitors having a particularly advantageous activity in the lower micromolar or sub-micromolar active ingredient concentration range with respect to HSP27.

12 Claims, 19 Drawing Sheets

(56) References Cited

FOREIGN PATENT DOCUMENTS

WO 2013/114339 8/2013

OTHER PUBLICATIONS

Figure 1:
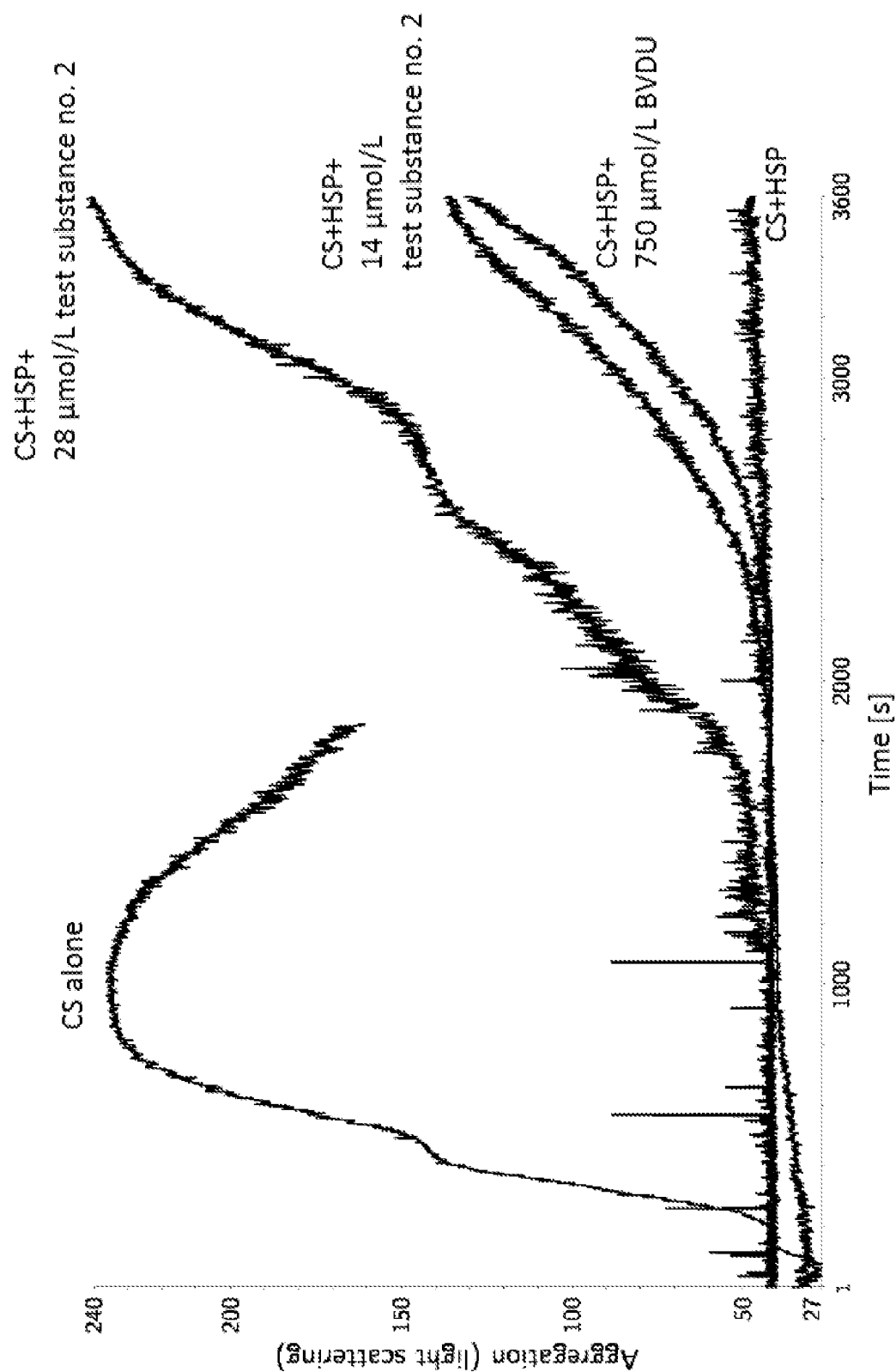

Kukanich B. in Antiemetic Therapy (Proceedings) (2010) at http://veterinarycalendar.dvm360.com/print/302394?page=full (retrieved from the internet Oct. 23, 2018) (Year: 2010).*
Hernandez et al. in Bioorganic & Medicinal Chemistry 13, 3027-3030 (2003) (Year: 2003).*
O. Kalid et al., "Small molecule correctors of F508del-CFTR discovered by structure-based virtual screening," Journal of Computer-Aided Molecular Design (2010) 24:971-991.
Chauhan et al.; "2-Methoxyestardiol and bortezomib/proteasome-inhibitor overcome dexamethasone-resistance in multiple myeloma cells by modulating Heat Shock Protein-27;" Apoptosis; vol. 9; No. 2; 2004, pp. 149-155.
Hernandez et al.; "Acyclic Nucleoside Analogues as Novel Inhibitors of Human Mitochondrial Thymidine Kinase;" J. Med. Chem.; 45; 2002; pp. 4254-4263.
Jakob et al.; "Small Heat Shock Proteins Are Molecular Chaperones*;" The Journal of Biological Chemistry; vol. 268, No. 3, 1993, pp. 1517-1520.
Muckenschnabel et al.; "SpeedScreen: label-free liquid chromatography—mass spectrometry-based high-throughput screening for the discovery of orphan protein ligands;" Analytical Biochemistry; vol. 324; 2004; pp. 241-249.
Richter et al.; "Synthesis, Molecular Modelling and Biological Evaluation of 4-Amino-2(1H)-quinazolinone and 2,4(1H,3H)-Quinazolidone Derivatives as Antitumor Agents;" Arch. Pharm. Chem. Life Sci.; vol. 344; 2011; pp. 810-820.
Straume et al.; "Suppression of heat shock protein 27 induces long-term dormancy in human breast cancer;" Proceedings of the National Academy of Sciences; vol. 109, No. 22, 2012, pp. 8699-8704.
Office Action dated Jan. 7, 2019 in Chinese Application No. 201580040473.7 with English translation, 16 pages.
Banker et al., "Modern Pharmaceutics" Third Edition, Revised and Expanded, Preface and selected pages, Marcel Dekker, Inc. New York, 1996, 3 pages.
Banker et al., "Modern Pharmaceutics" Fourth Edition, Revised and Expanded, Preface and selected pages, Marcel Dekker, Inc. New York, 2002, 10 pages.
Byrn et al., "Hydrates and Solvates," Solid-State Chemistry of Drugs, 2nd Ed. (1999), Ch. 11, 233-247.
Choi et al., "Kinetic Analysis of Translesion Synthesis Opposite Bulky $N^2$-and $O^6$-Alkylguanine DNA Adducts by Human DNA Polymerase REV1," Journal of Biological Chemistry vol. 283, No. 35, Aug. 29, 2008, 23645-23655, DOI: 10.1074/jbc.M801686200.
Davis et al., "Phenotypic Identification of the Redox Dye Methylene Blue as an Antagonist of Heat Shock Response Gene Expression in Metastatic Melanoma Cells," Int. J. Mol. Sci. 2013, 14, 4185-4202, DOI:10.3390/ijms14024185.
Ebalunode, et al., "Novel Approach to Structure-Based Pharmacophore Search Using Computational Geometry and Shape Matching techniques," J. Chem. Inf. Model, 2008, 48 (4), 889-901, DOI: 10.1021/ci700368p.
Focher et al., "$N^2$-Phenyldeoxyguanosine: A Novel Selective Inhibitor of Herpes Simplex Thymidine Kinase," J. Med. Chem. 1988, 31, 1496-1500, XP-002053646.
Gambino et al., "Quantitative Structure-Activity Relationships of $N^2$-Phenylguanines as Inhibitors or Herpes Simplex Virus Thymidine Kinases," J. Med. Chem. 1992, 35, 2979-2983.
Hernández et al., "$N^1$-Substituted Thymine Derivatives as Mitochondrial Thymidine Kinase (TK-2) Inhibitors," J. Med. Chem. 2006, 49, 7766-7773.
Hildebrand et al., "Structure-Activity Relationships of $N^2$-Substituted Guanines as Inhibitors of HSV1 and HSV2 Thymidine Kinases," J. Med. Chem. 1990, 33, 203-206, XP-002744762.
Huang et al., "Efficient synthesis and biological evaluation of 1,2,9-trisubstituted 1,9-dihydro-6H-purin-6-ones," Bioorganic & Medicinal Chemistry Letters 19 (2009) 831-833, DOI: 10.1016/j.bmcl.2008.12.007.
Jego et al., "Targeting heat shock proteins in cancer," Cancer Letters 332 (2013) 275-285.
Kumar et al., "Phenyl 1,2,3-Triazole-Thymidine Ligands Stabilize G-Quadruplex DNA, Inhibit DNA Synthesis and Potentially Reduce Tumor Cell Proliferation over 3'-Azido Deoxythymidine," Plos One, Aug. 2013, vol. 8, Issue 8, e70798, 12 pages DOI: 10.1371/journal.pone.0070798.
McPherson et al., "A cyclic nucleotide PDE5 inhibitor corrects defective mucin secretion in submandibular cells containing antibody directed against the cystic fibrosis transmembrane conductance regulator protein," FEBS Letters 464 (1999) 48-52.
MedicineNet.com (2004) Web: <http://www.medterms.com> https://web.archive.org/web/20040603184158/http://www.medterms.com/script/main/art.asp?articlekey=2580.
Morissette et al., "High-throughput crystallization: polymorphs, salts, co-crystals and solvates of pharmaceutical solids," Advanced Drug Delivery Reviews 56 (2004), 275-300 DOI: 10.1016/j.addr.2003.10.020.
Noonan et al., "The Synthesis and Interaction of Novel GTP Derivatives with Ras Oncogene Proteins," Nucleosides and Nucleotides, 10(1-3), 503-505 (1991) DOI: 10.1080/07328319108046509.
Powers et al., "Inhibitors of the heat shock response: Biology and pharmacology," FEBS Letters 581 (2007) 3758-3769 DOI: 10.1016/j.febslet.2007.05.040.
A. Maureen Rouhi, "The Right Stuff: From research and development to the clinic, getting drug crystals right is full of pitfalls," Chem. & Eng. News, Feb. 24, 2003, pp. 32-35.
Savijoki et al., "New convenient defined media for [$^{35}$S]methionine labelling and proteomic analyses of probiotic lactobacilli," Letters in Applied Microbiology 42 (2006) 202-209 DOI: 10.1111/j.1472-765X.2005.01853.x.
Wright et al., "Synthesis, Cell Growth Inhibition, and Antitumor Screening of 2-(p-n-Butylanilino)purines and Their Nucleoside Analogues," J. Med. Chem. 1987, 30, 109-116.
Xu et al., "Synthesis, Properties, and Pharmacokinetic Studies of $N^2$-Phenylguanine Derivatives as Inhibitors of Herpes Simplex Virus Thymidine Kinases," J. Med. Chem. 1995, 38, 49-57 XP-002053656.

* cited by examiner

THYMINE DERIVATIVES AND QUINAZOLINE-DIONE DERIVATIVES FOR THE INHIBITION OF HSP27

The present invention relates to novel thymine derivatives and their use as medicinal products for the selective inhibition of the heat shock protein HSP27 (HSPB1).

It is known that some types of cancer respond poorly to treatment with cytostatic agents from the start. Even in patients with types of cancer that are actually easy to treat, however, therapy can fail after a certain period. Resistances, whereby the tumour cells become insensitive to cytostatic agents, represent one possible reason. A number of biological processes are known which are behind this.

For example, it has been shown that the treatment of various tumour cell lines with cytostatic agents leads to increased expression of cellular proteins, which are important for the protection and stabilizing of the correct folding of receptors, enzymes and cellular structural proteins.

Heat shock proteins are evolutionarily highly conserved proteins, which are formed by the cell under sublethal stress conditions. Heat shock proteins are chaperones, with natural tasks including returning proteins that have been denatured by heat or chemicals to their functional state or preventing the denaturation of proteins. Because of the way in which they function, heat shock proteins are overexpressed in many cancer cells. In recent years, therefore, heat shock proteins have emerged as promising target proteins for cancer therapy.

The heat shock protein HSP27 (HSPB1) is involved in many cellular processes, e.g. apoptosis (programmed cell death), DNA repair and recombination. HSP27 is overexpressed in the cell in many different types of cancer, e.g. prostate cancer, bowel cancer, liver cancer and breast cancer, and affects the course of the disease. It has been found that increased expression of HSP27 is associated with increased resistance to cytostatic agents, such as e.g. gemcitabine (2',2'-difluorodeoxycytidine) or bortezomib (Velcade), in chemotherapy. Because of the negative effect of HSP27 on chemotherapy, HSP27 is considered to be a promising additional target in cancer therapy, in particular for suppressing the development of chemoresistance.

One possible therapeutic approach is described in JP 2010 215669 A or US 2012/294846 A1 and is based on suppressing the gene expression of HSP27 by direct intervention in translation or transcription by means of intracellular administration of antisense oligonucleotides or double-stranded small interfering (si) RNA. Here, the nucleotide-based inhibitors bind to the DNA or RNA, thereby specifically preventing the formation of HSP27 in the cell.

In connection with this, WO 2013 114339 A1 discloses a combination therapy for the treatment of cancer based on the synergistic effect of a nucleotide inhibitor for inhibiting the expression of HSP27 in conjunction with an EGFR (epidermal growth factor receptor) protein inhibitor, such as e.g. erlotinib, or antifolates such as pemetrexed. The nucleotide inhibitor is preferably an antisense oligonucleotide or a double-stranded siRNA.

However, one disadvantage in the use of nucleotide-based inhibitors is their excess of negative charges and the associated high polarity of the active ingredient molecules, whereby their bioavailability is significantly minimized. Even more problematic is the huge chemical instability of nucleotide-based inhibitors, in particular RNA-based inhibitors.

A further disadvantage is that the transfection (=introduction of foreign oligonucleotides into eukaryotic cells) of the nucleotide-based inhibitors is complex and in some cases of only low efficiency. In addition, short nucleotide-based inhibitors have the disadvantage of a potential immunogenic action, also acting e.g. by secretion on non-transfected cells (e.g. macrophages) and thus inducing a strong immune response in the organism, which is harmful for the patient.

An alternative approach to the use of nucleotide-based inhibitors is represented by low-molecular-weight organic compounds, since these usually exhibit high stability in a biological system together with good bioavailability. In the case of highly specific compounds in particular, the "off-target" effects typical of other methods (e.g. due to the otherwise necessary transfection) do not occur.

DE 10 2008 035 299 A1 describes a method according to which the low-molecular-weight organic compound (E)-5-(2-bromovinyl)-2'-deoxyuridine (BVDU) interacts directly with the protein HSP27, inhibiting the functionality of the HSP27. As a weak HSP27 inhibitor, BVDU thus increases sensitivity to cytostatic-induced apoptosis, so that pancreatic cancer patients obtain a survival benefit through oral administration of BVDU. Clinical studies with late-stage pancreatic cancer patients have shown that BVDU works safely and efficiently at an administered dose of 500 mg/day. However, at an increased administered dose of 760 mg/day, BVDU proved disadvantageous for low-weight patients.

The compound BVDU described above and derivatives thereof in DE 10 2008 035 299 A1 are the only known low-molecular-weight inhibitors of HSP27. The existing active ingredients show considerable potential for improvement in terms of binding affinity.

WO 2009/156182 A2 describes uracil derivatives of general formula I

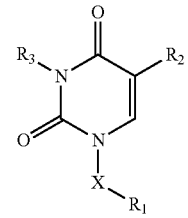

which are employed together with a cytostatic agent to suppress or reduce the development of resistance in cytostatic treatment. WO 2009/156182 A2 shows no methods for the experimental validation of these compounds for the assumptions made; for instance, no values for the inhibitory concentration or for active ingredient concentrations of the individual compounds can be taken from the document.

There is therefore an enormous need to provide more efficient HSP27 inhibitors for the selective and direct inhibition of the HSP27 protein in the context of use in a multifactorial combination therapy, in particular for cancer therapy.

The present invention is therefore based on the object of providing chemical compounds that inhibit the heat shock protein HSP27 as selectively and potently as possible, in particular for use in cancer therapy.

In particular, it is the object of the present invention to provide chemical compounds which, compared with compounds known from the prior art, exhibit a significant retardation or suppression of the development of resistance in cytostatic treatment in cancer chemotherapy.

To achieve the object, purine derivatives according to general formula (I) or (II) are specified for use as medicinal products, in particular for use for the treatment of carcinomas or mucoviscidosis:

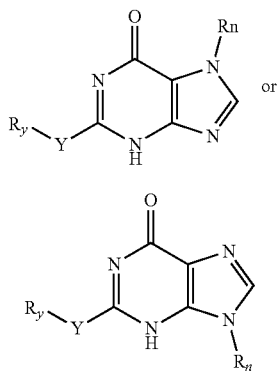

wherein:
$R_n$ is selected from hydrogen (H),

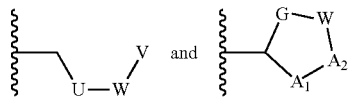

wherein ~~~ is the covalent linkage to general formula (I) or (II) and the variables have the following meanings:
U is selected from oxygen (O), an optionally branched and/or OH-functionalized $C_1$ to $C_4$ alkyl residue and optionally substituted vinyl residue, in particular substituted with halogen, particularly preferably F, Cl, I; U is preferably O or an optionally OH-functionalized $C_1$ to $C_4$ alkyl residue,
W is an optionally substituted methylene (—$CH_2$—), ethylene (—$CH_2CH_2$—), ethoxy (—O—$CH_2CH_2$—) or ethene-1,2-diyl residue (—CH=CH—), and wherein the substituents are preferably selected from —$CH_3$, —$CH_2OH$, —$COOCH_3$, —$CH_2$—$(PO_3H)_o$—OH with o=0, 1, 2 or 3, —$CH_2$-phosphonic acid,
V is selected from H, —OH, an amino acid -AA, wherein the amino acid is in particular selected from the group of proteinogenic amino acids and their corresponding β-AAs and wherein AA is bound covalently to W via the carboxyl group, an optionally substituted heterocycle, in particular a six-membered ring nitrogen heterocycle, such as pyridine, diazine, piperidine or piperazine, and wherein the substituents are preferably selected from —OH and an optionally substituted and/or polycyclic aryl residue, in particular phenyl, naphthalene, quinoline, naphthyridine, and wherein the substituents on the aryl residue are preferably selected from —$CF_3$, —F, —Cl, —I, —OH, —$NH_2$, =O, —COOH, —$OCH_3$, —R,
$A_1$ and $A_2$ independently of one another are —$CH_2$, —CHOR, —CHF— or —CHOC(=O)R,
G is $CH_2$, —$CH_2O$— or O,
Y is O, S, NR, carboxyl, carbonyl or amide,
wherein R is an H or an optionally OH-functionalized $C_1$ to $C_8$ alkyl residue, the substituent $R_y$ is H, OH, an optionally substituted $C_1$ to $C_7$ alkyl residue, an optionally substituted cyclic or polycyclic aryl residue or an optionally polycyclic nitrogen heterocycle, in particular an optionally substituted phenyl, naphthalene, bisphenyl, phenanthrene, benzopyrene, pyridine, diazine, triazole, piperidine, bipiperidine, piperazine, xanthene, carbazole, 9,10-dihydrophenanthrene, phenothiazine, triphenylmethane residue or a combination thereof, wherein the substituents are selected from —F, —$NH_2$, R and the group of the six-membered ring nitrogen heterocycle, in particular pyridine, 1,2-diazine, 1,3-diazine, piperidine, bipiperidine or piperazine or a sequence of two to three of the above-mentioned substituents bridged to one another in para-position. Alternatively, $R_y$ is —C=O or is selected from —$CR_aR_bR_c$ wherein $R_a$, $R_b$ and $R_c$ are selected independently of one another from H and cyclic residues.

The object of the invention is furthermore achieved by thymine derivatives of general formula (VI) or (VII):

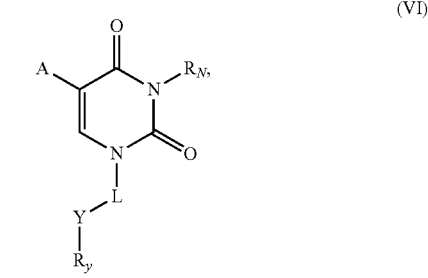

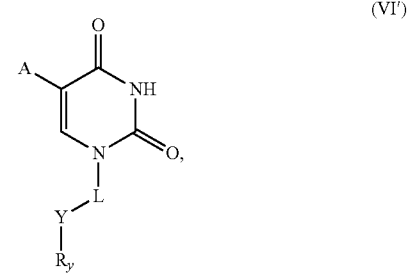

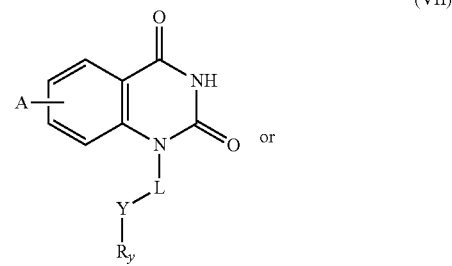

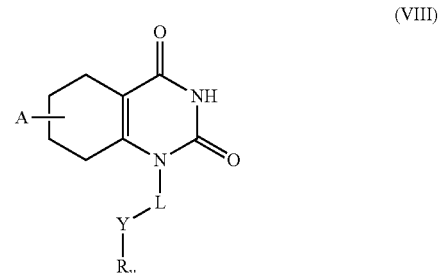

wherein the variables have the following meanings:

the substituent A is —H, —CH$_3$ or an optionally substituted C$_2$ to C$_4$ vinyl or alkynyl residue, in particular substituted with halogen, particularly preferably F, Cl, I; alternatively, A is a halogen, —NO$_2$, —C=O, phenyl or thiophene residue—the halogen preferably being selected from I and Br;

the linker L preferably serves to restrict the conformational flexibility (i.e. reduction in entropy) and is selected from an optionally substituted phenyl, benzyl or pyridine residue, in particular substituted with —CH$_3$, —CF$_3$, halogen, particularly preferably substituted with —CF$_3$ and F,

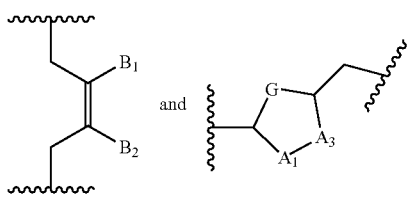

wherein

〰〰 is the covalent linkage to general formula (VI) or (VII) or is Y, the substituents B$_1$ and B$_2$ independently of one another are —H, —CH$_3$, —CF$_3$, —F or —Cl, A$_1$, is —CH$_2$—, —CHOR, —CHF— or —CHOC(=O)R, A$_3$ is —CH$_2$—, —CHOR, —CHF—, —CHOC(=O)R or —CHK—, wherein K is an optionally substituted five-membered ring nitrogen heterocycle, in particular triazole, diazole or imidazole, wherein the five-membered ring nitrogen heterocycle is preferably bound covalently to A$_3$ via a nitrogen atom.

G is CH$_2$, —CH$_2$O— or O;

Alternatively, the linker L is selected from optionally substituted C1 to C6 alkyl residues or

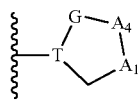

wherein G and A$_1$ are selected as above and A$_4$ is —CH$_2$— or —CHOR and T is CH and/or T and G or G and A$_4$ together form a cyclopropyl ring;

Y is O, S, NR, carboxyl, carbonyl or amide, wherein R is an H or an optionally substituted and/or branched C$_1$ to C$_8$ alkyl residue, the substituent R$_y$ is as defined above or below H, OH, an optionally substituted cyclic or polycyclic aryl residue or an optionally substituted oxygen or nitrogen heterocycle, wherein the substituents are selected from —F, —NH2, R and the group of the six-membered ring nitrogen heterocycles, in particular pyridine, 1,2-diazine, 1,3-diazine, piperidine, bipiperidine or piperazine or a sequence of two to three of the above-mentioned substituents bridged to one another in para-position;

Alternatively, R$_y$ is —C=O or is selected from —CR$_a$R$_b$R$_c$ wherein R$_a$, R$_b$ and R$_c$ are selected independently of one another from H and cyclic residues, preferably selected from optionally substituted cyclic or polycyclic aryl residues and optionally substituted heterocycles, particularly preferably H, phenyl, naphthylene, biphenyl. Preferably, at least one of the residues R$_a$, R$_b$ and R$_c$ is H and at least one of the residues is a cyclic residue, which is preferably selected as above;

the substituent R$_N$ in formula (IV) is H or a benzoyl residue.

Advantageously, taking account of the steric effects, the substituent R$_y$ on the purine derivative according to formula (I) or (II) or the thymine derivative of formula (VI), (VI'), (VII) or (VIII) is adapted to the active ingredient binding pocket in such a way that the substituent R$_y$ represents a planar system. The planar system does not necessarily have to be a conjugated system here. Preferably, the substituent R$_y$ on the purine derivative according to formula (I) or (II) or the thymine derivative of formula (VI), (VI'), (VII) or (VIII) is an optionally substituted cyclic or polycyclic aryl residue or a nitrogen heterocycle, in particular selected from optionally substituted phenyl, naphthalene, bisphenyl, phenanthrene, benzopyrene, pyridine, diazine, xanthene, carbazole, phenothiazine, triphenylmethane, piperidine, bipiperidine, piperazine residues and a combination thereof. Preferably, taking account of the steric effects, the substituents of the cyclic or polycyclic aryl residue or of the nitrogen heterocycle have an and/or –M effect, whereby the purine derivatives of formula (I) or (II) and the thymine derivatives of formula (VI), (VI'), (VII) or (VIII) advantageously have a higher binding affinity to the active ingredient binding pocket of the HSP27 protein. Preferably, the substituents of the cyclic or polycyclic aryl residue or of the nitrogen heterocycle are selected from -halogen, —NO$_2$, —CN, —N(R)$_2$, —SR, —OR, —COOR, —COR, R, wherein R as defined above is H or a C1 to C8 alkyl residue. Particularly preferably, the substituents of the cyclic or polycyclic aryl residue or of the nitrogen heterocycle are, independently of one another, substituents having an —I and/or –M effect selected from H, —NO$_2$, —CF$_3$, —F, —Cl, —Br, —OH, —COOH, —OCH$_3$ and —COR; quite particularly preferably, the substituents are selected independently of one another from H, —NO$_2$, —CF$_3$, —OH, —COOH and F.

Alternatively or in addition, K is preferably selected independently of R$_y$ from the same residues as mentioned above for R$_y$. This applies in particular when R$_y$ is H or OH. The purine derivative according to formula (I) or (II), in addition to the basic purine structure, preferably has at least one optionally substituted cyclic or polycyclic aryl residue or an optionally substituted nitrogen heterocycle in R$_n$ or R$_y$.

The thymine derivative according to formula (VI), (VI'), (VII) or (VIII) preferably has, in addition to the basic thymine structure, at least one optionally substituted aliphatic cyclic or polycyclic residue (preferably in L) or an optionally substituted cyclic or polycyclic aryl residue or an or an optionally substituted oxygen or nitrogen heterocycle (preferably in K or R$_y$). Preferably, the nitrogen heterocycle is further substituted. Particularly preferably, the nitrogen heterocycle is a triazole ring, which is preferably linked in position 1 to Y or —CH in —CHK and is preferably substituted in position 4 of the triazole ring. Preferred substituents have the formula —R$_T$E with R$_T$ selected from a single bond and C1 to C5 alkyl and E selected from cyclic residues. The cyclic residues in E are preferably mol/Locyclic residues, particularly preferably selected from cyclopentyl, pyridine and phenyl and mol/Lo- or polyhalogen (preferably Br, Cl or F) substituted phenyl.

According to a particularly advantageous embodiment of the present invention, the linker L is an optionally substituted phenyl, benzyl or pyridine residue, in particular substituted with —CH₃, —CF₃ or halogen, particularly preferably substituted with —CF₃ and —F,

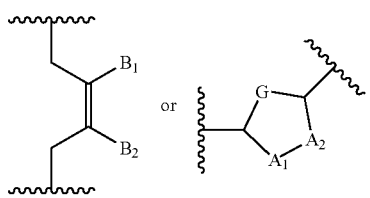

wherein the substituents B₁ and B₂ are, independently of one another, —H, —CH₃, —CF₃, —F or —Cl, A₁ and A₂ are, independently of one another, —CH₂—, —CHOR, —CHF— or —CHOC(=O)R and G is CH₂ or O. Thymine derivatives of general formula (VI), (VI'), (VII) or (VIII), in which the ligand is selected as listed above, exhibit a high binding affinity to the active ingredient binding pocket of the HSP27 protein (i.e. reduction in entropy).

Restriction of the conformational flexibility (i.e. reduction in entropy) within the meaning of the present invention means that a certain conformational flexibility is retained in the molecule, although the number of possible conformations in the molecule and the energy barrier for the conformational flexibility of the molecule are severely restricted.

The term "optionally substituted" is understood to mean an unsubstituted or substituted residue.

The term "polycyclic aryl residue" within the meaning of this invention is to be understood as a conjugated system containing at least two arylene groups which are connected together directly, i.e. are in conjugation with one another. The arylene groups here can also be connected together directly via an electron donor (e.g. nitrogen, oxygen, CH) and thus create the planarity of the system, such as e.g. xanthenes, carbazoles, phenothiazines or triphenylmethane.

Advantageously, purine derivatives according to general formula (I) or (II) and thymine derivatives of formula (VI), (VI'), (VII) or (VIII) inhibit the HSP27 protein by means of a specific interaction with the active ingredient binding pocket of the HSP27 protein.

The advantage of the purine derivatives according to general formula (I) or (II) and the thymine derivatives according to general formula (VI), (VI'), (VII) or (VIII) for use in cancer therapy consists in the fact that these compounds have an activity at least 50 times higher than currently known compounds for the selective inhibition of HSP27.

Particularly advantageously, the purine derivatives of general formula (I) or (II) and thymine derivatives according to general formula (VI), (VI'), (VII) or (VIII) already have an activity with respect to HSP27 in the lower micromolar or submicromolar active ingredient concentration range. According to a preferred embodiment of the present invention, the purine derivatives of general formula (I) and (II) and thymine derivatives of formula (VI), (VI'), (VII) or (VIII) or thymine derivatives of formula (VI), (VI'), (VII) and (VIII) are employed with an active ingredient concentration in the range of 1 nmol/L to 1000 μmol/L, preferably in the range of 10 nmol/L to 750 μmol/L, further preferably 100 nmol/L to 500 μmol/L or 10 nmol/L to 100 pmol/L, particularly preferably 100 nmol/L to 10 μmol/L.

"Inhibition of HSP27" within the meaning of the present invention means that, by interaction with a low-molecular-weight compound, preferably the purine derivative of general formula (I) or (II), the thymine derivatives according to general formula (VI), (VI'), (VII) or (VIII) or phenothiazine derivatives according to formula (V), the HSP27 loses its capacity to interact with cancer-triggering binding partners (e.g. proteins) and at the same time advantageously induces the introduction of apoptosis (e.g. by stimulated activity of caspases). Caspases are the most important enzymes in apoptosis (programmed cell death) in animals.

The present invention is based on the very recent finding that HSP27, which is overexpressed in many types of cancer and has a negative effect on the course of the disease, has an active ingredient binding pocket for low-molecular-weight organic compounds, said binding pocket being central to the functionality (e.g. binding to client proteins and probably also oligomerization) of the HSP27 protein and its activity. The functionality of the active ingredient binding pocket is based on two phenylalanine residues at positions 29 and 33 (Phe29 and Phe33) in the amino acid sequence of the protein. Thus, it has been shown that mutants lacking the corresponding phenylalanine residues are incapable of interacting with purine derivatives of general formula (I) or (II).

Since the corresponding crystal structural data for the HSP27 protein do not exist, the active ingredient binding pocket of HSP27 was computer-modelled with the aid of various in silico methods.

Within the meaning of the invention, the active ingredient binding pocket of the HSP27 protein is a localized region (local tertiary structure), which is formed by spatial arrangement of the amino acid sequence and comprises the phenylalanine residues Phe29 and Phe33 (based on the primary structure of HSP27). The active ingredient binding pocket of HSP27 is capable of interacting with a low-molecular-weight organic compound, preferably by means of coordinative interaction, in such a way that the HSP27 protein loses its functionality (capacity for oligomerization and interaction with client proteins). A client protein here is a substrate, preferably a protein, on which HSP27 acts as a chaperone. The binding affinity here is a measure of the binding strength between binding partners (here the low-molecular-weight organic compound) and a target protein. The higher the binding affinity between the binding partner and the target protein, the lower is the dissociation constant ($K_D$). The inhibitory concentration ($K_i$) of the binding partner refers to the concentration at which complete inhibition of the target protein is present. It is understood that the lower the value of $K_i$, the higher the binding affinity.

Through a precise knowledge of the tertiary structure of the active ingredient binding pocket of HSP27, virtual screening can be used to pre-identify low-molecular-weight organic compounds which, compared with known compounds, interact significantly more specifically with the active ingredient binding pocket of HSP27.

The term "virtual screening" comprises a medicinal product research process known to a person skilled in the art, in which novel active ingredient molecules are to be found by means of in silico methods (i.e. in computer experiments). The binding affinity ($K_i$) of these potential inhibitors is not measured by wet chemical experiments here, as in traditional screening, but is predicted by computer-based methods.

By means of the binding/interaction of a low-molecular-weight organic compound or inhibitor on the active ingredient binding pocket of HSP27, the structure of the HSP27 protein can undergo changes. Often, these changes are limited to side chain conformations, but entire groups of amino acids with their peptide backbone can also move.

Advantageously, as a result of virtual screening, only a few low-molecular-weight organic compounds then have to be tested experimentally by in vitro (i.e. outside a living organism), in situ (i.e. in cells, preferably in cell cultures) and/or in vivo (i.e. in the living organism) experiments for their physicochemical affinity towards the active ingredient binding pocket of HSP27, which increases efficiency in identifying specific HSP27 inhibitors and at the same time reduces costs. These in vitro experiments for identifying affinity towards the active ingredient binding pocket of HSP27 take place e.g. by means of binding assays, in which the association of two unlabelled binding partners is measured (e.g. bio-layer interferometry). In the case of HSP27, furthermore, the function of the target protein or its inhibition can be quantitatively measured in aggregation assays.

In in vitro experiments, it has now been found that the purine derivatives of general formula (I) or (II) and thymine derivatives of formula (VI), (VI'), (VII) or (VIII) according to the invention have a dissociation constant ($K_D$) in respect of the HSP27 protein in the range of 10 nM/L to 1000 μmol/L, preferably in the range of 100 nM/L to 800 μmol/L.

In situ, the inhibiting action of the pre-identified low-molecular-weight organic compounds on the functionality of the HSP27 protein is preferably measured in cells that express HSP27. Preferably, the in situ methods are performed with the aid of common, readily cultured cell lines in which the binding partners are expressed. Suitable cell lines are U937 and RPMI-8226 as examples of cancer cell lines and CCD-186Sk as an example of a mucoviscidosis cell line. The detection of the efficacy of the low-molecular-weight organic compounds preferably takes place here by measuring the development of resistance to a cytostatic agent or determining the interaction between HSP27 and its binding partners (e.g. by measuring the caspase-3 activity).

The term "low-molecular-weight organic compound" within the meaning of the invention is understood to mean molecular compounds composed primarily of the elements carbon, hydrogen, oxygen and nitrogen and preferably having a molecular weight in the range of 100 to 900 g/mol, in particular of 150 to 750 g/mol, above all 200 to 600 g/mol.

Low-molecular-weight organic compounds have the significant advantage over large molecules (e.g. nucleotide-based inhibitors such as antisense oligonucleotides or RNA oligonucleotides) that they are substantially easier to handle and more stable under physiological conditions. Furthermore, low-molecular-weight organic compounds are usually cell-penetrating and therefore easier to administer into the cell or an organism.

Surprisingly, it has now been found that in particular purine derivatives according to general formula (I) or (II) and thymine derivatives according to general formula (VI), (VI'), (VII) or (VIII) as low-molecular-weight organic compounds bind selectively to the active ingredient binding pocket of the HSP27 protein and thus already inhibit the functionality of the HSP27 protein in the lower micromolar or submicromolar concentration range.

Preferably, the substituent $R_y$ is an optionally substituted cyclic or polycyclic aryl residue or an optionally polycyclic and/or substituted nitrogen heterocycle, which is selected in particular from a phenyl, naphthalene, bisphenyl, phenanthrene, benzopyrene, pyridine, diazine, triazole, piperidine, bipiperidine, piperazine, xanthene, carbazole, phenothiazine, 9,10-dihydrophenanthrene, triphenylmethyl residue or a combinations thereof. Preferably, the six-membered ring nitrogen heterocycle is bound covalently to the general formula (I) or (II) via a nitrogen atom.

According to an alternatively preferred embodiment of the present invention, the substituent $R_y$ on the thymine derivative according to general formula (VI), (VI'), (VII) or (VIII) is selected from a phenyl, triazole, piperazine, diazine and triphenylmethyl residue, which can in particular be substituted with a six-membered ring nitrogen heterocycle, in particular pyridine, 1,2-diazine, 1,3-diazine, piperidine, bipiperidine or piperazine or a sequence of two to three of the above-mentioned substituents bridged to one another in the para-position.

It may optionally be provided that the substituent $R_y$ on the thymine derivative according to general formula (VI) or (VII) is H or OH, i.e. a sterically undemanding residue, wherein $A_3$ is particularly preferably —CHK—, i.e. a sterically demanding residue, wherein K is an optionally substituted five-membered ring nitrogen heterocycle, in particular triazole, diazole or imidazole, wherein the five-membered ring nitrogen heterocycle is preferably bound covalently to $A_3$ via a nitrogen atom. The substituent on the five-membered ring nitrogen heterocycle here is selected in particular from a phenyl, pyridine and diazine residue.

According to a preferred embodiment of the present invention, the substituent $R_y$ on the purine derivative according to general formula (I) or (II) or the thymine derivative according to general formula (VI), (VI'), (VII) or (VIII) is adapted to the active ingredient binding pocket in such a way that $R_y$ is selected from H, general formula (III) or formula (IV):

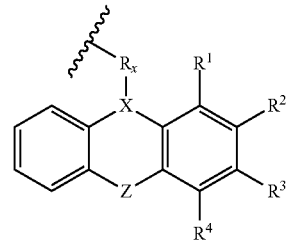

(III)

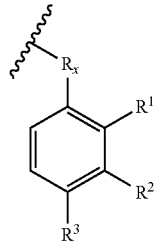

(IV)

wherein:
⁓ is the covalent linkage to general formula (I), (II) or (VI), (VI'), (VII) or (VIII),
X is N or CH,
Z is a single bond, $CH_2$, O, C(=O), S or $NR_x$, in particular $CH_2$, O, C(=O), S or $NR_x$, particularly preferably $CH_2$, O, S or $NR_x$,
$R_x$ is an optionally substituted and/or branched $C_1$ to $C_4$ alkyl residue,
$R^1$, $R^2$, $R^3$ and $R^4$ independently of one another are —H, -halogen, —$NO_2$, —CN, —$NR_2$, and —SR, —OR, —COOR, —COR, —R or an optionally substituted $C_1$ to $C_4$ vinyl residue or optionally substituted aryl residue, wherein R as defined above is H or a $C_1$ to $C_8$ alkyl residue.
Alternatively, $R_y$ is preferably selected from —$CR_aR_bR_c$ wherein $R_a$, $R_b$ and $R_c$ are selected independently of one another from H and cyclic residues, preferably selected from optionally substituted cyclic or polycyclic aryl residues and optionally substituted heterocycles, particularly preferably H, phenyl, naphthylene, biphenyl. Preferably, at least one of the residues $R_a$, $R_b$ and $R_c$ is H and at least one of the residues is a cyclic residue, which is preferably selected as above.

By adapting the structures to the active ingredient binding pocket of the protein, the purine derivatives according to general formula (I) and (II) or thymine derivatives of formula (VI), (VI'), (VII) and (VIII) particularly advantageously exhibit an activity in the lower micromolar or submicromolar, particularly preferably in the nanomolar concentration range.

According to a preferred embodiment of the present invention, the substituents $R^1$ to $R^4$, taking into account the steric effects, have an —I and/or –M effect and therefore the purine derivatives according to general formula (I) or (II) or thymine derivatives according to general formula (VI), (VI'), (VII) or (VIII) advantageously have a high binding affinity to the active ingredient binding pocket of the HSP27 protein (i.e. low $K_i$ and $K_D$). Preferably, the substituents $R^1$ to $R^4$ independently of one another are substituents having an —I and/or –M effect selected from H, —$NO_2$, —$CF_3$, —F, —Cl, —Br, —OH, —COOH, —$OCH_3$ and —COR; particularly preferably, the substituents are selected independently of one another from H, —$NO_2$, —$CF_3$, —OH, —COOH and F. According to a quite particularly preferred embodiment of the present invention, exclusively two, particularly preferably exclusively one of the substituents $R^1$ to $R^4$ have/has a substituent other than H.

According to an alternatively preferred embodiment of the present invention, one of the substituents $R^1$ to $R^4$, quite particularly preferably $R^3$, is an optionally substituted aryl residue having a marked +M effect, preferably a phenyl residue or a six-membered ring nitrogen heterocycle selected from pyridine, pyridazine, pyrimidine or pyrazine. Quite particularly preferably, one of the substituents $R^1$ to $R^4$ is an optionally substituted six-membered ring nitrogen heterocycle.

The binding affinity of purine derivatives of general formula (I) and (II) to the active ingredient binding pocket of the HSP27 protein is determined inter alia by the nature of the substituent $R_n$. Preferably, $R_n$ is a sterically undemanding, small substituent selected from H, an optionally branched $C_1$-$C_4$ alkyl or ether residue, wherein V is H or OH, an optionally substituted five-membered ring or six-membered ring oxygen heterocycle. In particular, purine derivatives of general formula (I) or (II) in which $R_n$ is H, an optionally OH-functionalized methyl, ethyl, n-propyl, iso-propyl, n-butyl, iso-butyl, tert-butyl residue or an optionally substituted five-membered ring oxygen heterocycle substituted via C1', in particular furan, ribose, deoxyribose or dideoxyribose, displayed a particularly high binding affinity to the active ingredient binding pocket of the HSP27 protein (i.e. low $K_i$ and $K_D$). Preferably, such purine derivatives of general formula (I) and (II) in which $R_n$ is as defined above have a $K_i$ with respect to HSP27 in the range of 10 nmol/L to 5 mmol/L, particularly preferably in the range of 50 nmol/L to 5 mmol/L.

Alternatively, it can be provided that the substituent $R_n$ is substantially composed of two parts, wherein part 1 comprises U and W and part 2 comprises V. Preferably, part 1 (U and W) is an optionally branched $C_1$-$C_4$ alkyl or ether residue and part 2 (V) is a substituted six-membered ring nitrogen heterocycle, such as pyridine, diazine, piperidine or piperazine, and wherein the substituents of the six-membered ring nitrogen heterocycle are preferably selected from —OH and an optionally substituted and/or polycyclic aryl residue, in particular phenyl, naphthalene, quinoline, naphthyridine, and wherein the substituents on the aryl residue are preferably selected from —CF3, —F, —OH, —$NH_2$, =O, —COOH, —$OCH_3$ and a C1 to C3 alkyl residue. Preferably, such purine derivatives of general formula (I) and (II) in which $R_n$ is as defined above have a $K_i$ with respect to HSP27 at least in the lower micromolar or submicromolar range, particularly preferably in the nanomolar range, quite particularly preferably in the range of 10 nmol/L to 200 nmol/L.

According to a preferred embodiment of the present invention, the substituent $R_n$ is

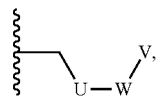

wherein V is an amino acid AA which is bound covalently to W via its carboxyl group. Preferably, the amino acid is selected from the group of proteinogenic amino acids and their corresponding β-AA, but AA is quite particularly preferably selected from the group of hydrophobic (=nonpolar) proteinogenic amino acids and their corresponding β-AA, e.g. alanine, valine, leucine, isoleucine, phenylalanine or tryptophan, as a result of which the binding affinity of purine derivatives of general formula (I) and (II) to the active ingredient binding pocket of HSP27 is advantageously further increased.

In particular, purine derivatives according to general formula (I) or (II) or thymine derivatives according to general formula (VI), (VI'), (VII) or (VIII) are preferred in which, for the substituent $R_y$ according to formula (III), Z is —O—, —C(=O)— or —S— and X is N or CH, wherein purine derivatives in which Z is —O— or —C(=O)— and X is CH have proved to be particularly selective HSP27 inhibitors, i.e. with high binding affinity to the active ingredient binding pocket of the HSP27 protein (i.e. low $K_i$ and $K_D$).

Purine derivatives according to general formula (I) or (II) or thymine derivatives of formula (VI), (VI'), (VII) or (VIII) are preferred in which Y is an O, NR, a six-membered ring nitrogen heterocycle, in particular pyridine, diazine, piperidine or piperazine, or an amide group (—NH—C(=O)—), wherein Y is particularly preferably an NR or pyridine, diazine, piperidine or piperazine. In the event that Y is an amide group, the amide group is preferably oriented such that the C(=O) group binds directly to the substituent $R_y$ according to general formula (III) or (IV).

According to a particularly preferred embodiment of the invention, $R^1$, $R^3$ and optionally $R^4$ of the substituent $R_y$ on purine derivatives according to general formula (I) or (II) or thymine derivatives according to general formula (VI) are H. In this case, in particular variations of purine derivatives according to general formula (I), (II) and thymine derivatives according to general formula (VI), (VI'), (VII) or (VIII) in which the phenyl ring according to formula (IV) only comprises the substituent $R^2$ in meta-position and wherein $R^1$ and $R^3$ are H displayed particularly high binding affinity to the active ingredient binding pocket of the HSP27 protein. According to a quite particularly preferred embodiment of the present invention, for the substituent $R_y$ according to formula (IV), $R^1$ and $R^3$ are H and $R^2$ is an optionally substituted phenyl residue.

Alternatively, purine derivatives according to general formula (I) and (II) or thymine derivatives according to general formula (VI), (VI'), (VII) and (VIII) preferably only comprise the substituent $R^1$ in ortho-position on the phenyl ring according to formula (IV) and/or $R^3$ in para-position, wherein $R^2$ in meta-position is H. According to a quite particularly preferred embodiment of the present invention, for the substituent R according to formula (IV), $R^1$ and $R^2$ are H and $R^3$ is an optionally substituted phenyl residue.

According to a quite particularly preferred embodiment of the present invention, for the substituent $R_y$ according to formula (IV), $R^1$ is H and $R^2$ and $R^3$ are, independently of one another, R or an optionally substituted $C_1$ to $C_4$ vinyl residue, wherein R is H or an optionally OH-functionalized $C_1$ to $C_5$ alkyl residue.

According to a quite particularly preferred embodiment of the present invention, for the substituent $R_y$ according to formula (III), $R^1$, $R^3$ and $R^4$ are H and $R^2$ is H, -halogen, —COR or an optionally substituted phenyl residue.

Also a subject of the invention are HSP27 inhibitors, in particular selected from the group of the purine derivatives of general formula (I) or (II), the thymine derivatives according to general formula (VI) and/or phenothiazine derivatives of general formula (V), for the suppression of the development of chemoresistance in cancer therapy and for use in the treatment of mucoviscidosis.

Mucoviscidosis is a hereditary disease, wherein in most cases of cystic fibrosis the CFTR protein (cystic fibrosis transmembrane conductance regulator) at position 508, owing to a deletion of three nucleotides in the DNA sequence coding for CFTR, lacks the amino acid phenylalanine (Phe508). The CFTR protein is a transmembrane protein, which regulates the transport of water and salt in the plasma membrane of epithelial cells. The resulting protein of the deletion mutant ΔF508 is not folded entirely correctly during its formation (translation). It is therefore not transported to the cell membrane via the endoplasmic reticulum, but is encapsulated with the assistance of HSP27 and transported for degradation.

Commercially known treatment methods for mucoviscidosis only combat the various symptoms that are associated with the disease.

Surprisingly, it has now been found that, by means of the inhibition of the HSP27 protein by the specific interaction of the active ingredient binding pocket of HSP27 with low-molecular-weight compounds, in particular with purine derivatives of general formula (I) or (II), thymine derivatives according to general formula (VI), (VI'), (VII) or (VIII) and/or phenothiazine derivatives of general formula (V), the deletion mutant ΔF508 is protected from degradation and consequently, to a certain degree, transported to the cell membrane where it is functionally integrated. Advantageously, the deletion mutant ΔF508 that has been functionally integrated into the cell membrane can perform its natural function as a cAMP-regulated chloride channel.

According to a further preferred embodiment of the present invention, in particular the purine derivatives of general formula (I) and (II) or thymine derivatives according to general formula (VI), (VI'), (VII) and (VIII) but also phenothiazine derivatives of general formula (V) are suitable as medicinal products for use in cancer therapy, in particular for suppressing the development of chemoresistance, and in the treatment of mucoviscidosis. Also a subject of the invention is the use of these compounds for preparing a medicinal product, preferably for use in cancer therapy, in particular for suppressing the development of chemoresistance, and in the treatment of mucoviscidosis.

The present invention also comprises compounds such as pharmacologically acceptable salts, prodrugs, enantiomers, diastereomers, racemic mixtures, crystalline forms, amorphous forms and solvates, having a purine derivative according to general formula (I) and (II) or a thymine derivative of general formula (VI), (VI'), (VII) and (VIII), for use as medicinal products in cancer therapy, in particular for suppressing the development of chemoresistance, and the treatment of mucoviscidosis.

A pharmacologically acceptable salt within the meaning of the present invention is understood to be chemical compounds of the purine derivative according to general formula (I) and (II) or of the thymine derivative of formula (VI), (VI'), (VII) and (VIII) composed of positively and negatively charged ions, which, depending on the substituents of the purine derivative, can be obtained e.g. by treatment with a weak, pharmaceutically acceptable acid or base.

The term prodrug refers to an inactive or less active pharmacological substance, which is only converted to the pharmacologically active form of a purine derivative according to general formula (I) or (II) or of a thymine derivative according to general formula (VI), (VI'), (VII) and (VIII) by a chemical modification under physiological conditions (i.e. by metabolic processes or metabolization) in the organism. It can also be provided here that the prodrug is converted to the pharmacologically active form of a purine derivative according to general formula (I), (II) or of a thymine derivative according to general formula (VI), (VI'), (VII) or (VIII) by means of chemical or biochemical methods in an ex vivo environment.

The possibility of administering a compound containing a purine derivative according to general formula (I) or (II) and/or a thymine derivative according to general formula (VI), (VI'), (VII) or (VIII) into an organism depends on the structure of the compound. A particularly advantageous property of the purine derivatives according to general formula (I) or (II) and the thymine derivatives according to general formula (VI), (VI'), (VII) or (VIII) compared with conventional nucleotide-based inhibitors is that, as low-molecular-weight organic compounds within the meaning of the invention, they have a bioavailability which is e.g. largely independent of the pH in the stomach. According to a particularly preferred embodiment of the present invention, compounds containing a purine derivative according to general formula (I) and/or (II) and/or a thymine derivative of formula (VI) or (VII) are administered to an organism by an oral or parenteral route and are resorbed via the mucous membranes. For administration orally, pharmaceutical formulations e.g. in the form of a tablet, capsule or liquid, or rectally in the form of suppositories, are suitable. Examples of organisms within the meaning of the present invention are preferably selected from the group of the mammals, wherein the purine derivative according to general formula (I) or (II) and/or thymine derivative of formula (VI), (VI'), (VII) or (VIII) can quite particularly preferably be administered to a human.

A further subject of the invention is a pharmaceutical formulation containing at least one purine derivative according to general formula (I) or (II) and/or thymine derivatives according to general formula (VI), (VI'), (VII) or (VIII) for use in cancer therapy or the treatment of mucoviscidosis.

In this case, the purine derivatives according to general formula (I) or (II) and/or the thymine derivatives according to general formula (VI), (VI'), (VII) or (VIII) can be used in the pharmaceutical formulation as the sole pharmacologically active ingredient or in combination with at least one cytostatic agent, e.g. in order to extend the spectrum of activity or prevent the development of resistances. In many cases, additive or synergistic effects are obtained here, i.e. the efficacy of the mixture is greater than the efficacy of the individual components.

It is known that the reduced activity of the HSP27 protein in the cell, independently of the administration of at least one cytostatic agent, already leads to a state of long-term stability in the malignant degeneration of cancer cells and thus contributes to significantly reduced tumour growth [Straume et al., 2012]. Against this background, according to a preferred embodiment of the present invention the pharmaceutical formulation according to the invention only has one active ingredient in the form of the purine derivative according to general formula (I) or (II) or the thymine derivative of general formula (VI) or (VII).

Particularly preferred, however, is a pharmaceutical formulation according to the invention containing the purine derivative according to general formula (I) or (II) and/or the thymine derivative of general formula (VI), (VI'), (VII) or (VIII) in combination with at least one cytostatic agent. Such a pharmaceutical formulation according to the invention thus offers the particular advantage that the development of resistance during cytostatic treatment is prevented or at least significantly delayed. Examples of cytostatic agents are: folic acid antagonists (e.g. methotrexate, pemetrexed), pyrimidine analogs (e.g. 5-fluorouracil, gemcitabine), purine analogs (e.g. pentostatin, azathioprine) and oligopeptides with N- or C-terminal protection (e.g. bortezomib).

As described above, the purine derivative of general formula (I) or (II) and/or the thymine derivative of general formula (VI), (VI'), (VII) or (VIII) can be administered orally in the form of tablets, capsules, liquids or syrup or rectally in the form of suppositories.

It has also surprisingly been found that phenothiazine derivatives according to general formula (V):

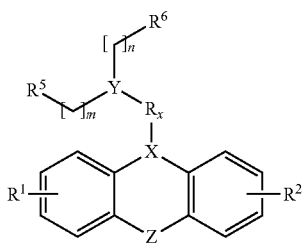

(V)

wherein:

X is N and Z is S, $R_x$ is an optionally substituted and/or branched $C_1$ to $C_4$ alkyl, alkenyl or alkynyl residue, the substituents $R^1$ and $R^2$ in ortho-, meta- or para-position are, independently of one another, —H, —OR, —C(=O)R, —CF$_3$, -halogen, an aliphatic or aromatic heterocycle, Y is N or an amide group (—NR—C(=O)—), n and m are, independently of one another, an integer from 0 to 3, $R^5$ and $R^6$ are, independently of one another, H, an optionally substituted piperazine, phenyl (—C$_6$H$_5$), hydroxyphenyl (—OC$_6$H$_5$) or phenylene residue (—C$_6$H$_4$—), are also capable of selectively binding to the active ingredient binding pocket of the HSP27 protein, thereby inhibiting the functionality of the HSP27 protein, and so phenothiazine derivatives are suitable for use in cancer therapy or the treatment of mucoviscidosis.

Typical examples of phenothiazine derivatives according to general formula (V) are known to a person skilled in the art and are e.g. (MW=molecular weight):

| CAS Number | Phenothiazine derivatives | Molecular formula | MW [g/mol] |
|---|---|---|---|
| 61-00-7 | Acepromazine | $C_{19}H_{22}N_2OS$ | 326.46 |
| 50-53-3 | Chlorpromazine | $C_{17}H_{19}ClN_2S$ | 318.86 |
| 60-99-1 | Levomepromazine | $C_{19}H_{24}N_2OS$ | 328.47 |
| 58-40-2 | Promazine | $C_{17}H_{20}N_2S$ | 284.42 |
| 60-87-7 | Promethazine | $C_{17}H_{20}N_2S$ | 284.42 |
| 146-54-3 | Triflupromazine | $C_{18}H_{19}F_3N_2S$ | 352.42 |
| 84-97-9 | Perazine | $C_{20}H_{25}N_3S$ | 339.50 |
| 58-39-9 | Perphenazine | $C_{21}H_{26}ClN_3OS$ | 403.97 |
| 69-23-8 | Fluphenazine | $C_{22}H_{26}F_3N_3OS$ | 437.52 |

Alternative examples of phenothiazine derivatives according to general formula (V) are also (with the respective calculated inhibitory concentration in relation to HSP27—$K_i$):

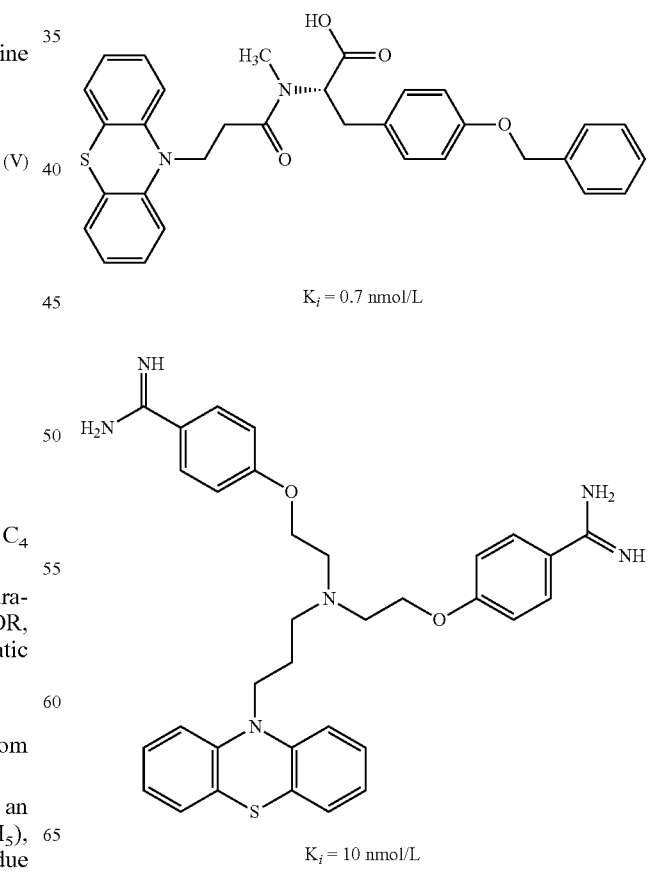

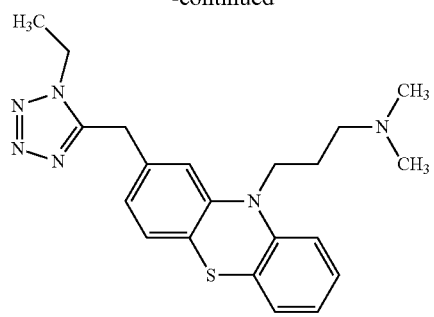

$K_i = 70$ nmol/L

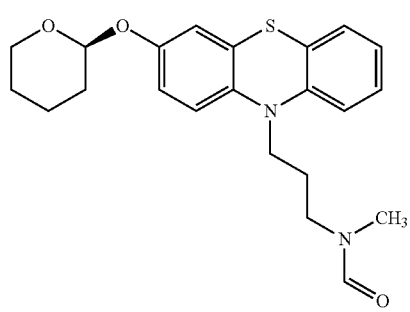

$K_i = 60$ nmol/L

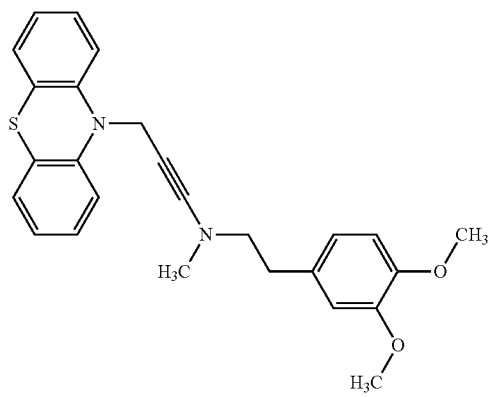

$K_i = 50$ nmol/L

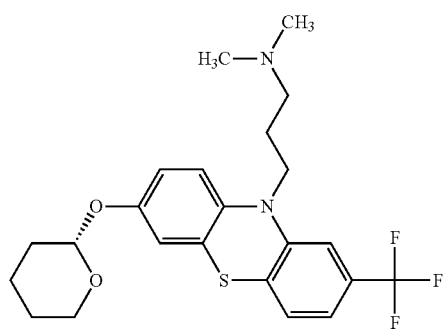

$K_i = 700$ nmol/L

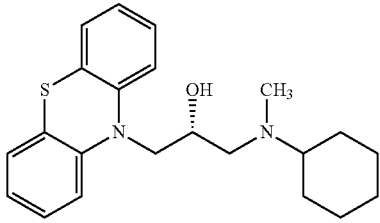

$K_i = 100$ nmol/L

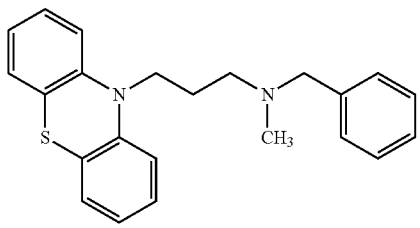

$K_i = 20$ nmol/L

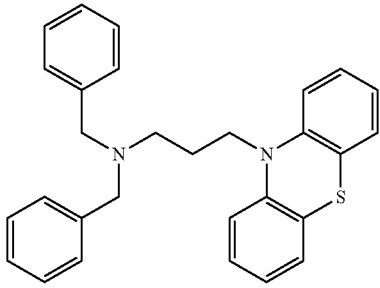

$K_i = 10$ nmol/L

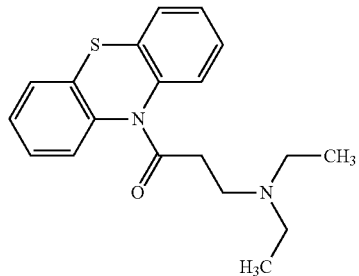

$K_i = 700$ nmol/L

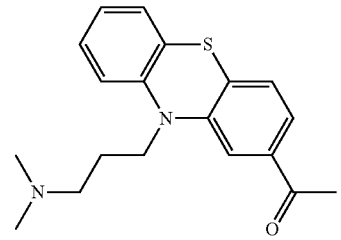

$K_i = 20$ μmol/L

Phenothiazine derivatives according to general formula (V) are employed in pharmacy in a known manner as antipsychotics, preferably in a concentration of 1.0 to 3.0 mg per kg body weight of an organism.

Depending on the type of carcinoma to be treated, the combination of a purine derivative according to general formula (I) or (II) and/or a thymine derivative of general formula (VI), (VI'), (VII) or (VIII) and a phenothiazine derivative according to general formula (V) can advantageously lead to superadditive ("synergistic") effects in the selective inhibition of the HSP27 protein. Thus, for example, the following effects are possible, which go beyond the effects that would actually be expected: reduced administration concentration and/or extended spectrum of activity and/or increased efficacy of the individual compounds (i.e. active ingredients) and pharmaceutical formulations. In a preferred embodiment of the present invention, the pharmaceutical formulation according to the invention accordingly comprises the purine derivative according to general formula (I) or (II) and/or the thymine derivative of general formula (VI), (VI'), (VII) or (VIII) in combination with one or more phenothiazine derivatives according to general formula (V).

Chlorpromazine displayed only a low affinity for interaction with HSP27 in wet-chemical experiments and is therefore less preferred as a representative of the phenothiazine derivatives of general formula (V) for use according to the invention in cancer therapy or the treatment of mucoviscidosis.

According to a preferred embodiment of the present invention, phenothiazine derivatives of general formula (V) are used individually or as a mixture thereof as medicinal products for use in cancer therapy or the treatment of mucoviscidosis.

A subject of the invention is therefore also the use of the phenothiazine derivatives of general formula (V) or of a mixture of this type for the preparation of a pharmaceutical formulation for use in cancer therapy or the treatment of mucoviscidosis.

Preferably, the phenothiazine derivatives of general formula (V) are administered in a quantity of 0.1 to 50 mg/kg, preferably about 0.1 to 30 mg/kg body weight per day and ideally in a quantity of 0.5 to 20 mg/kg, particularly preferably 0.5 to 15 mg/kg or 0.3 µmol/kg to 150 µmol/kg and ideally 1.5 µmol/kg to 60 µmol/kg body weight per day. A person skilled in the art will recognize that, if another compound is employed, e.g. in combination with a purine derivative of general formula (I) or (II) and/or a thymine derivative of general formula (VI), (VI'), (VII) or (VIII), the correct dosage can be determined both by investigating the efficacy of the compound in cell proliferation assays and by establishing the toxicity in animal experiments (and ultimately in humans).

Furthermore, a method for reducing the functionality of the HSP27 protein in a cell or organism is also covered by the present invention, comprising the administration of a purine derivative according to general formula (I) or (II) or a thymine derivative of general formula (VI), (VI'), (VII) or (VIII) in a physiologically effective concentration for the inhibition of the HSP27 protein, wherein the purine derivative interacts with the active ingredient binding pocket of the HSP27 protein.

The invention also comprises the use of a purine derivative according to general formula (I), (II) or a thymine derivative of general formula (VI), (VI'), (VII) or (VIII) and/or phenothiazine derivatives of general formula (V) for the treatment of disease states which are associated with increased HSP27 signalling, in particular in cancer and also in mucoviscidosis.

The invention also comprises a method for the treatment of mucoviscidosis or avoidance of the development of chemoresistance in cancer therapy by administration of an effective dose of an HSP27 inhibitor, in particular of a purine derivative according to general formula (I), (II) or of a thymine derivative of general formula (VI) or (VII) (VI), (VI'), (VII) or (VIII) and/or phenothiazine derivatives of general formula (V).

The treatment method here comprises the administration of a pharmaceutical formulation containing at least a purine derivative according to general formula (I), (II), a thymine derivative of formula (VI), (VI'), (VII) or (VIII) and/or a phenothiazine derivative of general formula (V) in a physiologically effective concentration. According to a preferred embodiment of the invention, in particular for the avoidance of the development of chemoresistance in cancer therapy and for the treatment of mucoviscidosis, the pharmaceutical formulation for administration is solid or liquid, e.g. in the form of a tablet, capsule or liquid or rectally in the form of suppositories, so that the pharmaceutical formulation is administered to an organism by oral or parenteral administration and resorbed via the mucous membranes.

Preferably, the purine derivatives according to general formula (I), (II), thymine derivatives of formula (VI), (VI'), (VII) or (VIII) and/or a phenothiazine derivative of general formula (V) are administered in a quantity of about 0.1 to 30 mg/kg body weight per day and ideally in a quantity of 0.5 to 15 mg/kg body weight per day. Preferred are doses of 0.1 to 500 µmol, in particular 0.5 to 200 µmol, particularly preferably 1 to 50 µmol per kg body weight per day. Suitable organisms for such treatment are e.g. mammals, such as humans. Preferably, the purine derivatives according to general formula (I), (II), thymine derivatives of formula (VI), (VI'), (VII) or (VIII) and/or a phenothiazine derivatives of general formula (V) are employed in non-cytotoxic concentrations.

A subject of the invention are also purine derivatives according to general formula (I) and/or (II), of a thymine derivative of formula (VI), (VI'), (VII) or (VIII) and/or of a phenothiazine derivative of general formula (V) or of a mixture for use as medicinal products, in particular for use in cancer therapy or the treatment of mucoviscidosis.

According to a preferred embodiment of the present invention, therefore, the purine derivatives according to general formula (I) and/or (II), thymine derivatives of formula (VI), (VI'), (VII) or (VIII) and/or phenothiazine derivatives of general formula (V) or of a mixture are used for the preparation of a pharmaceutical formulation, in particular for use in cancer therapy or the treatment of mucoviscidosis.

The dosage of the phenothiazine derivatives of general formula (V) and/or the purine derivatives of general formula (I) or (II) and/or the thymine derivatives of formula (VI), (VI'), (VII) or (VIII) depends on various factors, e.g. the administration method, age, weight and health, including the type of the organism to be treated.

Typical examples of purine derivatives according to general formula (I) or (II) (with the respective calculated inhibitory concentration in relation to HSP27—$K_i$) are:

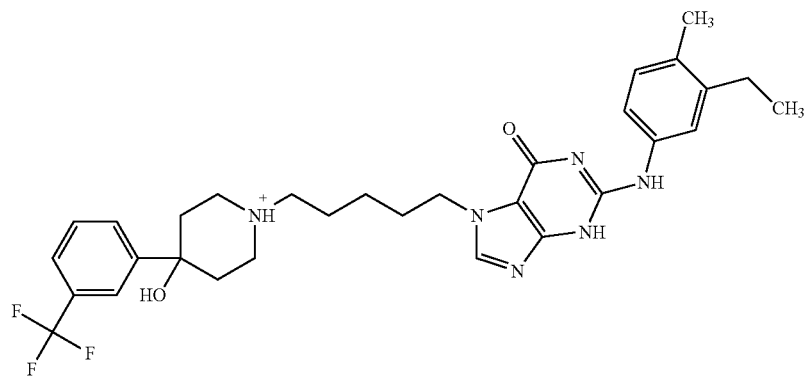
$K_i$ = 80 nmol/L
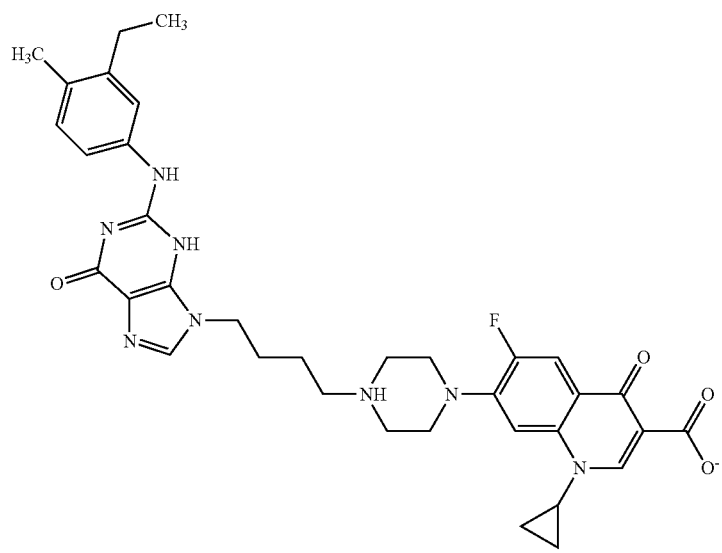
$K_i$ = 100 nmol/L
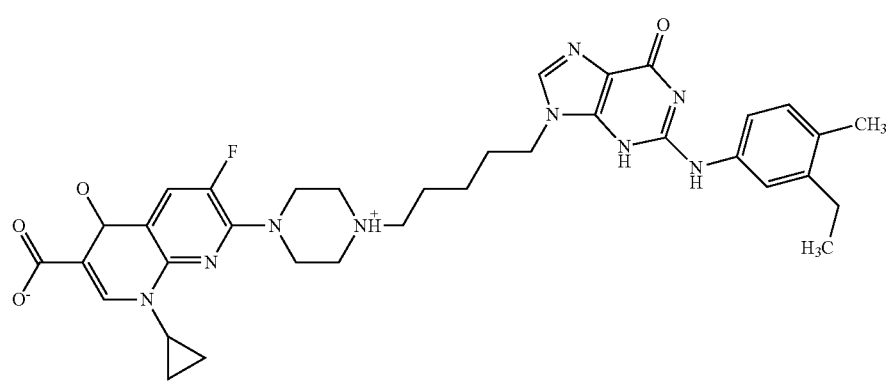
$K_i$ = 30 nmol/L

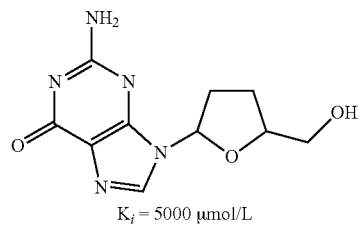
$K_i$ = 5000 µmol/L
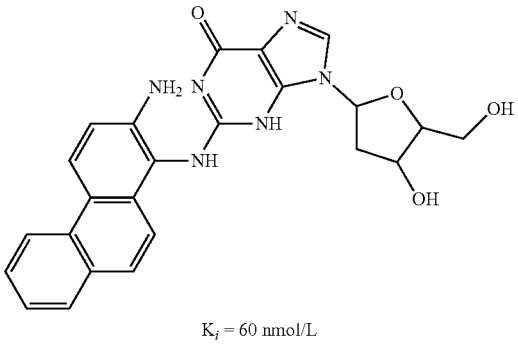
$K_i$ = 60 nmol/L
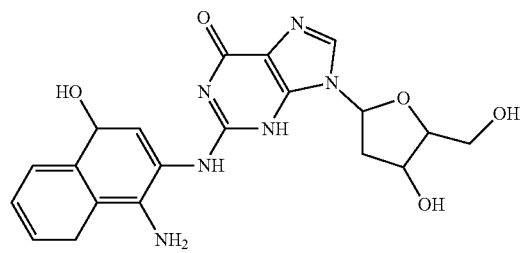
$K_i$ = 60 nmol/L
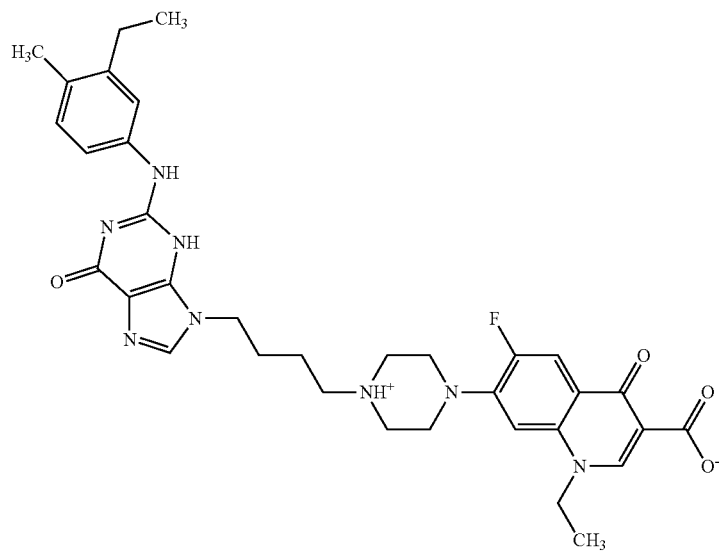
$K_i$ = 80 nmol/L
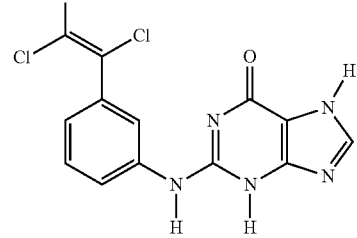
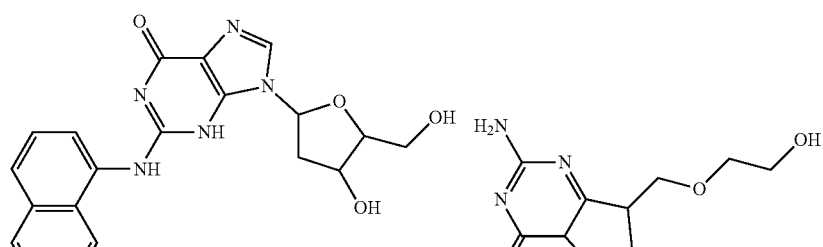
$K_i$ = 50 nmol/L
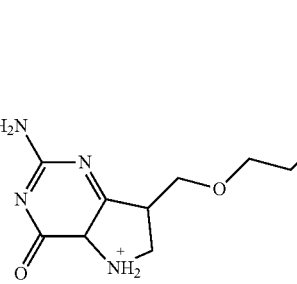
$K_i$ = 100 mmol/L

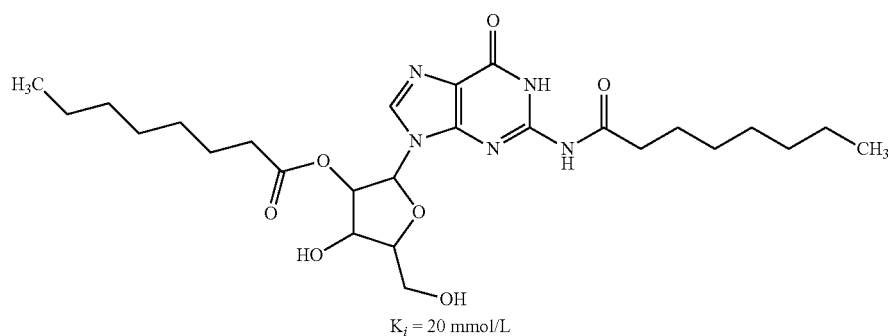
$K_i$ = 20 mmol/L
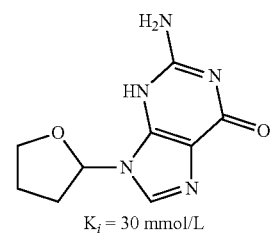
$K_i$ = 30 mmol/L
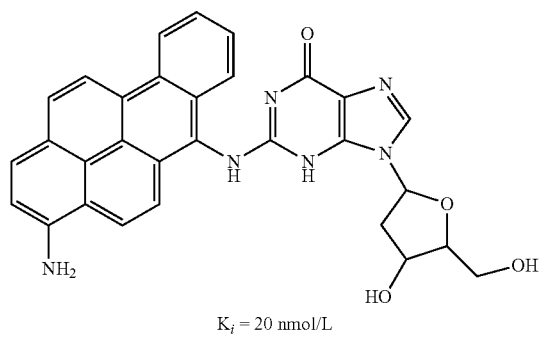
$K_i$ = 20 nmol/L
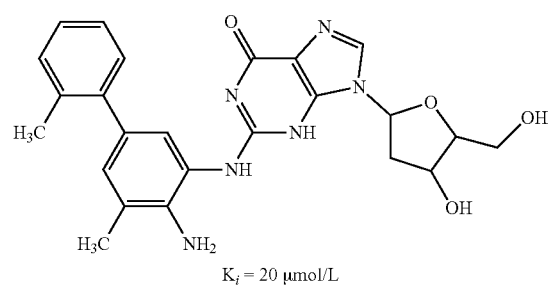
$K_i$ = 20 μmol/L
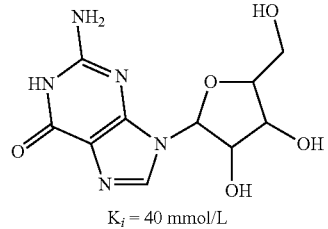
$K_i$ = 40 mmol/L
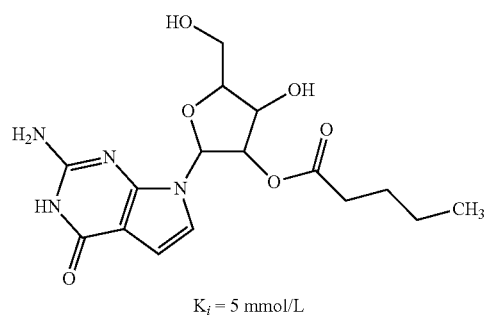
$K_i$ = 5 mmol/L
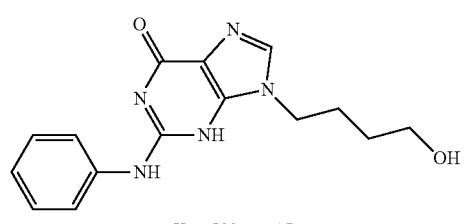
$K_i$ = 500 nmol/L
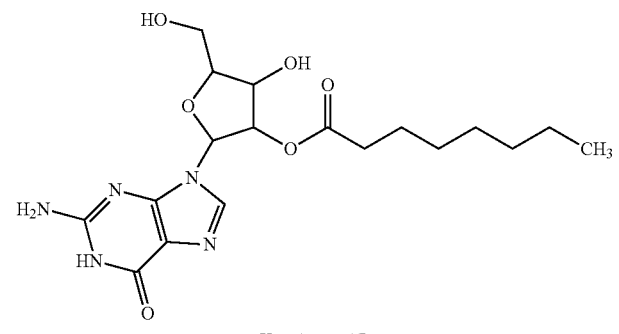
$K_i$ = 1 mmol/L
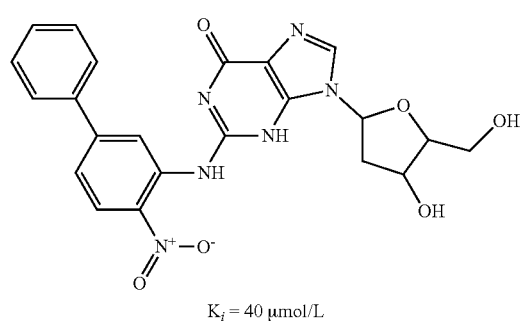
$K_i$ = 40 μmol/L
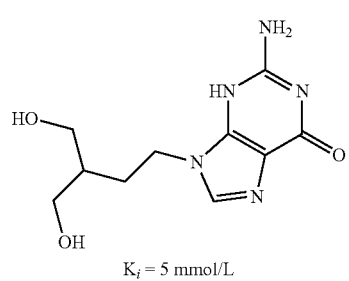
$K_i$ = 5 mmol/L

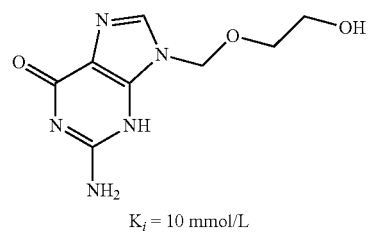
$K_i$ = 10 mmol/L
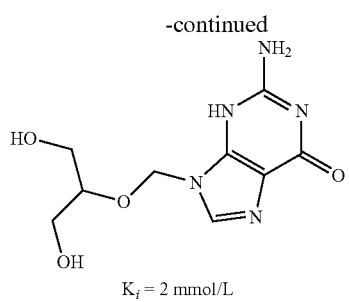
$K_i$ = 2 mmol/L
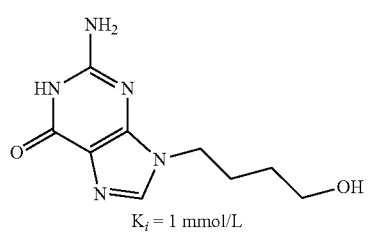
$K_i$ = 1 mmol/L
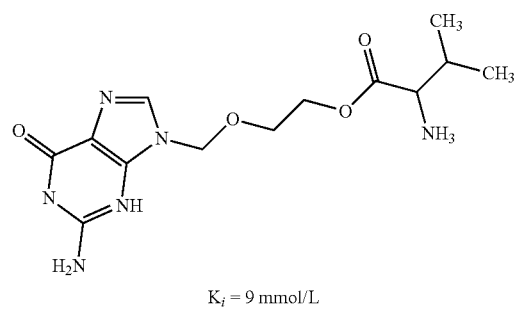
$K_i$ = 9 mmol/L
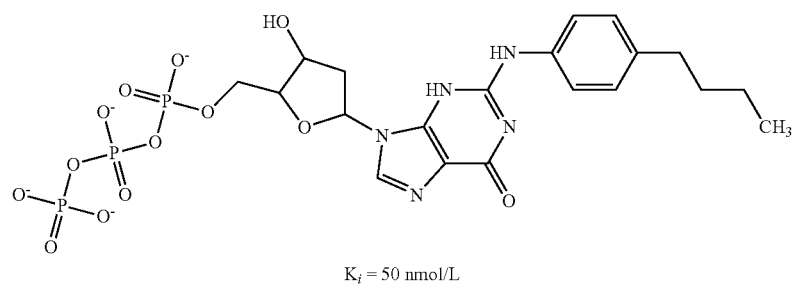
$K_i$ = 50 nmol/L
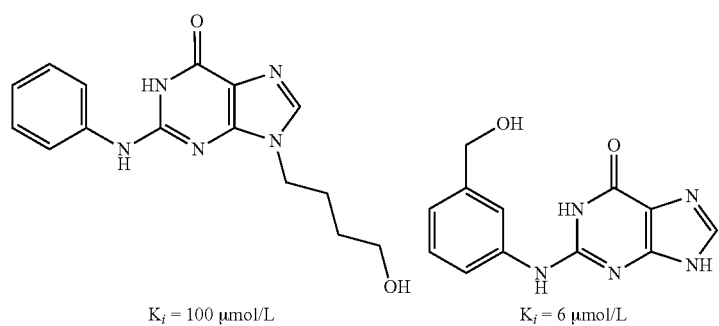
$K_i$ = 100 μmol/L    $K_i$ = 6 μmol/L
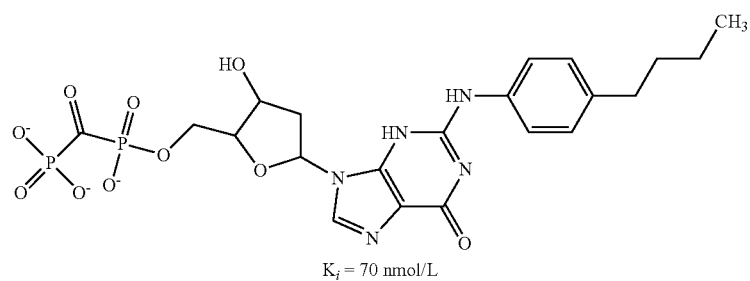
$K_i$ = 70 nmol/L

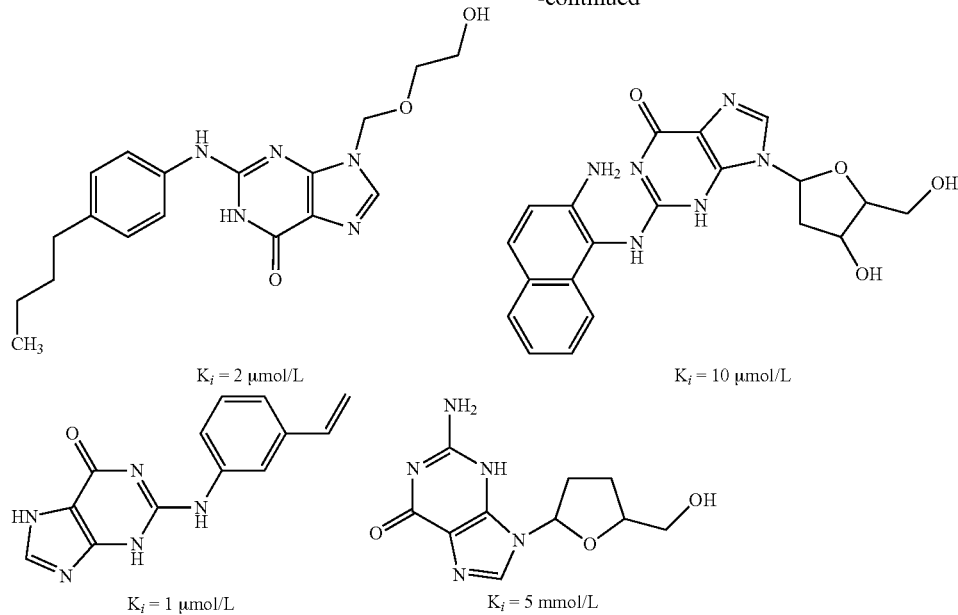

The compounds with the lowest possible $K_i$ are particularly preferred. Preferred are the compounds with a $K_i$ of no more than 100 μmol/L, in particular no more than 10 μmol/L, particularly preferably no more than 500 nmol/L.

Typical examples of thymine derivatives according to general formula (VI), (VI'), (VII) or (VIII): (with the respective calculated inhibitory concentration in relation to HSP27—$K_i$):

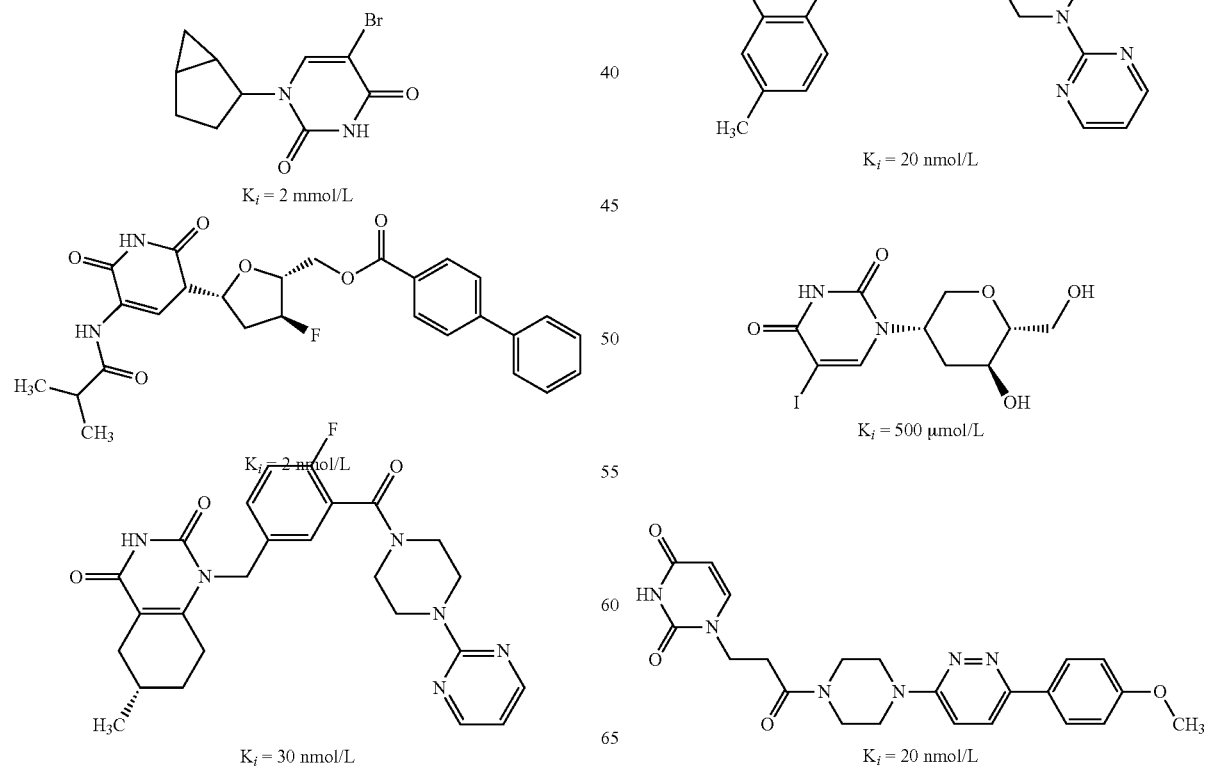

31
-continued
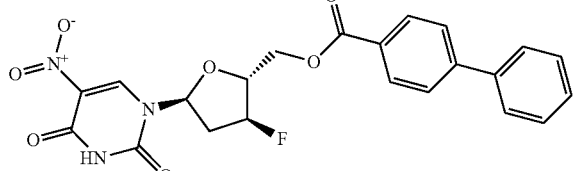
$K_i$ = 7 nmol/L
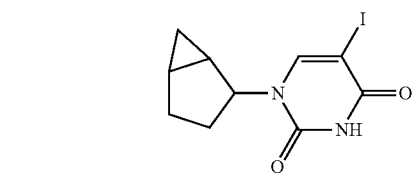
$K_i$ = 400 μmol/L
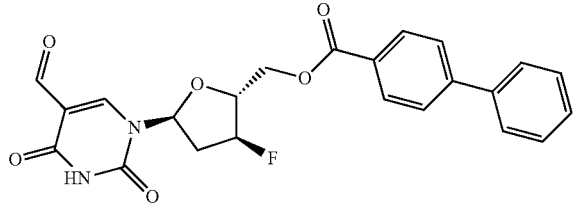
$K_i$ = 20 nmol/L
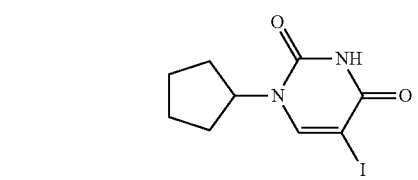
$K_i$ = 300 μmol/L
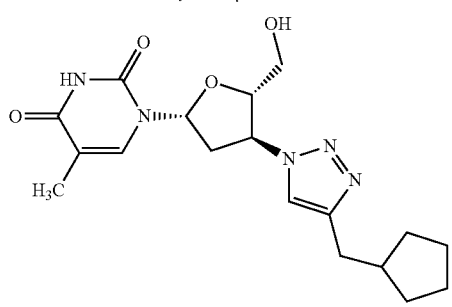
$K_i$ = 20 nmol/L
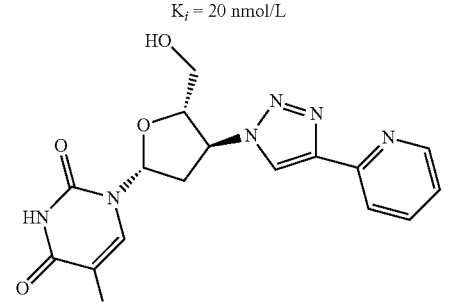
$K_i$ = 500 nmol/L
32
-continued
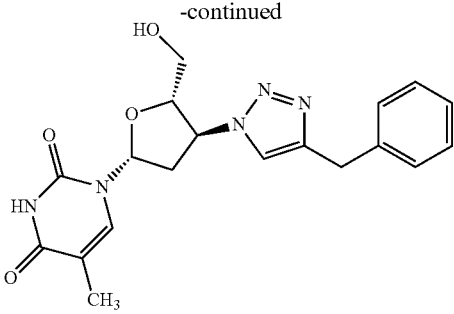
$K_i$ = 20 μmol/L
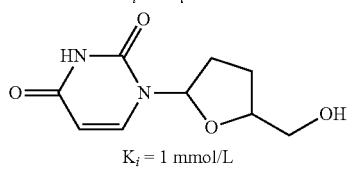
$K_i$ = 1 mmol/L
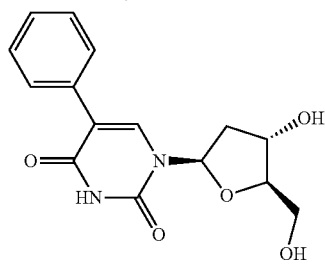
$K_i$ = 400 μmol/L
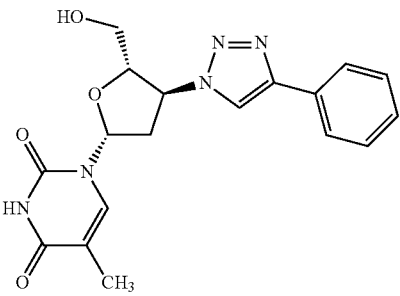
$K_i$ = 30 μmol/L
$K_i$ = 10 μmol/L
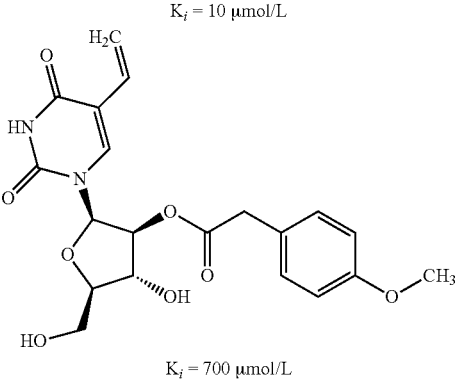
$K_i$ = 700 μmol/L 33
-continued
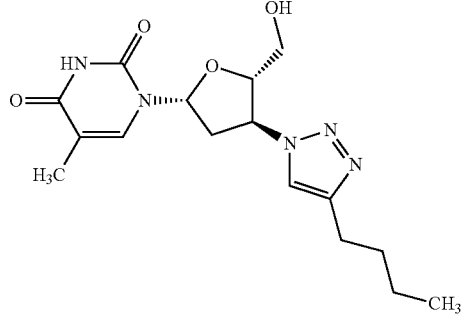
$K_i$ = 30 µmol/L
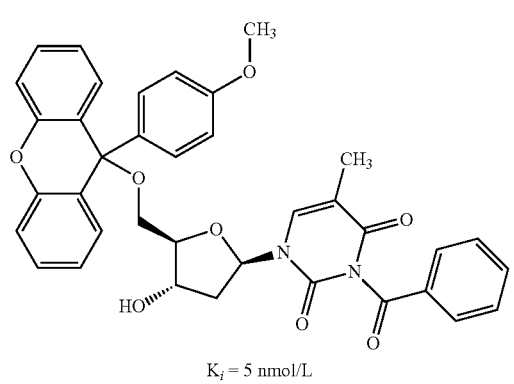
$K_i$ = 5 nmol/L
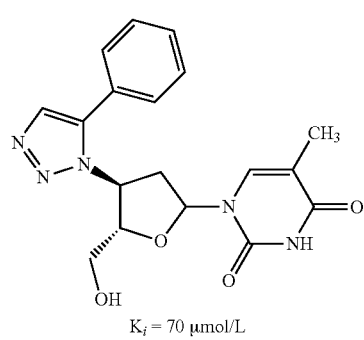
$K_i$ = 70 µmol/L
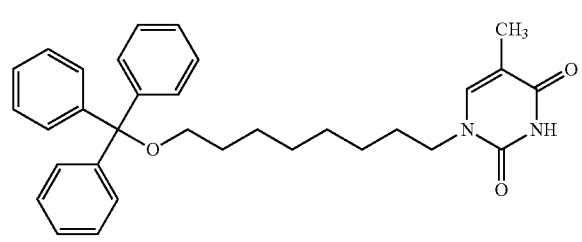
$K_i$ = 100 µmol/L
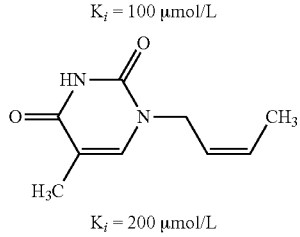
$K_i$ = 200 µmol/L
34
-continued
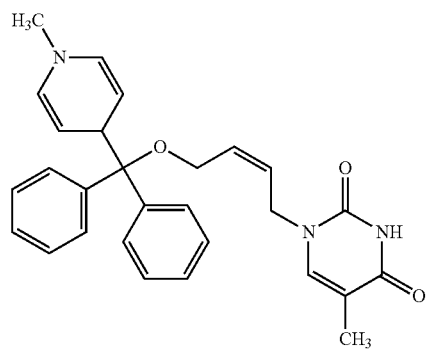
$K_i$ = 300 nmol/L
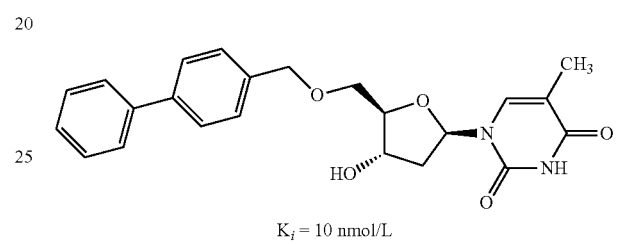
$K_i$ = 10 nmol/L
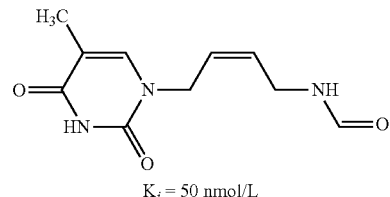
$K_i$ = 50 nmol/L
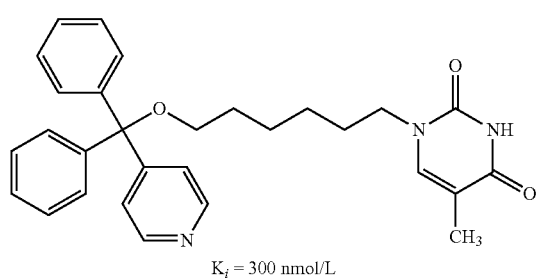
$K_i$ = 300 nmol/L
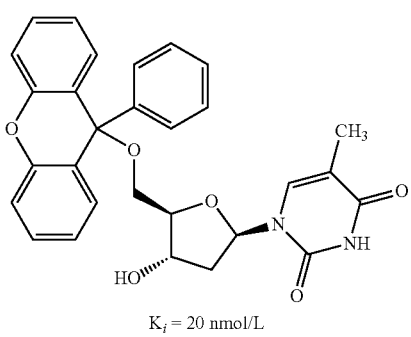
$K_i$ = 20 nmol/L -continued
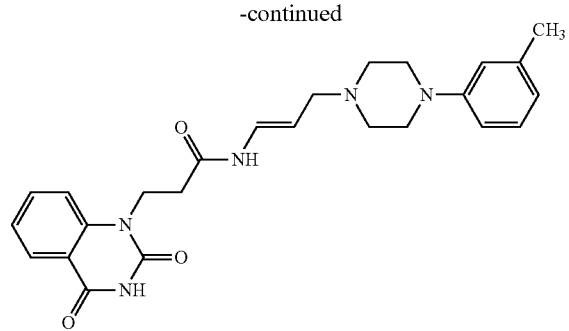
$K_i$ = 10 nmol/L
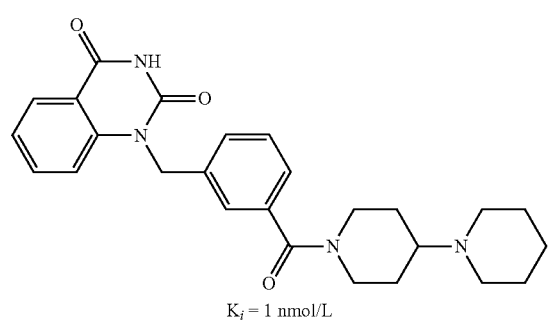
$K_i$ = 1 nmol/L
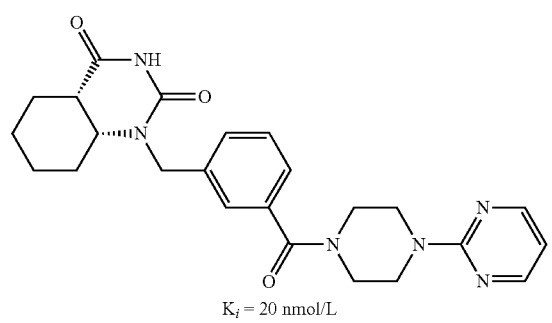
$K_i$ = 20 nmol/L
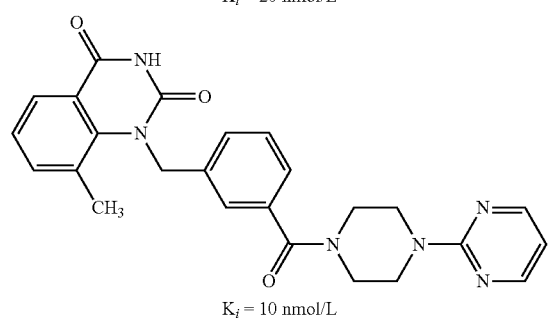
$K_i$ = 10 nmol/L
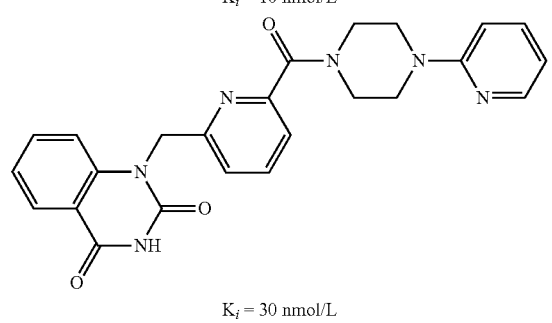
$K_i$ = 30 nmol/L
-continued
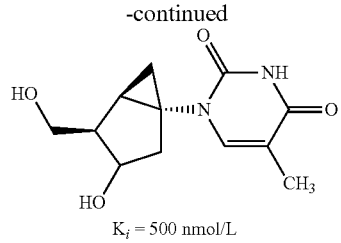
$K_i$ = 500 nmol/L
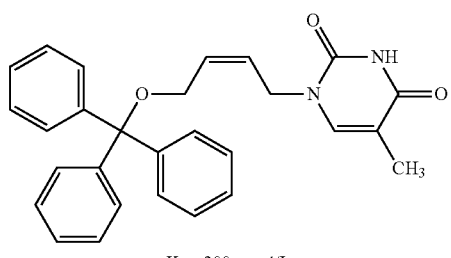
$K_i$ = 200 nmol/L
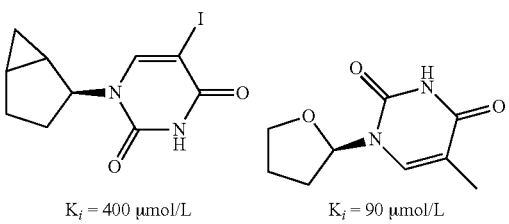 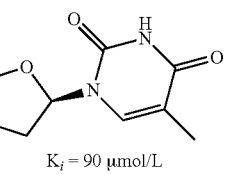
$K_i$ = 400 µmol/L    $K_i$ = 90 µmol/L
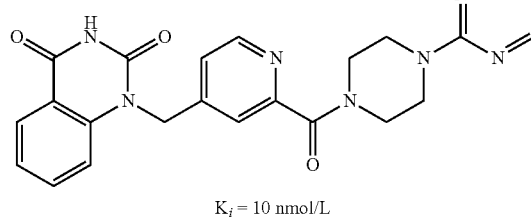
$K_i$ = 10 nmol/L
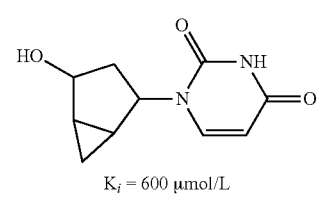
$K_i$ = 600 µmol/L
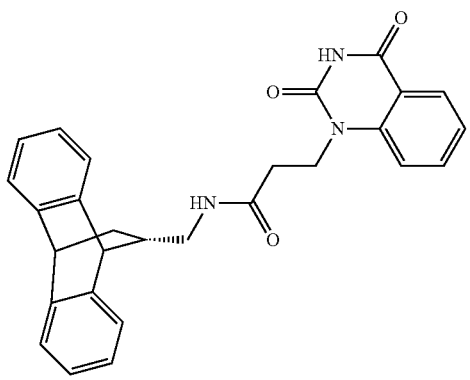
$K_i$ = 20 nmol/L 37
-continued
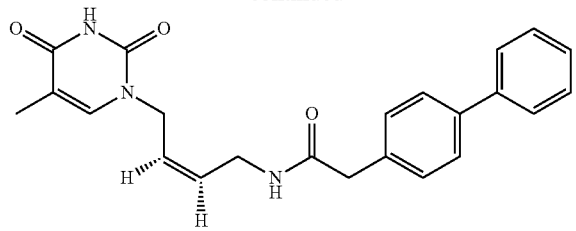
K_i = 40 nmol/L
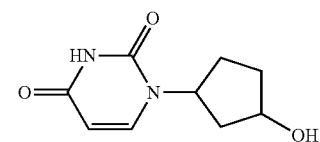
K_i = 400 µmol/L
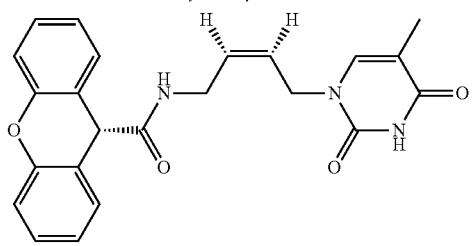
K_i = 200 nmol/L
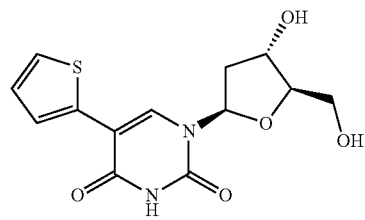
K_i = 200 µmol/L
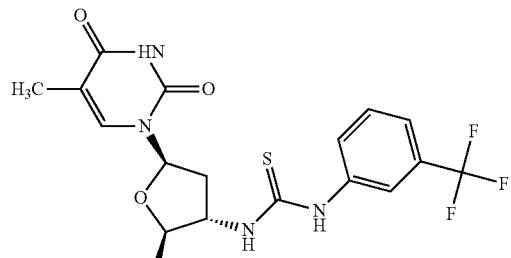
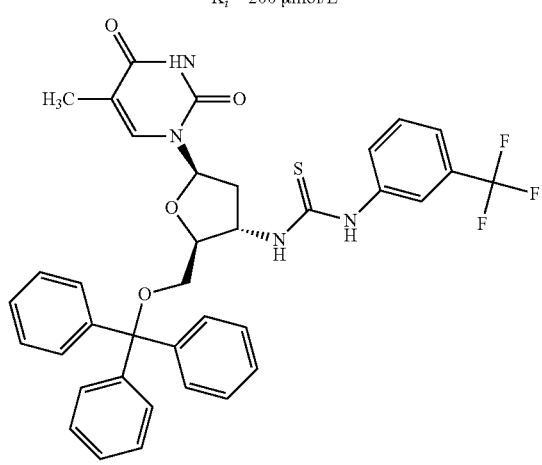
K_i = 700 µmol/L
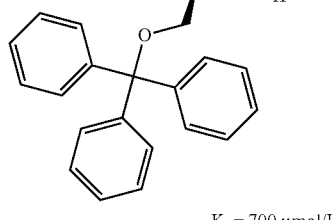
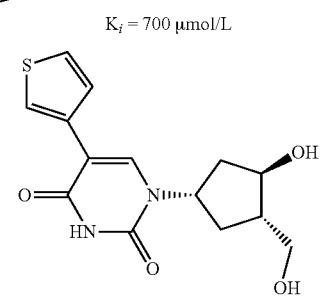
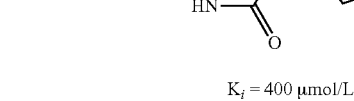
K_i = 400 µmol/L
38
-continued
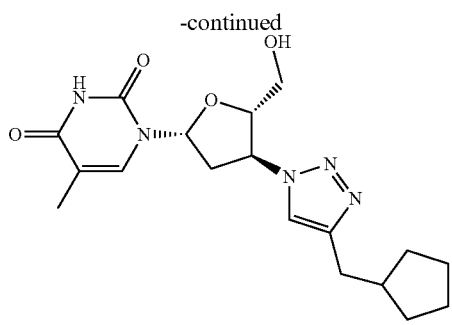
K_i = 10 µmol/L
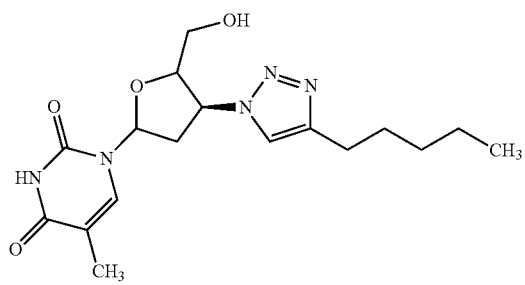
K_i = 100 µmol/L
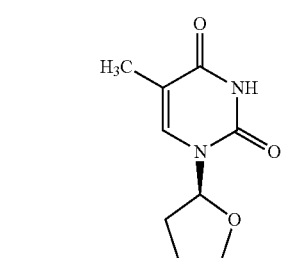
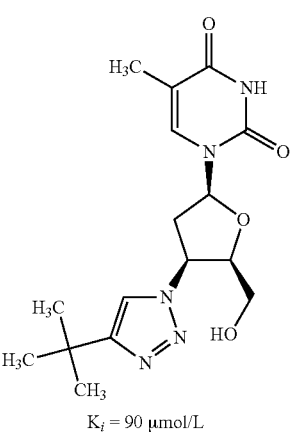
K_i = 90 µmol/L
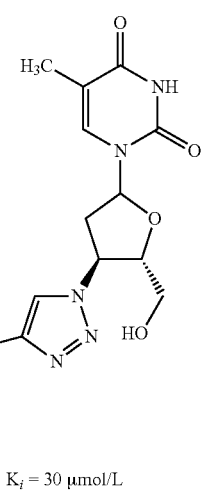
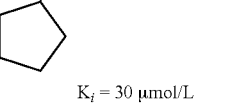
K_i = 30 µmol/L -continued
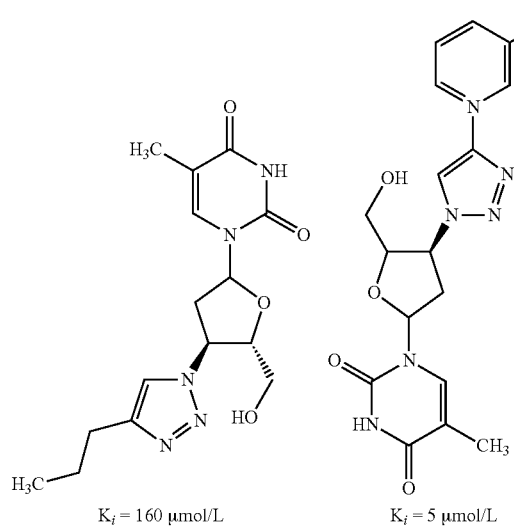
$K_i$ = 160 μmol/L
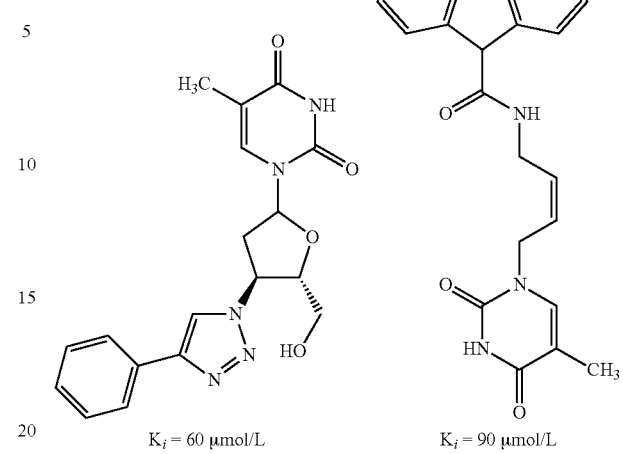
$K_i$ = 5 μmol/L
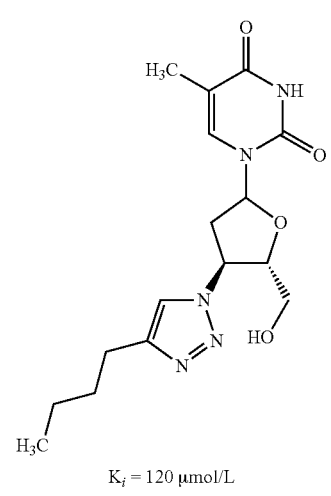
$K_i$ = 120 μmol/L
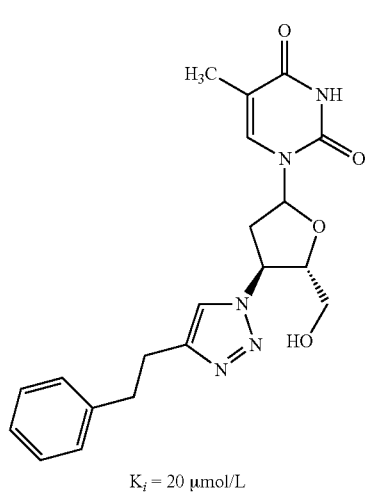
$K_i$ = 20 μmol/L
-continued
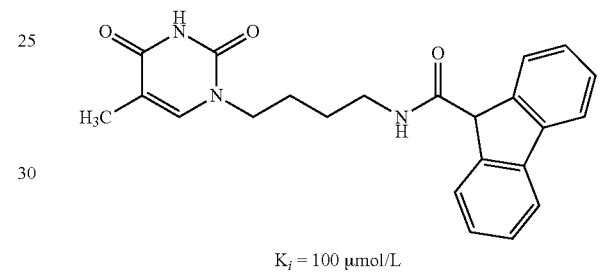
$K_i$ = 60 μmol/L    $K_i$ = 90 μmol/L
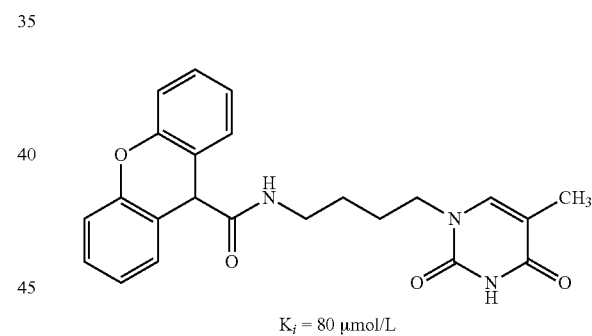
$K_i$ = 100 μmol/L
$K_i$ = 80 μmol/L
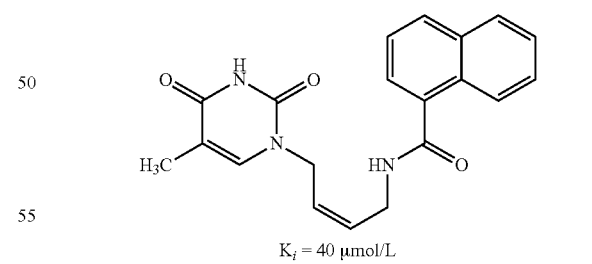
$K_i$ = 40 μmol/L
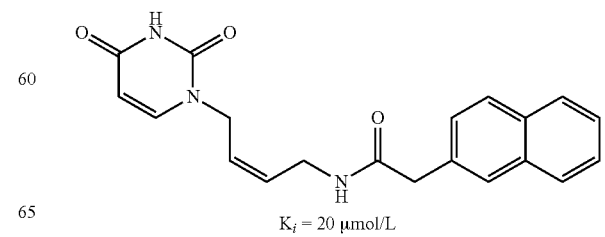
$K_i$ = 20 μmol/L

41
-continued
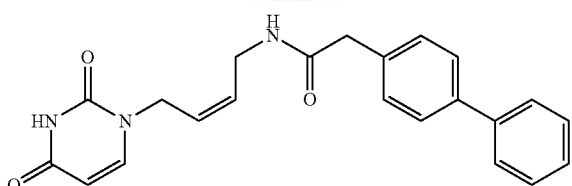
$K_i$ = 20 µmol/L
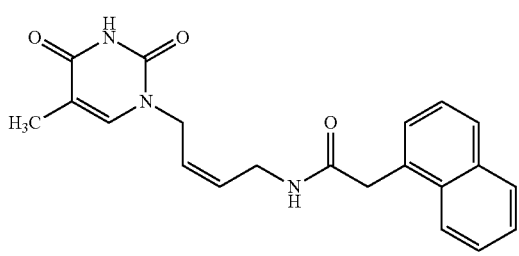
$K_i$ = 40 µmol/L
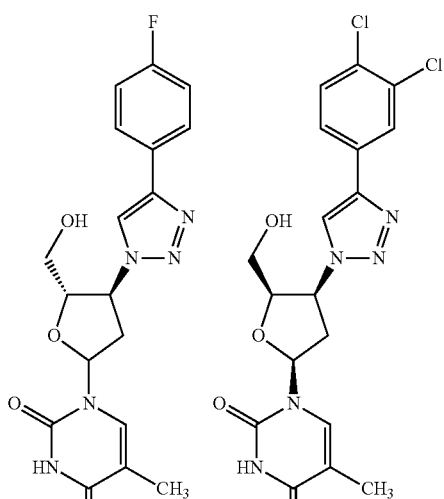
$K_i$ = 50 µmol/L        $K_i$ = 20 µmol/L
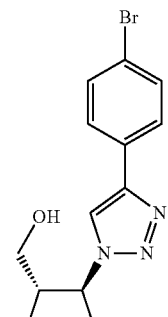
$K_i$ = 20 µmol/L
42
-continued
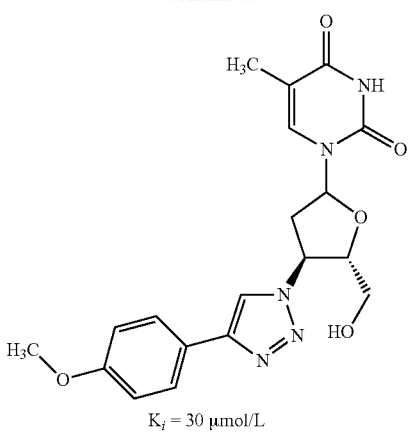
$K_i$ = 30 µmol/L
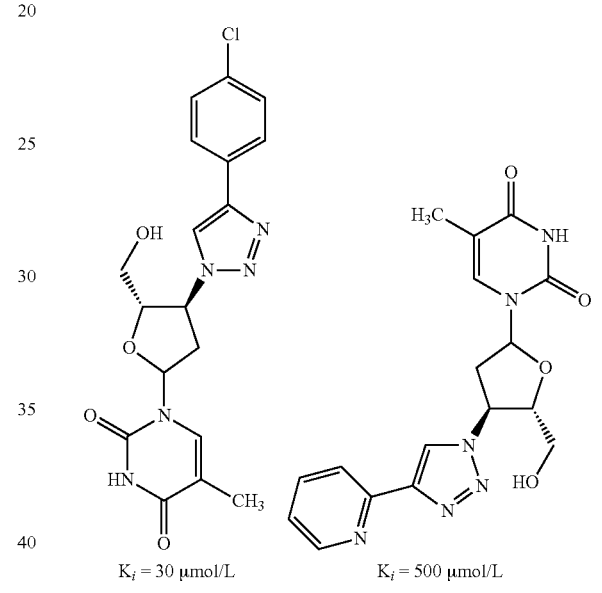
$K_i$ = 30 µmol/L        $K_i$ = 500 µmol/L
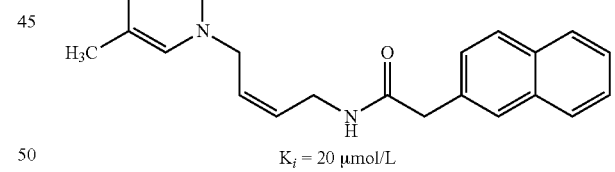
$K_i$ = 20 µmol/L
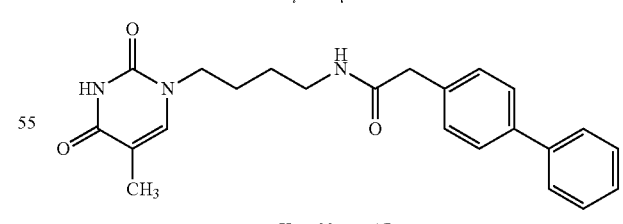
$K_i$ = 20 µmol/L
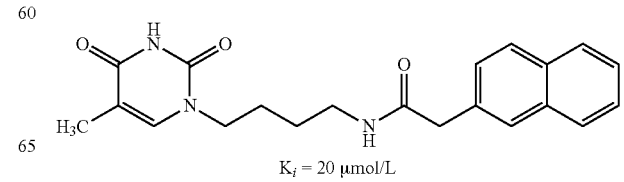
$K_i$ = 20 µmol/L

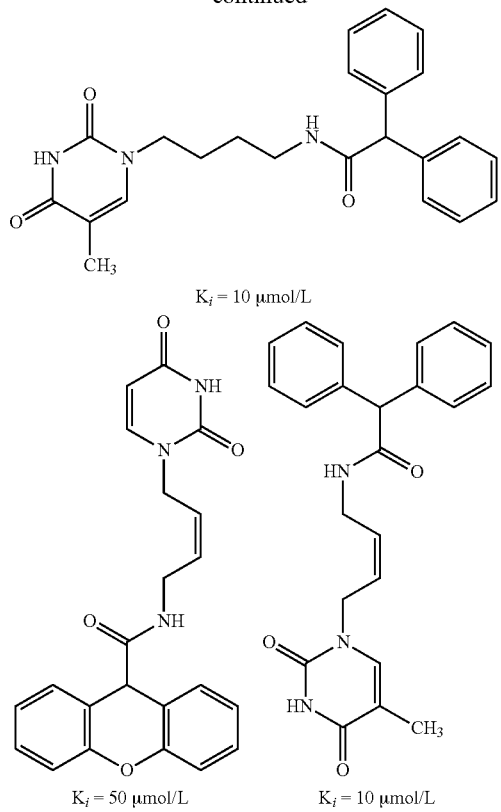

$K_i$ = 10 μmol/L $K_i$ = 50 μmol/L   $K_i$ = 10 μmol/L

The compounds with the lowest possible $K_i$ are particularly preferred. Preferred are the compounds with a $K_i$ of no more than 100 μmol/L, in particular no more than 10 μmol/L, particularly preferably no more than 500 nmol/L.

The present invention also comprises the use of a purine derivative according to general formula (I) and/or (II), a thymine derivative of formula (VI), (VI'), (VII) or (VIII) and/or a phenothiazine derivative of general formula (V) for the preparation of a pharmaceutical formulation, in particular for use in cancer therapy or the treatment of mucoviscidosis.

A subject of the invention is also the use of a purine derivative according to general formula (I), (II), a thymine derivative of formula (VI), (VI'), (VII) or (VIII) and/or a phenothiazine derivative of general formula (V) in combination with chemotherapy, radiotherapy and/or cancer immunotherapy for use in the treatment of cancer diseases, wherein advantageously the development of resistance (i.e. ability of a tumour or tumour cells to resist the treatment method employed) to the treatment methods is reduced, in particular suppressed.

Traditional methods of treating cancer diseases are e.g. surgical tumour removal (resection), chemotherapy and radiotherapy, wherein often two or even all three treatment methods are used at the same time in an organism. In cancer immunotherapy methods, a distinction is made between active and passive immunisation. In the case of active immunisation, the patient is given substances which are intended to trigger an immune response in his/her immune system. In the case of passive immunisation, antibodies or antibody fragments are employed. In adoptive immunotherapy, leucocytes are taken from the patient, cultured ex vivo and then injected into the patient again. However, if all the cells of the tumour and its metastases are not destroyed during the treatment, the further treatment of cancer diseases is made significantly more difficult owing to the development of resistance.

A purine derivative according to general formula (I), (II), of a thymine derivative of formula (VI), (VI'), (VII) or (VIII) and/or of a phenothiazine derivative of general formula (V) therefore offers the particular advantage that the development of resistance in chemotherapy, radiotherapy or cancer immunotherapy, in particular cytostatic treatment, is prevented or at least significantly delayed. Examples of cytostatic agents are: folic acid antagonists (e.g. methotrexate, pemetrexed), pyrimidine analogs (e.g. 5-fluorouracil, gemcitabine), purine analogs (e.g. pentostatin, azathioprine) and oligopeptides with N- or C-terminal protection (e.g. bortezomib).

Preferably, at least one purine derivative according to general formula (I), (II), a thymine derivative of formula (VI), (VI'), (VII) or (VIII) and/or a phenothiazine derivative of general formula (V) is employed in combination with a cytostatic agent, which is preferably selected from the above-mentioned list, for the cancer therapy.

In a preferred therapy regimen, the purine derivative, thymine derivative and/or phenothiazine derivative is already employed before the start of the chemotherapy, radiotherapy and/or cancer immunotherapy and the administration of the purine derivative, thymine derivative and/or phenothiazine derivative is continued during the said cytotoxic therapies (chemotherapy, radiotherapy and/or cancer immunotherapy) in order to suppress the development of resistance. Preferably, the administration of the purine derivative, thymine derivative and/or phenothiazine derivative is started 15 min to 4 hours before the start of the cytotoxic therapy.

Further features and advantages of the invention can be taken from the following schematic drawings and embodiment examples with the aid of which the invention is intended to be explained in more detail by way of example without limiting the invention thereto.

Figure 2:
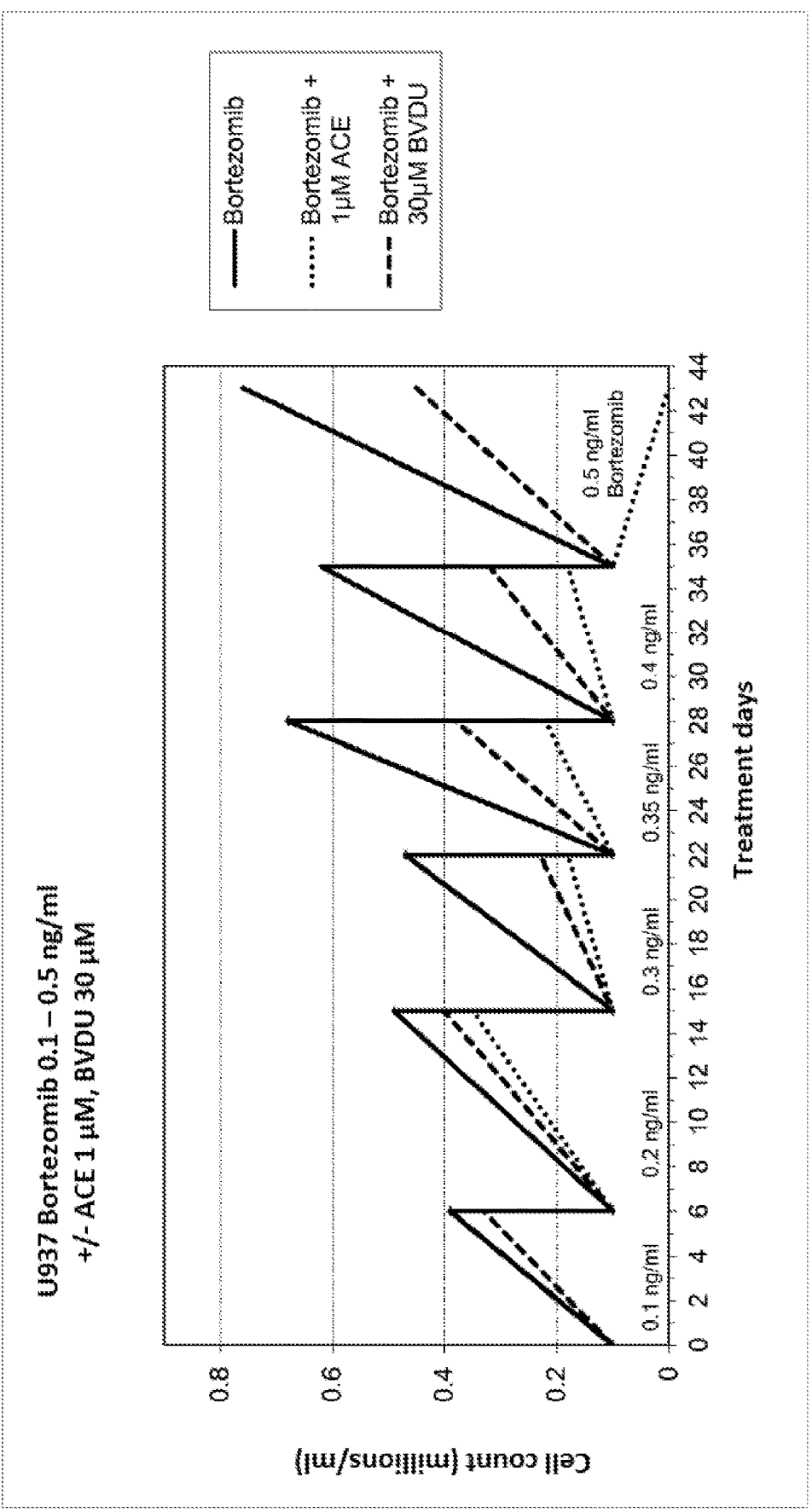

There are shown in:

FIG. 1: a spectrophotometric protein aggregation assay at 43° C., a wavelength of 500 nm and a concentrations of the proteins: 1.44 μmol/L citrate synthase (CS), 481 nmol/L HSP27 (HSP) in a 40 mmol/L HEPES buffer (pH 7.4) during treatment with 14 or 28 μmol/L 2-(3-trichlorovinylphenylamino)-1,9-dihydropurin-6-one (CS+HSP+test substance no. 2), with 750 μmol/L BVDU (CS+HSP+BVDU) and without (CS+HSP; reference);

FIG. 2: the cell counts over the number of treatment days of U937 cells treated with the cytostatic agent bortezomib (0.1 to 0.5 ng/ml) in each case combined with the HSP27 inhibitors acepromazine (+1 μM ACE) and BVDU (+30 μM BVDU) and without HSP27 inhibitor.

Figure 3:
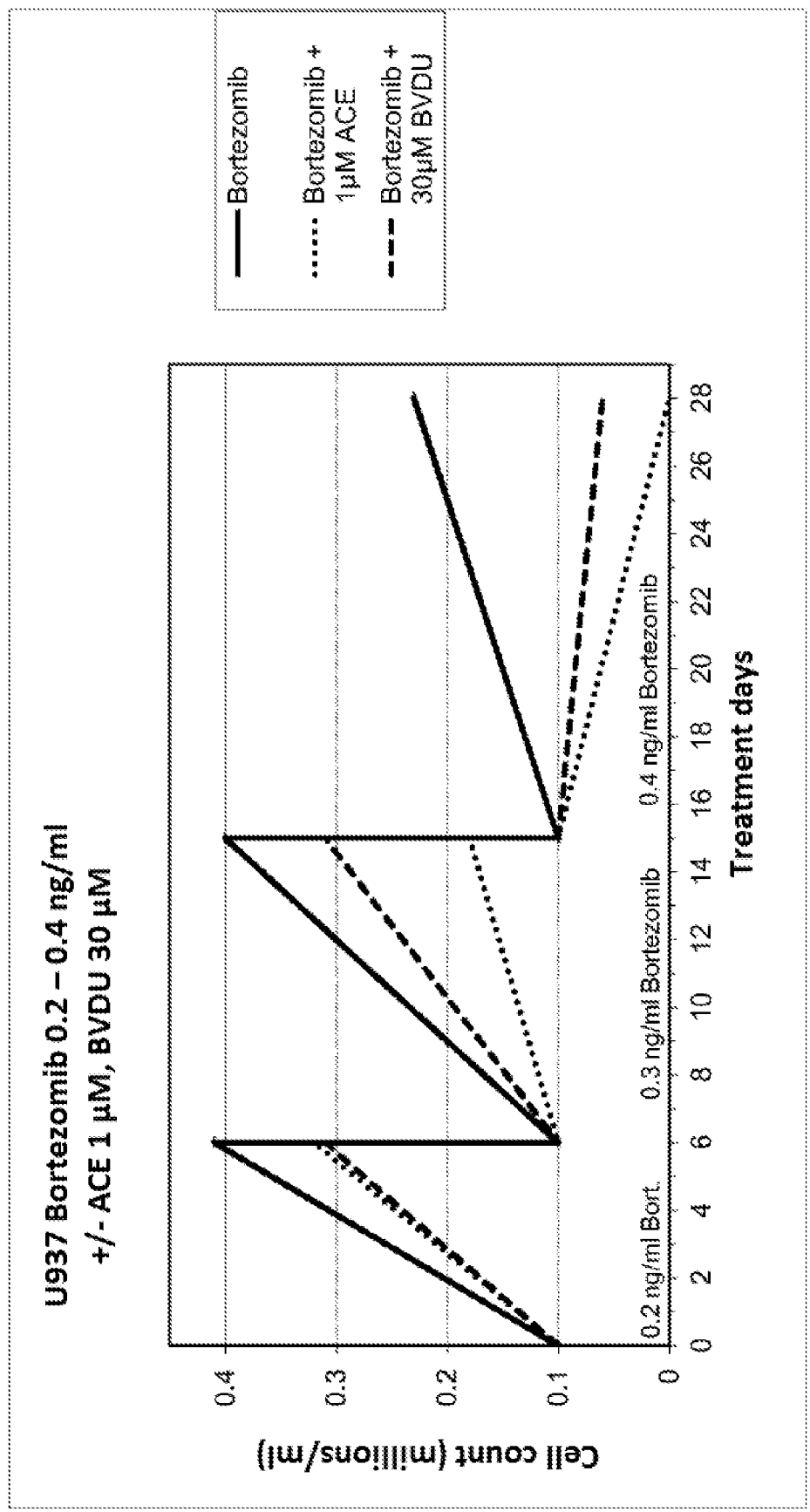

FIG. 3: the cell counts over the number of treatment days of U937 cells treated with the cytostatic agent bortezomib (0.2 to 0.4 ng/ml) in each case combined with the HSP27 inhibitors acepromazine (+1 μM ACE) and BVDU (+30 μM BVDU) and without HSP27 inhibitor.

Figure 4A:
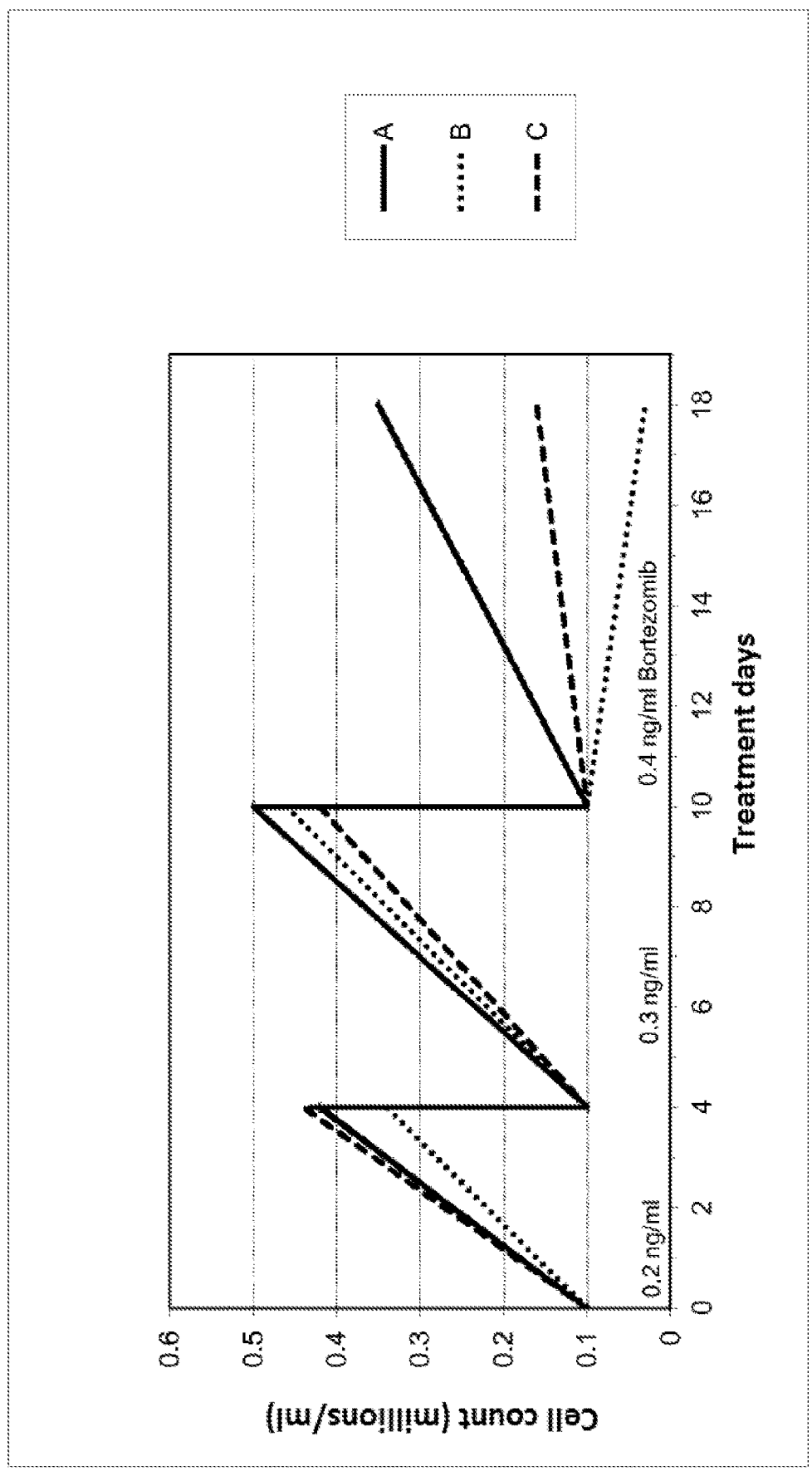
Figure 4B:
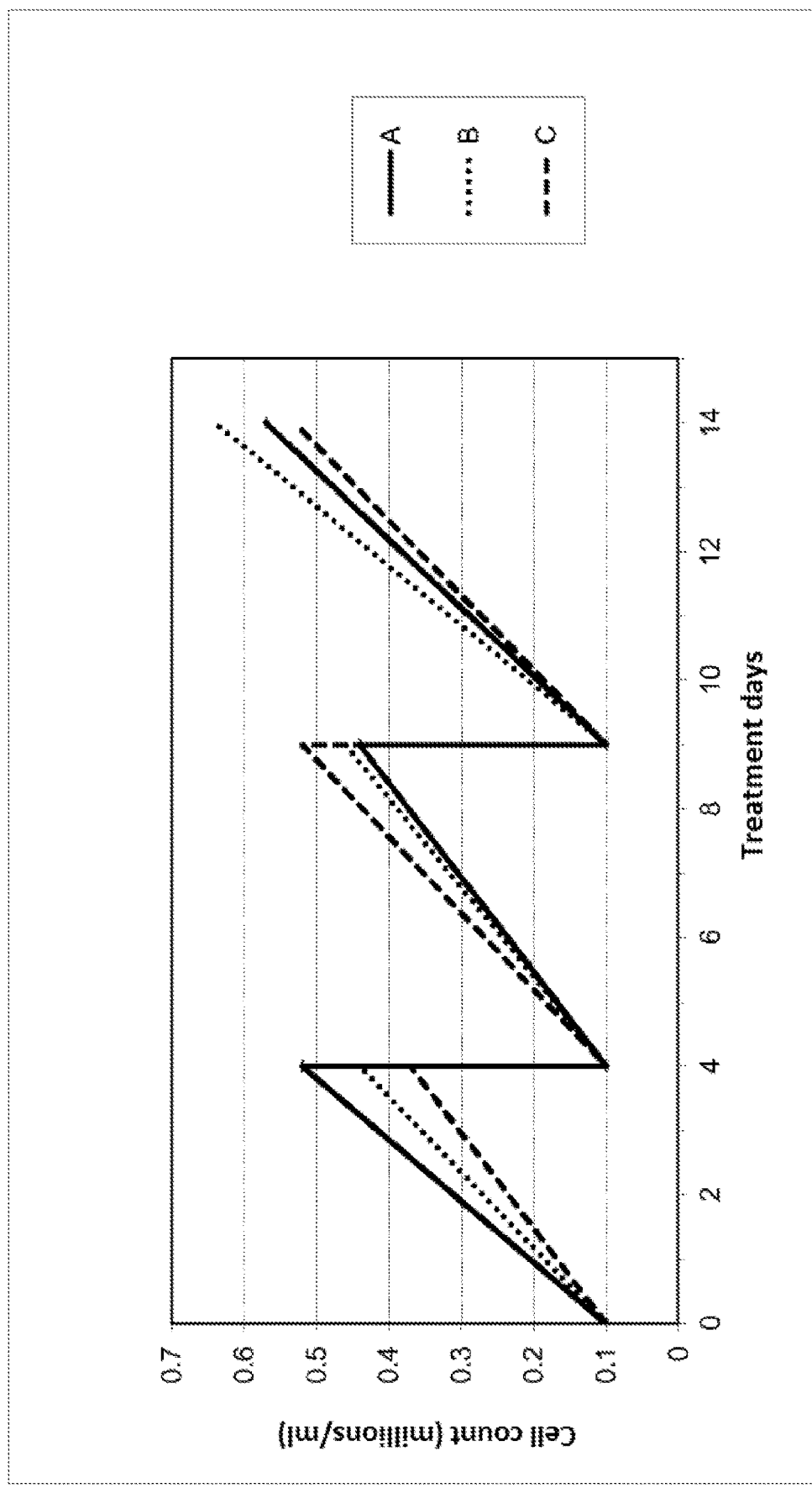

FIG. 4 shows the inhibition of the development of resistance of the tumour cell line RPMI-8226 by acepromazine. FIG. 4a shows RPMI 8226 cells treated with cytostatic agent bortezomib 0.2-0.4 ng/ml (A), combination treatment with bortezomib plus 0.75 μM acepromazine (B) and combination treatment with bortezomib plus 30 μM BVDU (C). FIG. 4b shows the control without cytostatic agent: RPMI 8226 cells untreated (A), 0.75 μM acepromazine alone (B) and 30 μM BVDU alone (C).

Figure 5A:
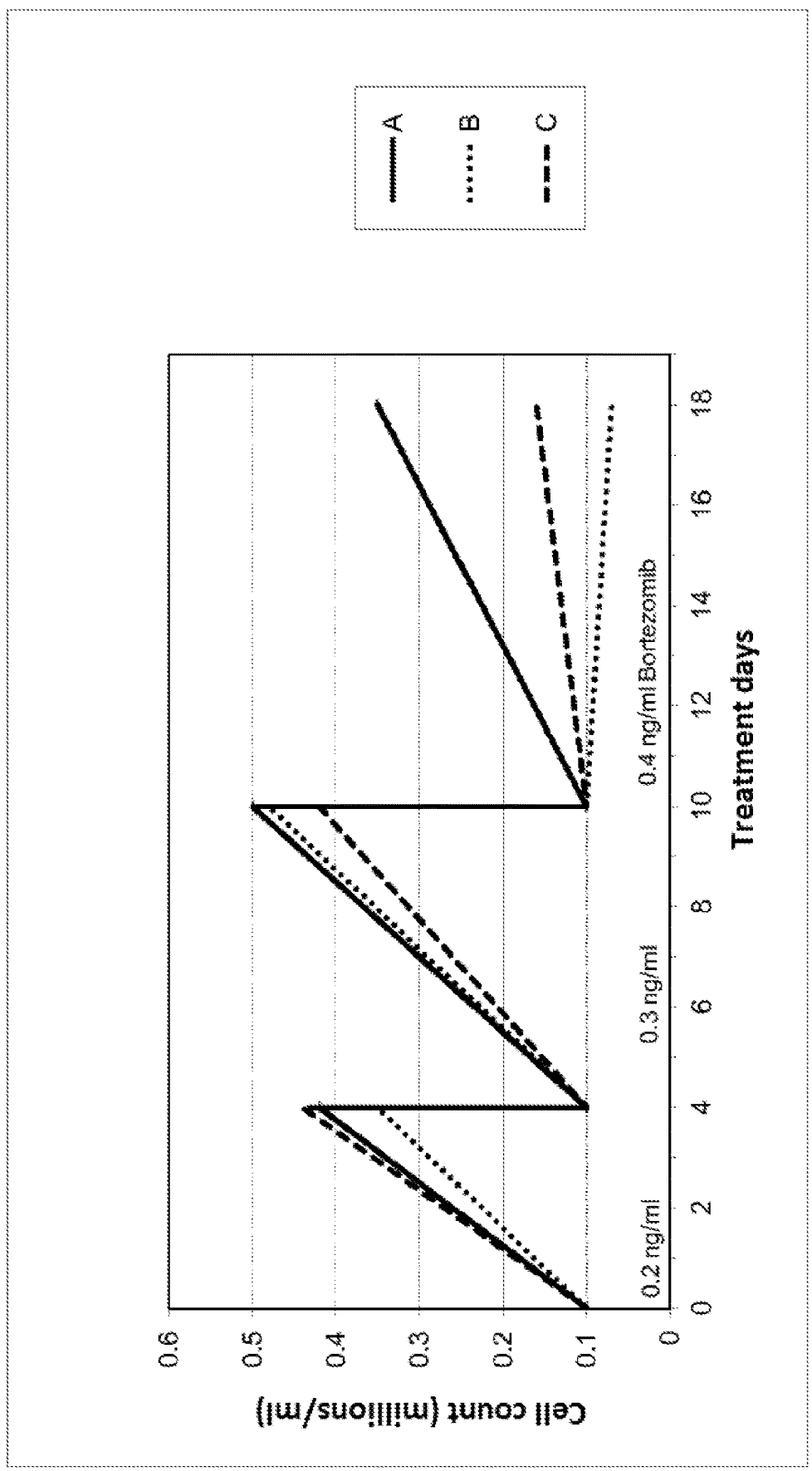
Figure 5B:
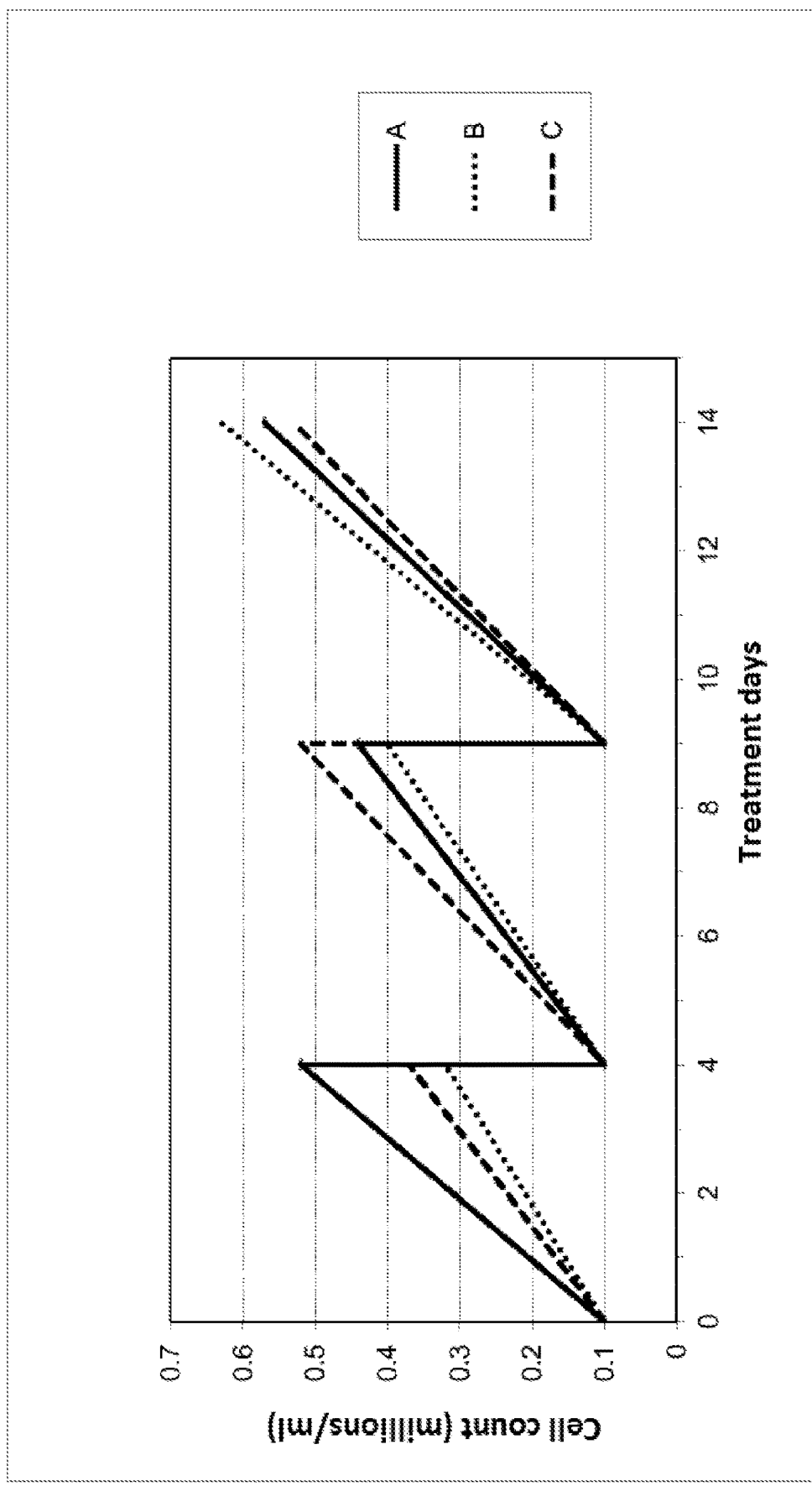

FIG. 5 shows the inhibition of the development of resistance of the tumour cell line RPMI-8226 by chlorpromazine. FIG. 5a shows RPMI 8226 cells treated with cytostatic agent bortezomib 0.2-0.4 ng/ml (A), combination treatment with bortezomib plus 0.5 µM chlorpromazine (B) and combination treatment with bortezomib plus 30 µM BVDU (C). FIG. 5b shows the control without cytostatic agent: RPMI 8226 cells untreated (A), 0.5 µM chlorpromazine alone (B) and 30 µM BVDU alone (C).

Figure 6A:
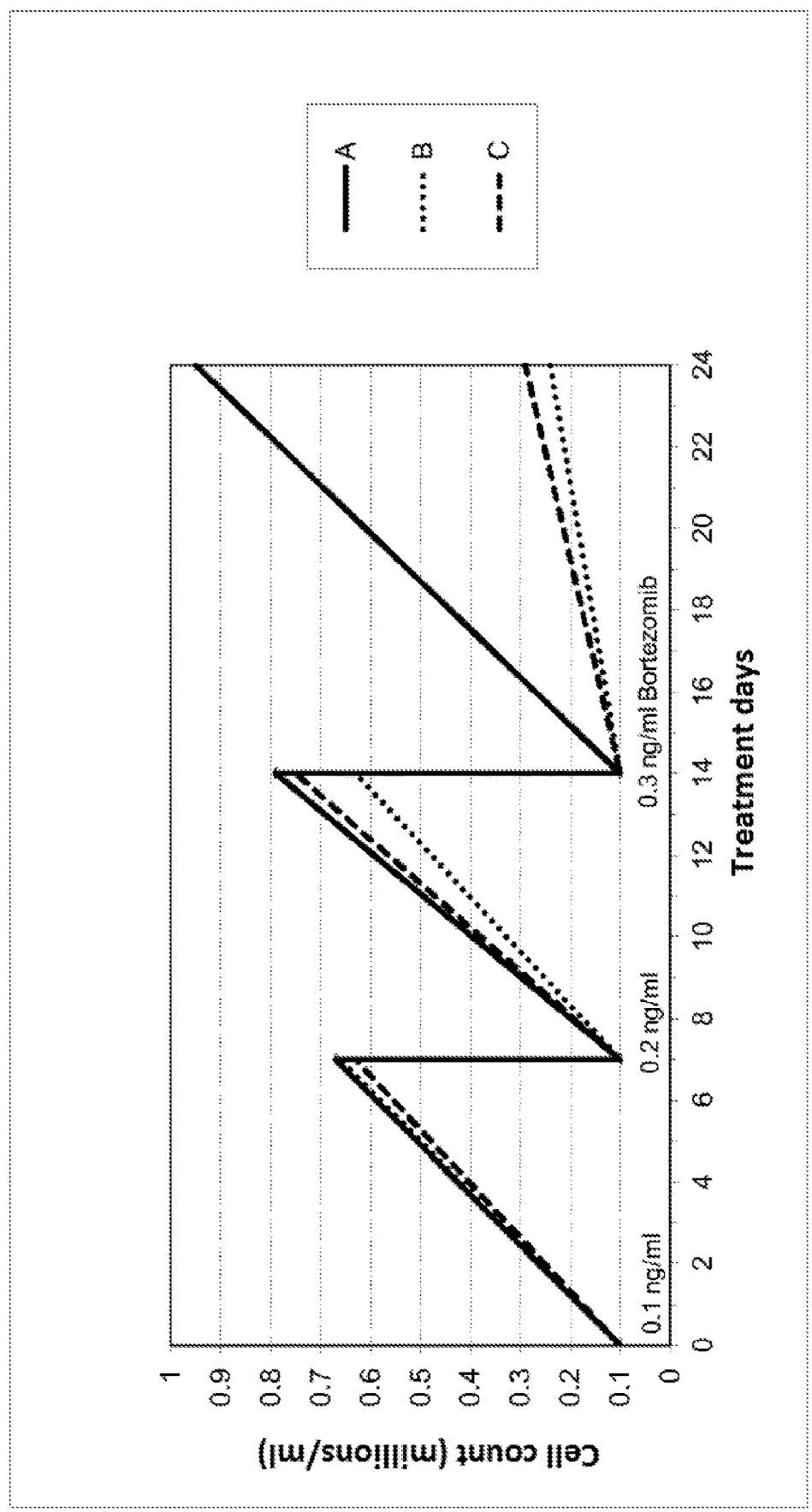
Figure 6B:
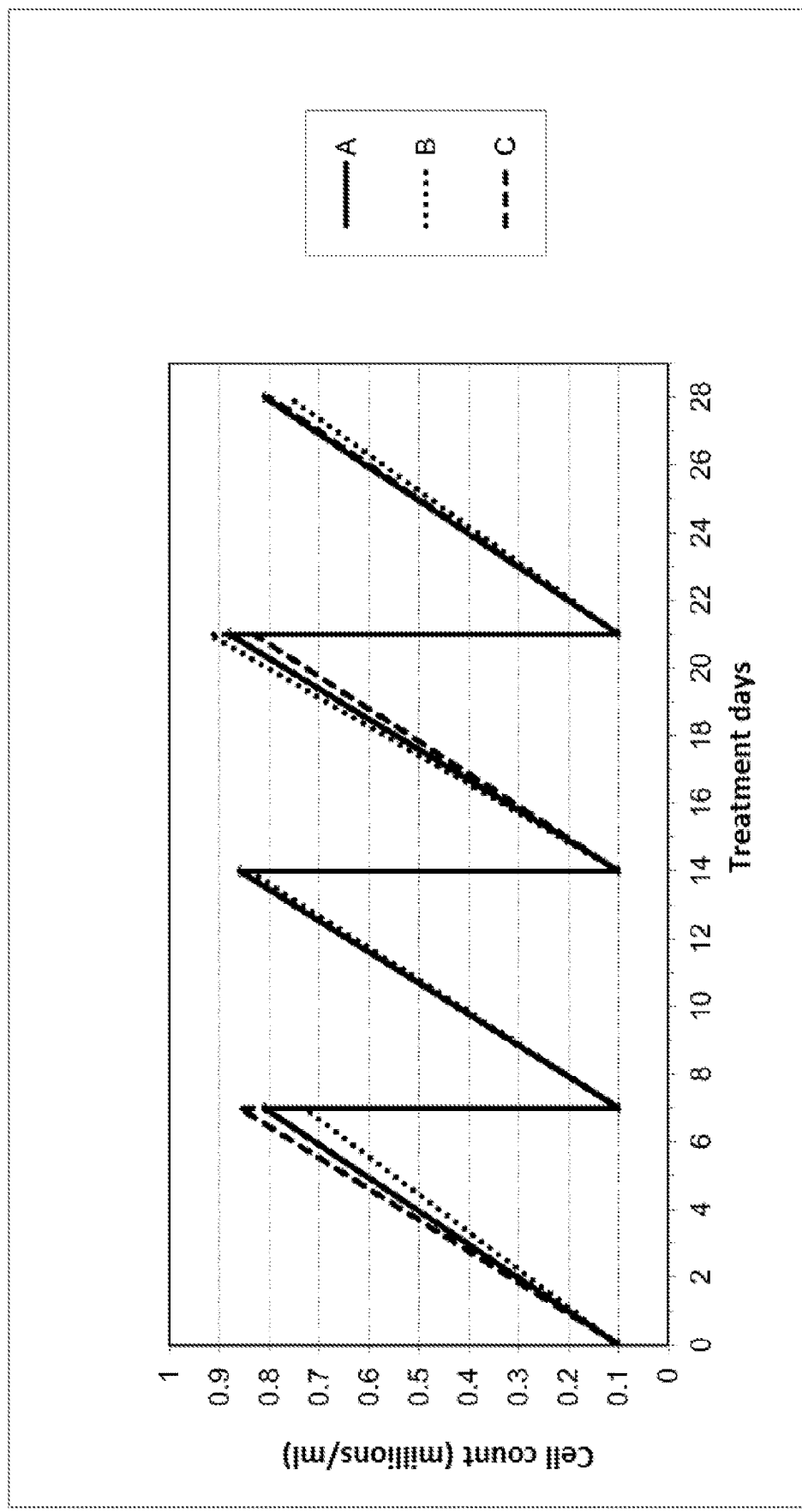

FIG. 6 shows the inhibition of the development of resistance of the tumour cell line RPMI-8226 by 2-(4-butylphenylamino)-9-(2-hydroxyethoxymethyl)-1,9-dihydropurin-6-one. FIG. 6a shows RPMI 8226 cells treated with cytostatic agent bortezomib 0.1-0.3 ng/ml (A), combination treatment with bortezomib plus 1 µM 2-(4-butylphenylamino)-9-(2-hydroxy-ethoxymethyl)-1,9-dihydropurin-6-one (B) and combination treatment with bortezomib plus 30 µM BVDU (C). FIG. 6b shows the control without cytostatic agent: RPMI 8226 cells untreated (A), 1 µM 2-(4-butylphenylamino)-9-(2-hydroxyethoxymethyl)-1,9-dihydropurin-6-one alone (B) and 30 µM BVDU alone (C).

Figure 7A:
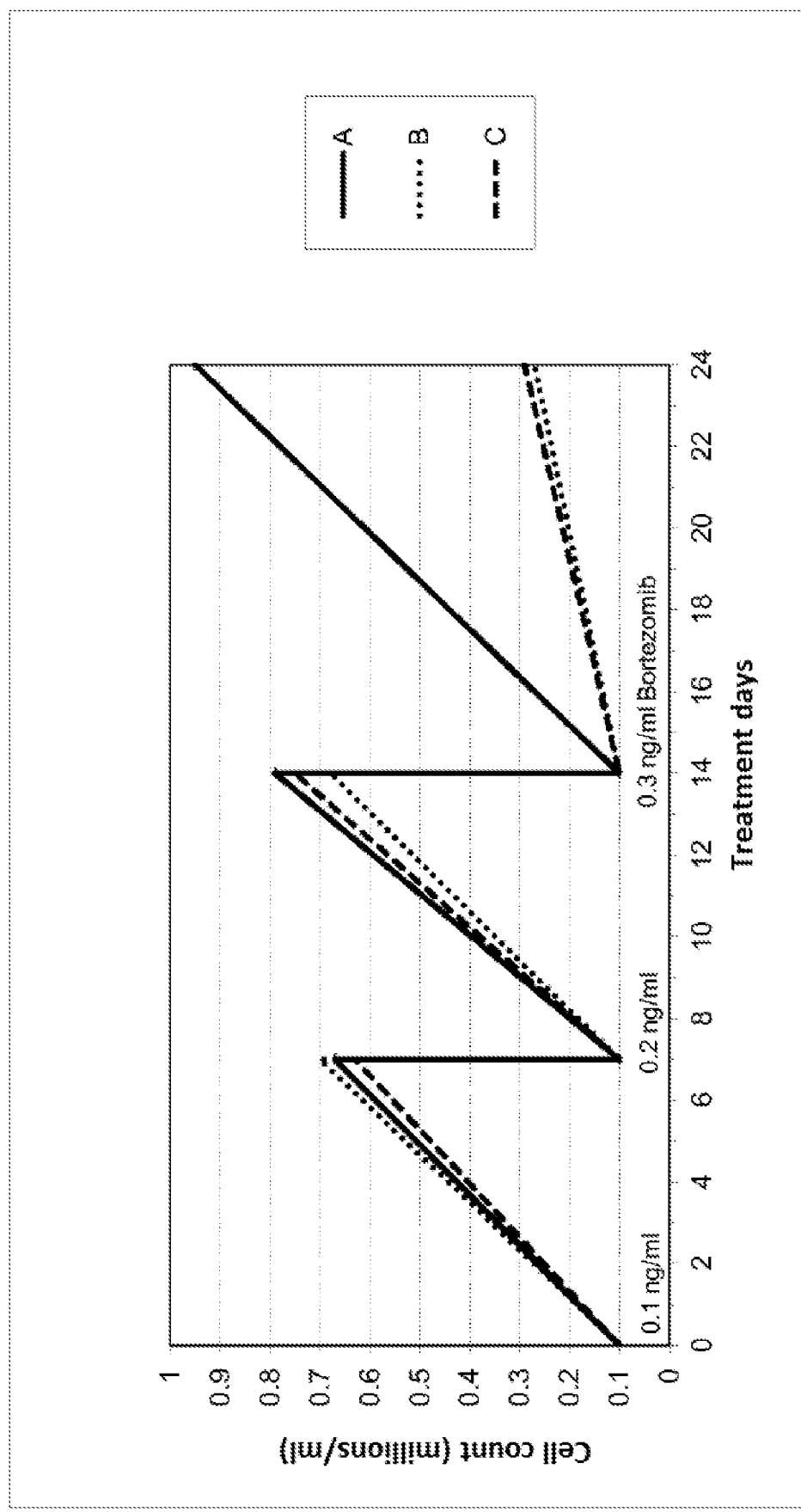
Figure 7B:
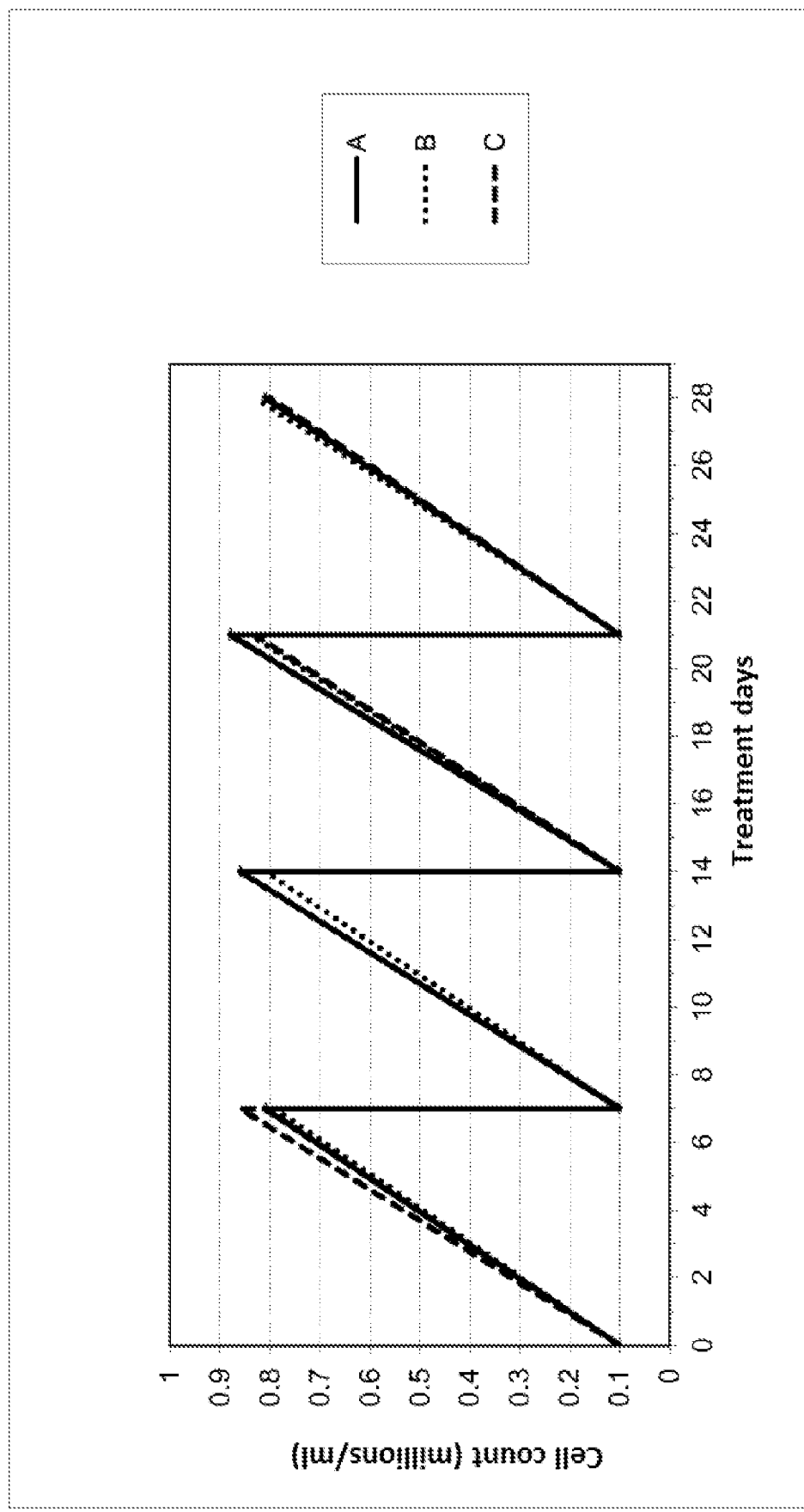

FIG. 7 shows the inhibition of the development of resistance of the tumour cell line RPMI-8226 by 2-(3-trichlorovinylphenylamino)-1,9-dihydropurin-6-one. FIG. 7a shows RPMI 8226 cells treated with cytostatic agent bortezomib 0.1-0.3 ng/ml (A), combination treatment with bortezomib plus 1 µM 2-(3-trichlorovinylphenylamino)-1,9-dihydropurin-6-one (B) and combination treatment with bortezomib plus 30 µM BVDU (C). FIG. 7b shows the control without cytostatic agent: RPMI 8226 cells untreated (A), 1 µM 2-(3-trichlorovinyl-phenylamino)-1,9-dihydropurin-6-one alone (B) and 30 µM BVDU alone (C).

Figure 8A:
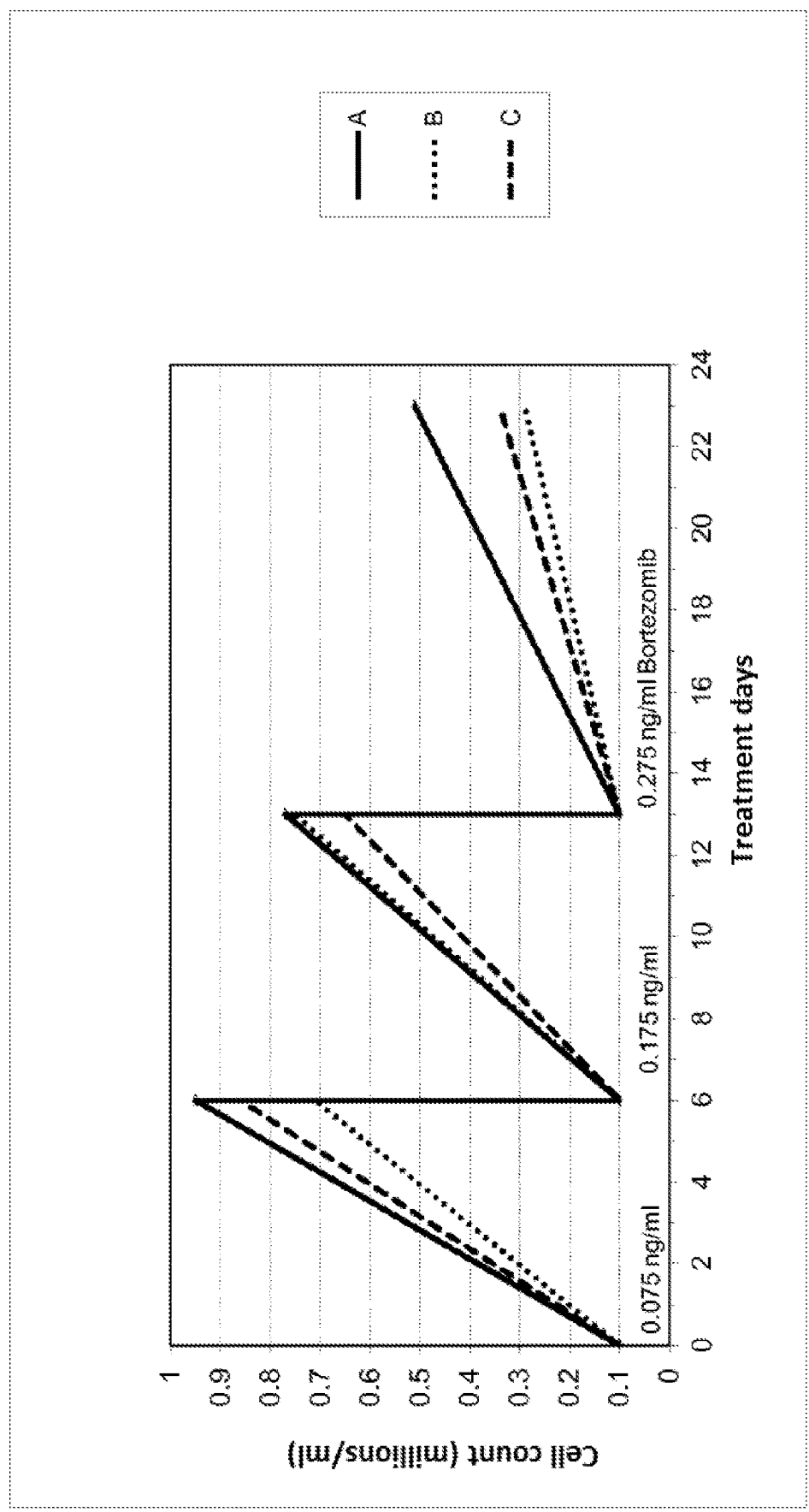
Figure 8B:
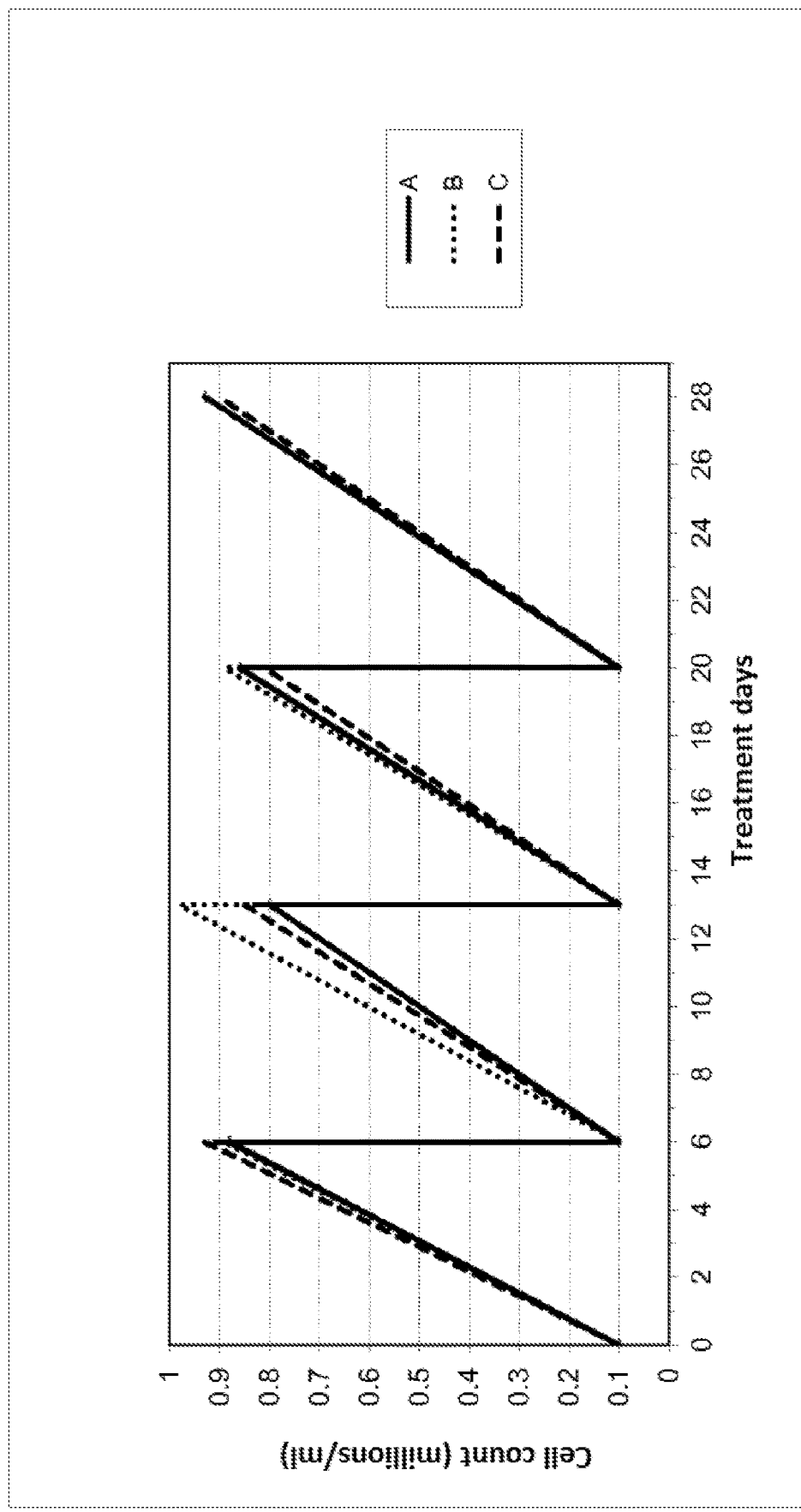

FIG. 8 shows the inhibition of the development of resistance of the tumour cell line RPMI-8226 by 9H-xanthene-9-carboxylic acid [4-(5-methyl-2,4-dioxo-3,4-dihydro-2H-pyrimidin-1-yl)-but-2-enyl]amide. FIG. 8a shows RPMI 8226 cells treated with cytostatic agent bortezomib 0.075-0.275 ng/ml (A), combination treatment with bortezomib plus 1 µM 9H-xanthene-9-carboxylic acid [4-(5-methyl-2,4-dioxo-3,4-dihydro-2H-pyrimidin-1-yl)-but-2-enyl]amide (B) and combination treatment with bortezomib plus 30 µM BVDU (C). FIG. 8b shows the control without cytostatic agent: RPMI 8226 cells untreated (A), 1 µM 9H-xanthene-9-carboxylic acid [4-(5-methyl-2,4-dioxo-3,4-dihydro-2H-pyrimidin-1-yl)-but-2-enyl]amide alone (B) and 30 µM BVDU alone (C).

Figure 9A:
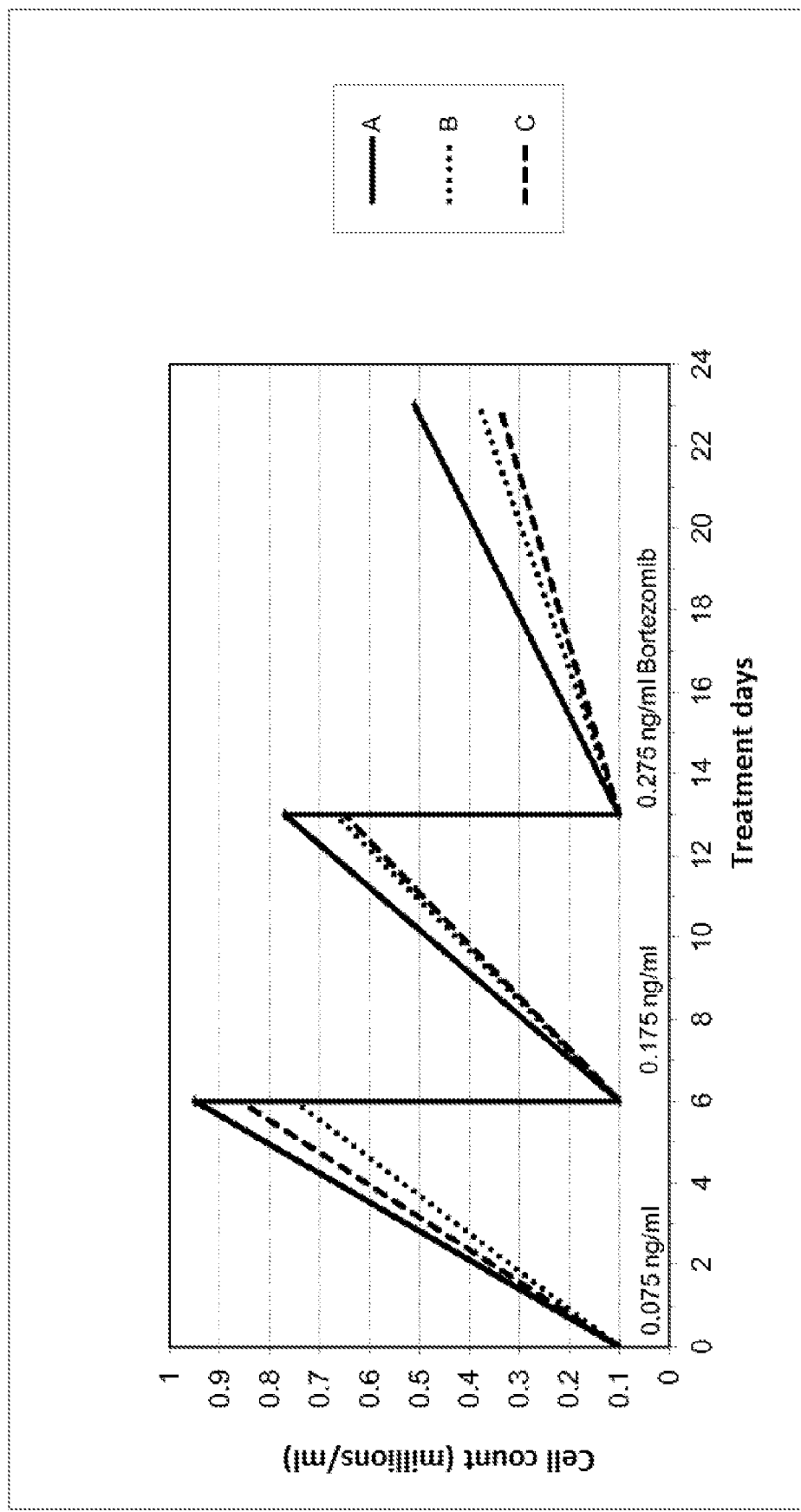
Figure 9B:
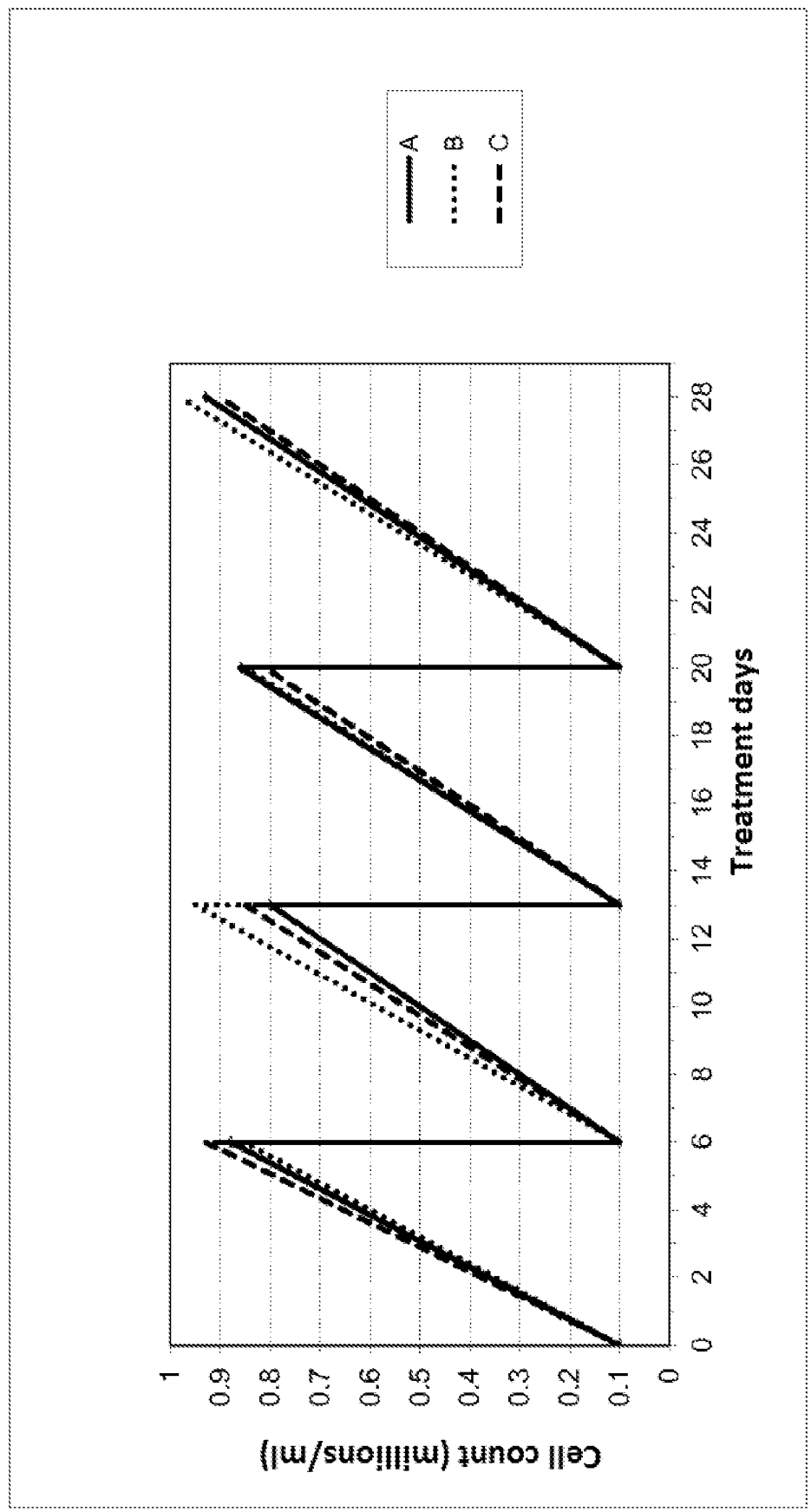

FIG. 9 shows the inhibition of the development of resistance of the tumour cell line RPMI-8226 by 2-biphenyl-4-yl-N-[4-(5-methyl-2,4-dioxo-3,4-dihydro-2H-pyrimidin-1-yl)-but-2-enyl]-acetamide. FIG. 9a shows RPMI 8226 cells treated with cytostatic agent bortezomib 0.075-0.275 ng/ml (A), combination treatment with bortezomib plus 1 µM 2-biphenyl-4-yl-N-[4-(5-methyl-2,4-dioxo-3,4-dihydro-2H-pyrimidin-1-yl)-but-2-enyl]acetamide (B) and combination treatment with bortezomib plus 30 µM BVDU (C). FIG. 9b shows the control without cytostatic agent: RPMI 8226 cells untreated (A), 1 µM 2-biphenyl-4-yl-N-[4-(5-methyl-2,4-dioxo-3,4-dihydro-2H-pyrimidin-1-yl)-but-2-enyl]acetamide alone (B) and 30 µM BVDU alone (C).

Figure 10A:
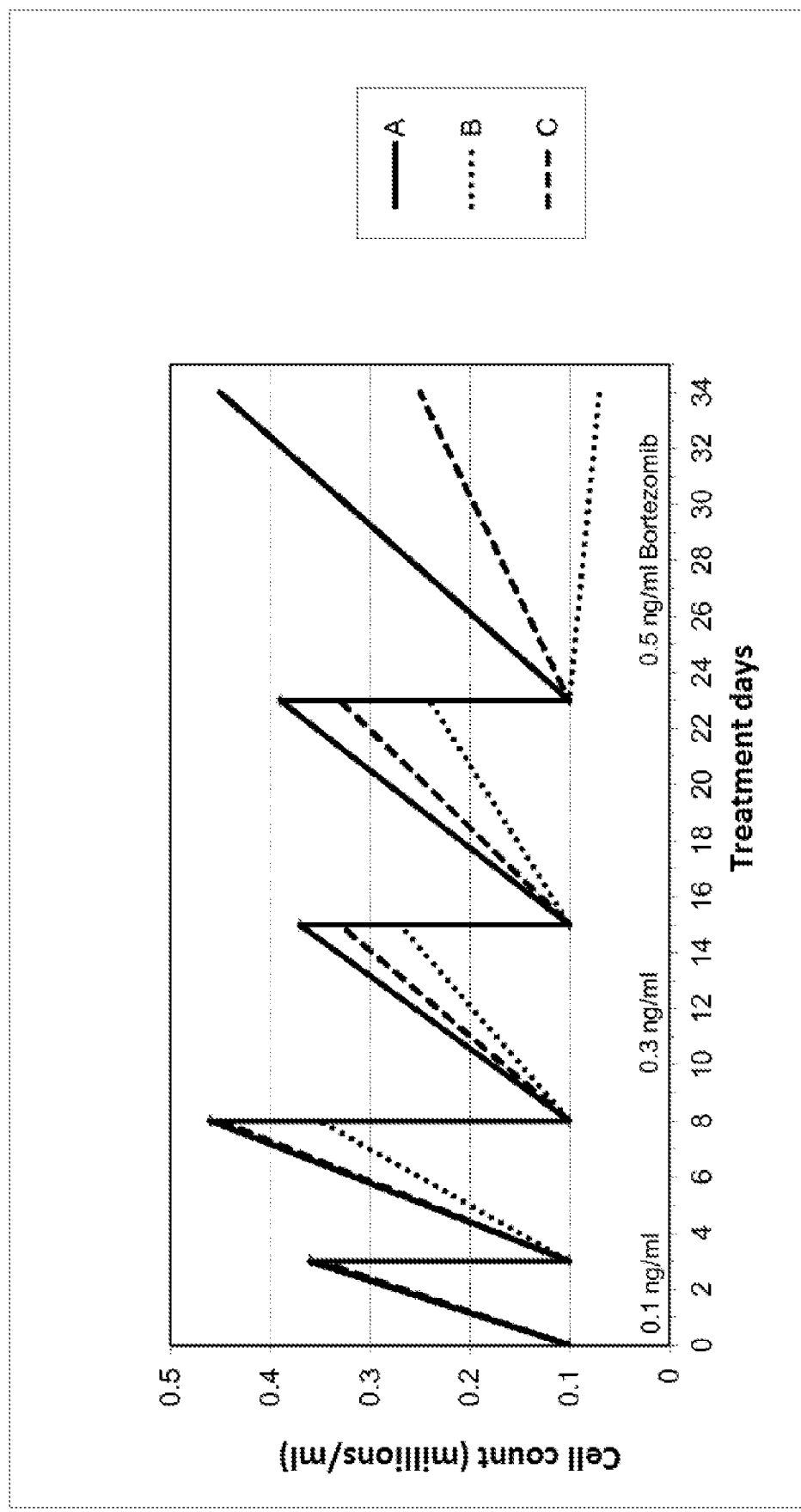
Figure 10B:
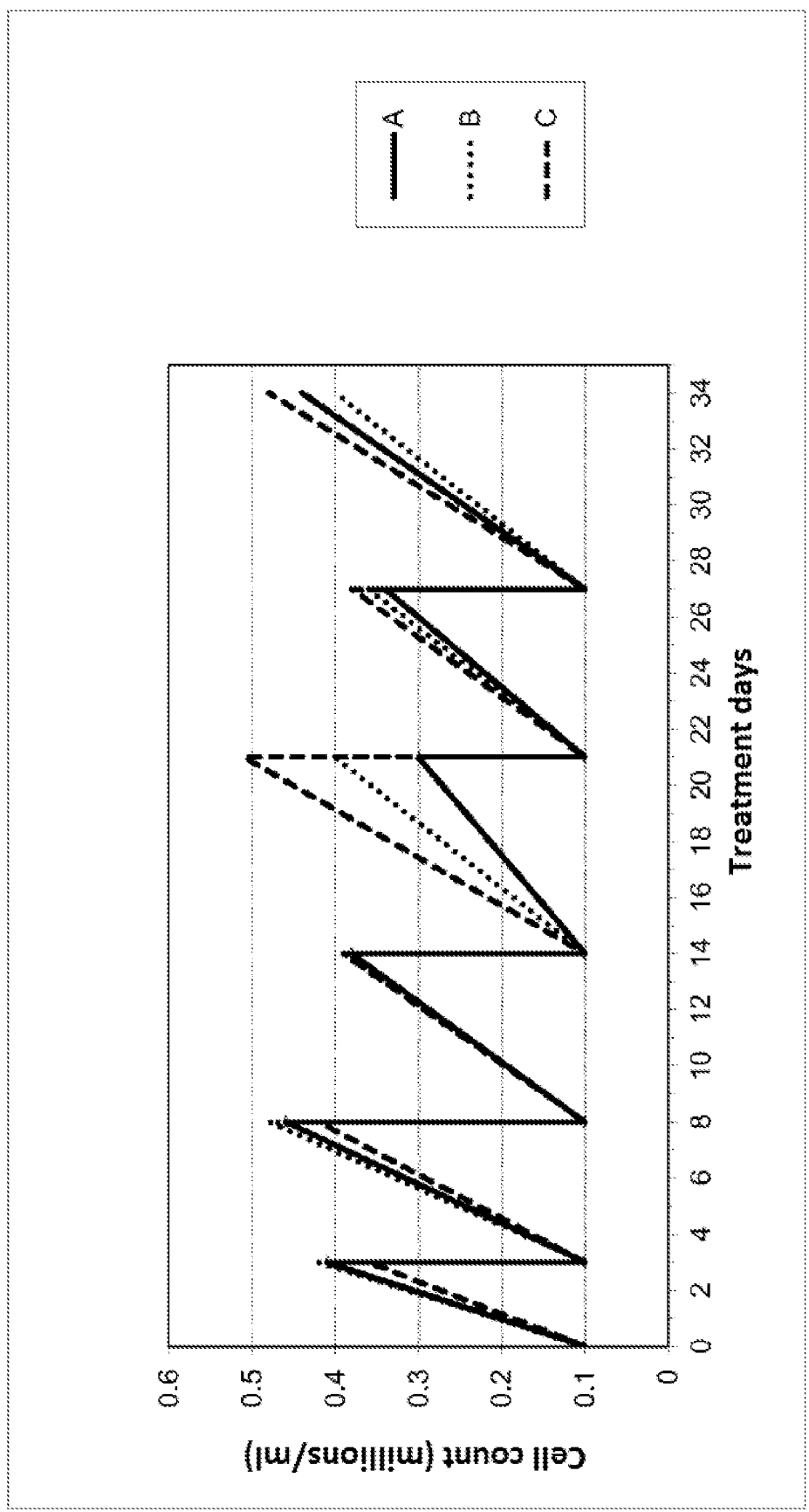

FIG. 10 shows the inhibition of the development of resistance of the tumour cell line U-937 by acepromazine. FIG. 10a shows U-937 cells treated with cytostatic agent bortezomib 0.1-0.5 ng/ml (A), combination treatment with bortezomib plus 0.75 µM acepromazine (B) and combination treatment with bortezomib plus 30 µM BVDU (C). FIG. 10b shows the control without cytostatic agent: RPMI 8226 cells untreated (A), 0.75 µM acepromazine alone (B) and 30 µM BVDU alone (C).

Figure 11A:
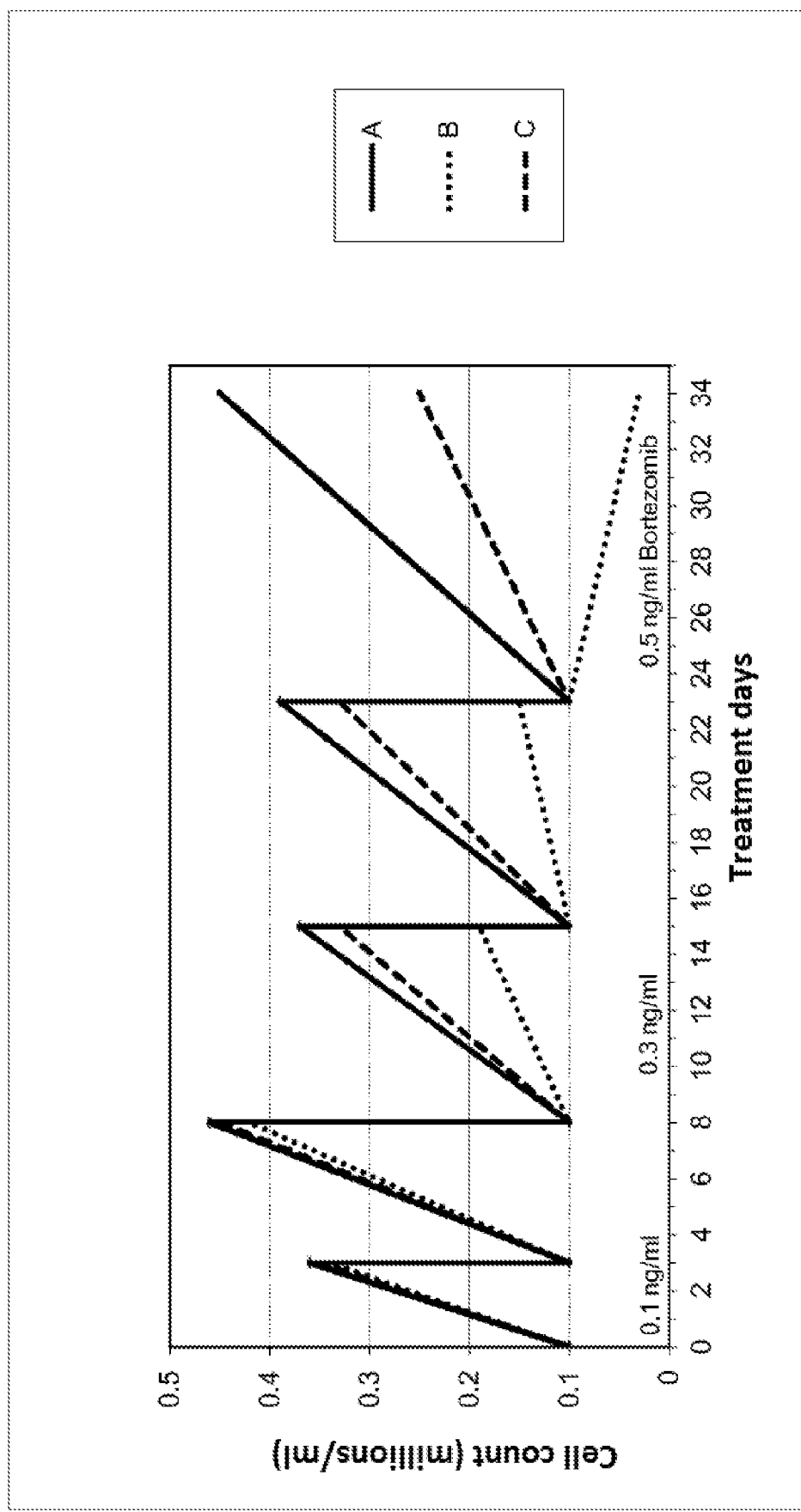
Figure 11B:
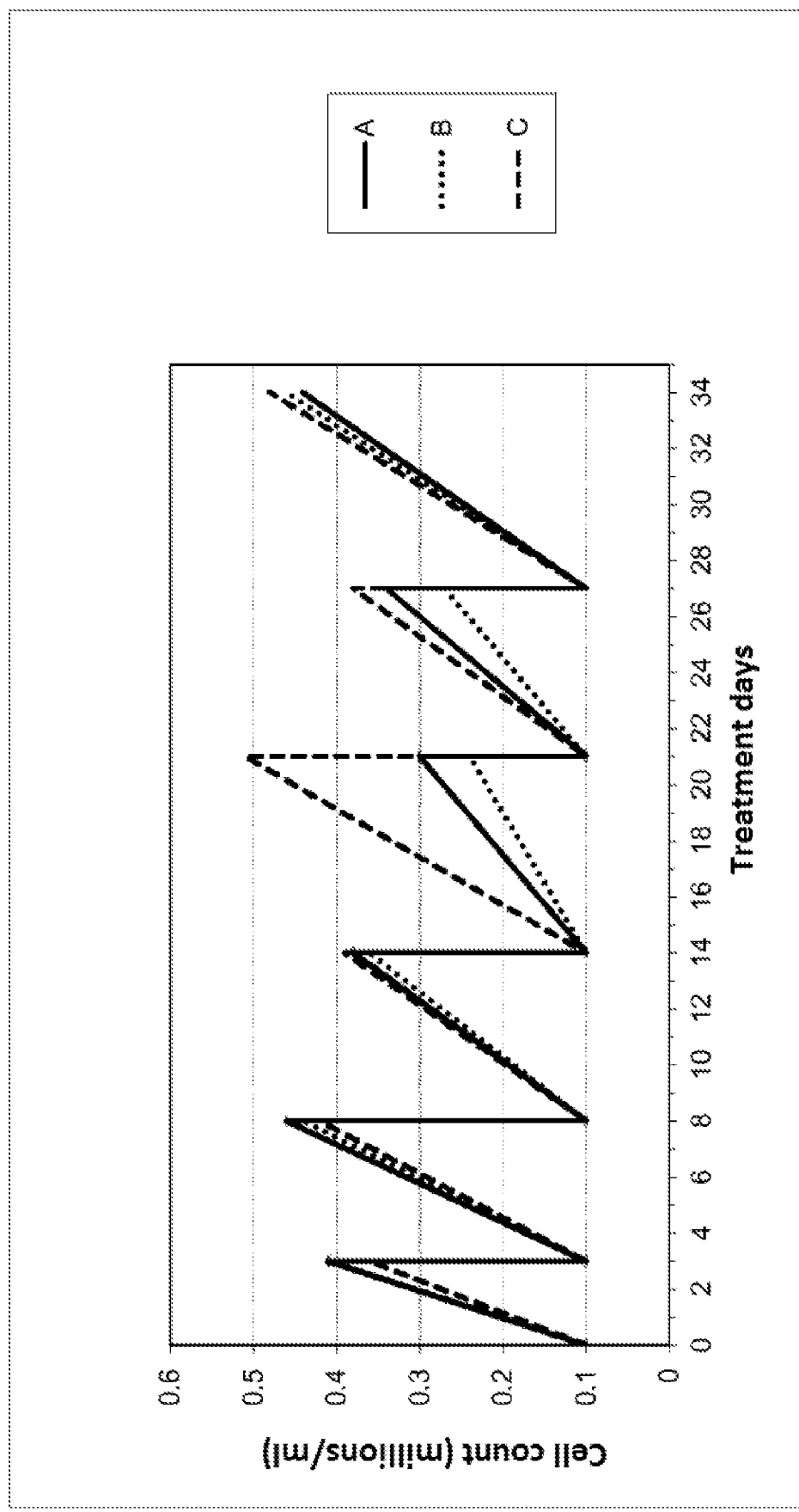

FIG. 11 shows the inhibition of the development of resistance of the tumour cell line U-937 by 2-(4-butylphenylamino)-9-(2-hydroxyethoxymethyl)-1,9-dihydropurin-6-one. FIG. 11a shows U-937 cells treated with cytostatic agent bortezomib 0.1-0.5 ng/ml (A), combination treatment with bortezomib plus 0.75 µM 2-(4-butylphenylamino)-9-(2-hydroxyethoxymethyl)-1,9-dihydropurin-6-one (B) and combination treatment with bortezomib plus 30 µM BVDU (C). FIG. 11b shows the control without cytostatic agent: RPMI 8226 cells untreated (A), 0.75 µM 2-(4-butylphenylamino)-9-(2-hydroxyethoxymethyl)-1,9-dihydropurin-6-one alone (B) and 30 µM BVDU alone (C).

EXAMPLE 1—SPEEDSCREEN OF PURINE DERIVATIVES

For the experimental validation of low-molecular-weight compounds which act as potential HSP27 inhibitors according to the in silico prediction, a method based on gel filtration was employed.

The method for detecting molecular bonds using gel filtration was described in 2004 as "SpeedScreen" [Muckenschnabel et al., 2004] and was adapted to meet the requirements of the invention. The method of separation consists in the fact that larger molecules, such as e.g. proteins, can pass through a matrix of Sephadex G-25, while low-molecular-weight compounds (small molecules) penetrate into the matrix and do not pass through it. For the separation, PD SpinTraps G-25 from GE Healthcare were used. During the 2-minute centrifugation at 800×g (according to operating instructions), these columns allow molecules with a molecular weight of greater than or equal to 5000 g/mol to pass through, while smaller molecules are retained in the matrix.

The target protein HSP27 has a molecular weight of 27000 g/mol and therefore passes through the matrix. The HSP27 inhibitors of general formula (I) described according to the invention are low-molecular-weight compounds, which can only pass through the Sephadex G-25 matrix if they have previously bound to the target protein HSP27 and are transported thereby through the matrix. Non-bound low-molecular-weight compounds are retained by the matrix. Molecules that have passed through the matrix can then be detected by mass spectroscopy. This enables "binders" to be differentiated from "non-binders".

Result

Representatives of the purine derivatives according to general formula (I) tested by SpeedScreen are:
2-(3-trichlorovinylphenylamino)-1,9-dihydropurin-6-one
2-(4-butylphenylamino)-9-(2-hydroxyethoxymethyl)-1,9-dihydropurin-6-one
2-(3-hydroxymethylphenylamino)-3,7-dihydropurin-6-one Furthermore, acepromazine (as acepromazine maleate) was tested positively as a representative of the phenothiazine derivatives by means of SpeedScreen.

The three purine derivatives pass through the Sephadex G-25 matrix and are detected in the medium after the passage. The binding of the phenothiazine derivatives acepromazine (as acepromazine maleate) and chlorpromazine to HSP27 could also be positively detected by means of bio-layer interferometry with a $K_D$=72 µmol/L and 770 µmol/L respectively.

EXAMPLE 2—SPEEDSCREEN OF THYMINE DERIVATIVES

For the experimental validation of low-molecular-weight compounds which act as potential HSP27 inhibitors according to the in silico prediction, a method based on gel filtration was employed.

The method for detecting molecular bonds using gel filtration was described in 2004 as "SpeedScreen" [Muckenschnabel et al., 2004] and was adapted to meet the requirements of the invention. The method of separation consists in the fact that larger molecules, such as e.g. proteins, can pass through a matrix of Sephadex G-25, while low-molecular-weight compounds (small molecules) penetrate into the matrix and do not pass through it. For the separation, PD SpinTraps G-25 from GE Healthcare were used. During the 2-minute centrifugation at 800×g (according to operating instructions), these columns allow molecules with a molecular weight of greater than or equal to 5000 g/mol to pass through, while smaller molecules are retained in the matrix.

The target protein HSP27 has a molecular weight of 27000 g/mol and therefore passes through the matrix. The HSP27 inhibitors of general formula (I) described according to the invention are low-molecular-weight compounds, which can only pass through the Sephadex G-25 matrix if they have previously bound to the target protein HSP27 and are transported thereby through the matrix. Non-bound low-molecular-weight compounds are retained by the matrix. Molecules that have passed through the matrix can then be detected by mass spectroscopy. This enables "binders" to be differentiated from "non-binders".

Result

Representatives of the thymine derivatives according to general formula (VI) tested by SpeedScreen are:
9H-xanthene-9-carboxylic acid [4-(5-methyl-2,4-dioxo-3,4-dihydro-2H-pyrimidin-1-yl)-but-2-enyl]amide
2-biphenyl-4-yl-N-[4-(5-methyl-2,4-dioxo-3,4-dihydro-2H-pyrimidin-1-yl)-but-2-enyl]-acetamide Both thymine derivatives pass through the Sephadex G-25 matrix and are detected in the medium after the passage.

The binding of the phenothiazine derivatives acepromazine (as acepromazine maleate) and chlorpromazine to HSP27 could also be positively detected by means of bio-layer interferometry with a $K_D$=72 µmol/L and 770 µmol/L respectively.

EXAMPLE 3—DETECTION OF BINDING BY BIO-LAYER INTERFEROMETRY

Bio-layer interferometry is a technique for detecting biomolecular interactions. It is an analytical technique that measures the optical interference of white light which is reflected by two surfaces: in each case, one surface consists of a layer of the immobilized target protein on the tip of the biosensor and one is an internal reference surface. The binding of ligands to the target protein alters the interference pattern and can be measured in real time.

For the measurements, an instrument of the ForteBio Octet Red 384 brand was used. The target protein HSP27 was biotinylated and bound to the appropriate sensors (SSA). One great advantage of this analytical method consists in the fact that the analytes do not have to be either immobilized or labelled. The purine derivatives of general formula (I) or (II) pre-identified by means of in silico screening are employed for these measurements in a concentration range ($K_D$) of between 333 µmol/L and 10 nmol/L.

Using the bio-layer interferometry method, the purine derivative 2-(4-butylphenylamino)-9-(2-hydroxyethoxymethyl)-1,9-dihydropurin-6-one could be positively detected as an HSP27-binding low-molecular-weight compound with a $K_D$=15 µmol/L.

The binding of the phenothiazine derivatives acepromazine (as acepromazine maleate) and chlorpromazine to HSP27 could also be positively detected by means of bio-layer interferometry with a $K_D$=72 µmol/L or 770 µmol/L respectively.

EXAMPLE 4—SPECTROPHOTOMETRIC PROTEIN AGGREGATION ASSAY

To measure the efficacy of the purine derivatives according to the invention, robust experiments for the chaperone function of the HSP27 protein were performed:

A known client protein (=substrate on which HSP27 acts as a chaperone) of HSP27 is citrate synthase. Citrate synthase is denatured when the temperature increases to 43° C. This heat denaturation is prevented or delayed by the presence of HSP27 [Jakob U, 1993]. By adding the novel active ingredients, their efficacy can thus be measured through the inhibition of the HSP27 chaperone function.

To determine the activity (i.e. the effect on the aggregation behaviour of the citrate synthase (CS) after thermal incubation) of 2-(3-trichlorovinylphenylamino)-1,9-dihydropurin-6-one in comparison to BVDU, four different batches containing 1.44 µmol/L CS, 481 nmol/L HSP27 (HSP) in a 40 mmol/L HEPES buffer (pH 7.4) were prepared and BVDU (750 µmol/L) or various concentrations of 2-(3-trichlorovinylphenylamino)-1,9-dihydropurin-6-one (14 µmol/L; 28 µmol/L) were added. The samples were then incubated at 43° C. and the aggregation behaviour of the CS was mol/Litored in a spectrometer (PerkinElmer LS55, PerkinElmer Inc.) at a wavelength of 500 nm.

It can be seen from FIG. 1 that the protein citrate synthase (graph CS alone) is denatured by increasing the temperature to 43° C. and forms aggregates. The aggregation is measured in the spectrometer at 500 nm (light scattering by protein aggregates). The presence of HSP27 (HSP) counteracts the aggregation (cf. graph, CS+HSP). Since the addition of the test substances (BVDU and 2-(3-trichlorovinylphenylamino)-1,9-dihydropurin-6-one) inhibits the chaperone function of HSP27, the activity of the respective test substance can be determined by measuring the aggregation behaviour of the CS.

It is clear that CS alone forms aggregates very rapidly; these CS aggregates then precipitate in the measuring cuvette, so that the red graph falls again after reaching the peak. Through the presence of HSP27, CS aggregation is prevented over the period of one hour shown here. BVDU partially cancels the chaperone function of HSP27 at a concentration of 750 µmol/L BVDU. The test substance 2-(3-trichlorovinylphenylamino)-1,9-dihydropurin-6-one shows a comparable effect at a concentration of 14 µmol/L and a significantly more pronounced effect at 28 µmol/L.

The inhibition of HSP27 correlates to the binding strength of a low-molecular-weight organic compound to the active ingredient binding pocket of HSP27. The active concentration of a low-molecular-weight organic compound interacting with HSP27 can be converted to BVDU equivalents via the activity of BVDU, i.e. equal to the HSP27 inhibiting dose in mg BVDU. Based on 100 mg BVDU, the test substance 2-(3-trichlorovinylphenylamino)-1,9-dihydropurin-6-one has a BVDU equivalent dose of less than 1.9 mg.

EXAMPLE 5—CAPILLARY ELECTROPHORESIS OF THE CS PROTEIN PRECIPITATES WITH PURINE DERIVATIVES

Since the heat-denatured protein aggregates of the citrate synthase from Example 1 are not water-soluble, these can be separated completely from the supernatant by means of centrifugation at room temperature at 16,000×g, 10 min. By using capillary electrophoresis, the compositions of the separated precipitates can be shown and quantified. The relative quantity of protein of precipitated citrate synthase serves as a measure of the efficacy of the test substances.

In each case, 481 nmol/L HSP27 and 1.44 μmol/L citrate synthase in 40 mmol/L HEPES buffer, pH 7.4, were employed. The relative quantity of protein of the precipitated citrate synthase in each case was normalized using a defined quantity of BSA as internal standard. The relative quantity of protein that precipitated when using 750 μmol/L BVDU was set at 1. The other test substances (2 representatives of phenothiazine derivatives of general formula (V), 2 representatives of purine derivatives of formula (I) or (II)) were each employed at a concentration of 10 μmol/L.

Table 1 below shows the separation by capillary electrophoresis of heat-denatured protein aggregates of citrate synthase after thermal treatment of the samples at 43° C. for 120 minutes.

Overview of test results:

| Dose | Substance employed | Rel. quantity of protein prec. CS | Efficacy compared with BVDU |
|---|---|---|---|
| 750 μmol/L | BVDU | 1 | |
| 10 μmol/L | Chlorpromazine | 1.06 | 79.5 x |
| 10 μmol/L | Acepromazine | 0.99 | 74.25 x |
| 10 μmol/L | 2-(4-Butylphenylamino)-9-(2-hydroxyethoxymethyl)-1,9-dihydropurin-6-one | 0.92 | 69.0 x |
| 10 μmol/L | 2-(3-Trichlorovinyl-phenylamino)-1,9-dihydropurin-6-one | 0.71 | 53.25 x |

The four test substances proved significantly more effective than the reference substance BVDU when used at a concentration of 10 μmol/L in each case, and can therefore be given in a dose in the range of between 53 and 79 times lower to achieve an effect comparable with that of the conventional BVDU. In particular, the purine derivative 2-(4-butyl-phenylamino)-9-(2-hydroxyethoxymethyl)-1,9-dihydropurin-6-one shows a 69 times higher activity than BVDU for the inhibition of the HSP27 protein (BVDU equivalent dose is 1.4 mg). However, the purine derivative 2-(3-trichlorovinylphenylamino)-1,9-dihydropurin-6-one also shows a 53 times higher activity for the inhibition of the HSP27 protein compared with BVDU, which corresponds to a BVDU equivalent dose of less than 1.9 mg.

EXAMPLE 6—TESTING THE HSP27 INHIBITORS IN CANCER CELLS

Cancer cells develop resistances extremely rapidly when they are treated with cytostatic agents. This is the reason for numerous failures in chemotherapy. HSP27 favours the development of chemoresistances, e.g. by interacting with apoptosis proteins and thus preventing the sought cell death of the cancer cells. For bortezomib (Velcade) in particular, a modern cytostatic agent (proteasome inhibitor), the HSP27-driven development of resistance is well documented [Chauhan D, 2004].

In the cell experiments described here, it is shown that, by administering the novel HSP27 inhibitors, the development of resistance to the cytostatic agent bortezomib is prevented in U937 cells. In this case, acepromazine was tested in comparison with BVDU.

For this purpose, U937 cells (histiocytic lymphoma) were cultured in DMEM culture medium (+10% FCS) at 37° C., 5% $CO_2$ in an $H_2O$-saturated atmosphere. 100,000 cells/ml were seeded and incubated with the cytostatic agent bortezomib (0.1 ng/ml) and the respective test substance (dosage in the current experiment: 1 μM/L acepromazine). The reference substance, BVDU, was employed at a concentration of 30 μM/L. The cells were in each case passaged before the cell count reached 1,000,000 cells/ml. At each passage, 100,000 cells/ml were again seeded and the dose of the cytostatic agent bortezomib was increased stepwise (0.1 ng/mL or 0.05 ng/mL). The concentration of the test substances remained constant. As a result of the stepwise increase in the dosage of the cytostatic agent, resistance developed in the U937 cells. The development of resistance is prevented or inhibited in the case of a positively tested HSP27 inhibitor.

It can be seen from FIG. 2 that, by treating U937 cells with acepromazine (+1 μM ACE), no development of resistance occurred and therefore no living cells were detectable after the end of the experiment. In contrast, for U937 cells treated with BVDU (+30 μM BVDU), a final cell count of 430,000 cells/ml was detected whereas the final cell count in the culture without the addition of an HSP27 inhibitor amounted to 790,000 cells/ml. As a control, U937 cells were treated with the respective test substances alone. At the same dosage, the test substances alone have no effect on cell growth, since HSP27 is not needed in a large quantity by the cancer cells without the pressure by the cytostatic agent. The harmful effect of HSP27 for the patient on the development of resistance only becomes clear when the cytostatic agent is administered simultaneously.

EXAMPLE 7—TESTING THE HSP27 INHIBITORS IN CANCER CELLS

The experiments from Example 6 were repeated in the same way, wherein U937 cells (histiocytic lymphoma) are cultured in DMEM culture medium (+10% FCS) at 37° C., 5% $CO_2$ in an $H_2O$-saturated atmosphere. 100,000 cells/ml were seeded and incubated with an initial concentration of 0.2 ng/ml of the cytostatic agent bortezomib and both without an inhibitor and with acepromazine as an HSP27 inhibitor at a concentration of 1 μM/L. The reference substance, BVDU, was employed at a concentration of 30 μM/L. The cells were passaged in each case before the cell count reached 1,000,000 cells/ml. At each passage, 100,000 cells/ml were again seeded and the dose of the cytostatic agent bortezomib was increased stepwise by 0.1 ng/mL. The concentration of the test substance and the reference substance remained constant. As a result of the stepwise increase in the dosage of the cytostatic agent, resistance developed in the U937 cells. The development of resistance is prevented or inhibited in the case of a positively tested HSP27 inhibitor.

It can be seen from FIG. 3 that, by treating U937 cells with acepromazine (+1 μM ACE), no development of resistance occurred and therefore no living cells were detectable after the end of the experiment. In contrast, for U937 cells treated with BVDU (+30 µM BVDU), a final cell count of 60,000 cells/ml was detected whereas the final cell count in the culture without the addition of an HSP27 inhibitor amounted to 230,000 cells/ml.

As a control, U937 cells were treated with the respective test substances alone. At the same dosage, the test substances alone have no effect on cell growth, since HSP27 is not needed in a large quantity by the cancer cells without the pressure by the cytostatic agent. The harmful effect of HSP27 for the patient on the development of resistance only becomes clear when the cytostatic agent is administered simultaneously.

EXAMPLE 8—CAPILLARY ELECTROPHORESIS OF THE CS PROTEIN PRECIPITATES WITH THYMINE DERIVATIVES

Since the heat-denatured protein aggregates of the citrate synthase from Example 2 are not water-soluble, these can be separated completely from the supernatant by means of centrifugation at room temperature at 16,000×g, 10 min. By using capillary electrophoresis, the compositions of the separated precipitates can be shown and quantified. The relative quantity of protein of precipitated citrate synthase serves as a measure of the efficacy of the test substances.

In each case, 481 nM HSP27 and 1.44 µmol/L citrate synthase in 40 mmol/L HEPES buffer, pH 7.4, were employed. The relative quantity of protein of the precipitated citrate synthase in each case was normalized using a defined quantity of BSA as internal standard. The relative quantity of protein that precipitated when using 750 µmol/L BVDU was set at 1. The other test substances (2 representatives of phenothiazine derivatives of general formula (V), 2 representatives of thymine derivatives of formula (I) or (II)) were employed at a concentration of 10 µmol/L in each case.

Table 2 below shows the separation by capillary electrophoresis of heat-denatured protein aggregates of citrate synthase after thermal treatment of the samples at 43° C. for 120 minutes.

| Overview of the test results: | | | |
|---|---|---|---|
| Dose | Substance employed | Rel. quantity of protein prec. CS | Efficacy compared with BVDU |
| 750 µmol/L | BVDU | 1 | |
| 10 µmol/L | Chlorpromazine | 1.06 | 79.5 x |
| 10 µmol/L | Acepromazine | 0.99 | 74.25 x |
| 10 µmol/L | 9H-Xanthene-9-carboxylic acid[4-(5-methyl-2,4-dioxo-3,4-dihydro-2H-pyrimidin-1-yl)-but-2-enyl]amide | 0.65 | 48.75 x |
| 10 µmol/L | 2-Biphenyl-4-yl-N-[4-(5-methyl-2,4-dioxo-3,4-dihydro-2H-pyrimidin-1-yl)-but-2-enyl]acetamide | 0.81 | 60.75 x |

The four test substances proved significantly more effective than the reference substance BVDU when used at a concentration of 10 µmol/L in each case, and can therefore be given in a dose in the range of between 49 and 79 times lower to achieve an effect comparable with that of the conventional BVDU. In particular, the thymine derivative 2-biphenyl-4-yl-N-[4-(5-methyl-2,4-dioxo-3,4-dihydro-2H-pyrimidin-1-yl)-but-2-enyl]acetamide shows a 61 times higher activity than BVDU for the inhibition of the HSP27 protein (BVDU equivalent dose is 1.6 mg). However, the thymine derivative 9H-xanthene-9-carboxylic acid[4-(5-methyl-2,4-dioxo-3,4-dihydro-2H-pyrimidin-1-yl)-but-2-enyl]amide also shows a 49 times higher activity for the inhibition of the HSP27 protein compared with BVDU, which corresponds to a BVDU equivalent dose of less than 2 mg.

Further Test Results

Table 3 below shows the results of the capillary electrophoretic separation of heat-denatured protein aggregates of citrate synthase after thermal treatment of the samples at 43° C. for 70 minutes for further thymine derivatives. Otherwise, the experiments were performed as described above:

| Dose | Substance employed | Rel. quantity of protein prec. CS | Efficacy compared with BVDU |
|---|---|---|---|
| 750 µmol/L | BVDU | 1 | |
| 10 µmol/L | N-[(2Z)-4-(2,4-Dioxo-3H-pyrimidin-1-yl)but-2-en-1-yl]-2-(naphthalen-2-yl)acetamide | 1.15 | 86.25 x |
| 10 µmol/L | N-[(2Z)-4-(2,4-Dioxo-3H-pyrimidin-1-yl)but-2-en-1-yl]-2-(4-phenylphenyl)acetamide | 0.88 | 66.15 x |
| 10 µmol/L | N-[(2Z)-4-(5-Methyl-2,4-dioxo-3H-pyrimidin-1-yl)but-2-en-1-yl]-9H-fluorene-9-carboxamide | 0.86 | 64.31 x |
| 10 µmol/L | 3'-Deoxy-3'-[4-(3,4-dichlorophenyl)-1H-1,2,3-triazol-1-yl]-thymidine | 0.86 | 64.21 x |
| 10 µmol/L | N-[(2Z)-4-(2,4-Dioxo-3H-pyrimidin-1-yl)but-2-en-1-yl]-9,9a-dihydro-4aH-xanthene-9-carboxamide | 0.85 | 63.38 x |
| 10 µmol/L | 3'-Deoxy-3'-[4-(2-pyridinyl)-1H-1,2,3-triazol-1]-yl]thymidine | 0.84 | 62.86 x |
| 10 µmol/L | N-[(2Z)-4-(5-Methyl-2,4-dioxo-3H-pyrimidin-1-yl)but-2-en-1-yl]-2-(naphthalen-2-yl)acetamide | 0.83 | 62.51 x |
| 10 µmol/L | N-[(2Z)-4-(5-Methyl-2,4-dioxo-3H-pyrimidin-1-yl)but-2-en-1-yl]-2,2-diphenylacetamide | 0.82 | 61.19 x |
| 10 µmol/L | 1-[(4S,5S)-4-[4-(3-Bromophenyl)-1H-1,2,3-triazol-1-yl]-5-(hydroxymethyl)oxolan-2-yl]-5-methyl-1,2,3,4-tetrahydropyrimidine-2,4-dione | 0.81 | 60.88 x |
| 10 µmol/L | N-[(2Z)-4-(5-Methyl-2,4-dioxo-3H-pyrimidin-1-yl)but-2-en-1-yl]-2-(naphthalen-1-yl)acetamide | 0.81 | 60.44 x |
| 10 µmol/L | 3'-Deoxy-3'-(4-propyl-1H-1,2,3-triazol-1-yl)thymidine | 0.79 | 59.59 x |
| 10 µmol/L | 3'-Deoxy-3'-(4-phenyl-1H-1,2,3-triazol-1-yl)thymidine | 0.79 | 59.07 x |

-continued

| Dose | Substance employed | Rel. quantity of protein prec. CS | Efficacy compared with BVDU |
|---|---|---|---|
| 10 µmol/L | N-[4-(5-Methyl-2,4-dioxo-3H-pyrimidin-1-yl)butyl]-2,2-diphenylacetamide | 0.79 | 58.97 x |
| 10 µmol/L | N-[(2Z)-4-(5-Methyl-2,4-dioxo-3H-pyrimidin-1-yl)but-2-en-1-yl]naphthalene-1-carboxamide | 0.78 | 58.73 x |
| 10 µmol/L | 3'-(4-Butyl-1H-1,2,3-triazol-1-yl)-3'-deoxythymidine | 0.76 | 57.08 x |
| 10 µmol/L | N-[4-(5-Methyl-2,4-dioxo-3H-pyrimidin-1-yl)butyl]-2-(naphthalen-2-yl)acetamide | 0.75 | 56.36 x |
| 10 µmol/L | 1-[(4S,5S)-5-(Hydroxymethyl)-4-[4-(4-methoxyphenyl)-1,2,3-triazol-1-yl]oxolan-2-yl]-5-methyl-3H-pyrimidine-2,4-dione | 0.75 | 55.89 x |
| 10 µmol/L | 3'-Deoxy-3'-[4-(2-phenylethyl)-1H-1,2,3-triazol-1-yl]-thymidine | 0.74 | 55.67 x |
| 10 µmol/L | 3'-Deoxy-3'-(4-pentyl-1H-1,2,3-triazol-1-yl)thymidine | 0.70 | 52.57 x |
| 10 µmol/L | N-[4-(5-Methyl-2,4-dioxo-3H-pyrimidin-1-yl)butyl]-9H-xanthene-9-carboxamide | 0.68 | 51.16 x |
| 10 µmol/L | 3'-[4-(4-Chlorophenyl)-1H-1,2,3-triazol-1-yl]-3'-deoxythymidine | 0.67 | 50.53 x |
| 10 µmol/L | N-[4-(5-Methyl-2,4-dioxo-3H-pyrimidin-1-yl)butyl]-2-(4-phenylphenyl)acetamide | 0.67 | 50.52 x |
| 10 µmol/L | 3'-Deoxy-3'-[4-(4-fluorophenyl)-1H-1,2,3-triazol-1-yl]-thymidine | 0.66 | 49.69 x |
| 10 µmol/L | 3'-[4-(Cyclopentylmethyl)-1H-1,2,3-triazol-1-yl]-3'-deoxythymidine | 0.66 | 49.63 x |
| 10 µmol/L | 1-[(4S,5S)-4-[4-(4-Bromophenyl)-1,2,3-triazol-1-yl]-5-(hydroxymethyl)oxolan-2-yl]-5-methyl-3H-pyrimidine-2,4-dione | 0.64 | 48.14 x |
| 10 µmol/L | 3'-Deoxy-3'-[4-(2-methyl-2-propanyl)-1H-1,2,3-triazol-1-yl]thymidine | 0.61 | 46.01 x |
| 10 µmol/L | N-[4-(5-Methyl-2,4-dioxo-3H-pyrimidin-1-yl)butyl]-9H-fluorene-9-carboxamide | 0.58 | 43.30 x |

EXAMPLE 9—TREATMENT OF MUCOVISCIDOSIS

To determine the effects on the concentration of deletion mutant ΔF508 CFTR functionally integrated into the membrane, the mucoviscidosis cell line CCD-186Sk (ATCC® CRL-1563™) was used.

The mucoviscidosis cell line CCD-186Sk is a homozygous carrier of the ΔF508 mutation, to which the CFTR gene relates. The deletion of the phenylalanine at position 508 of the CFTR gene is typical of this disease and affects over 70% of patients. Because of this deletion, the CFTR protein that forms is not folded entirely correctly and is therefore supplied to the cellular degradation processes and not—like the healthy protein—transported to the cell membrane and incorporated there as a transmembrane protein. HSP27 plays a crucial role in isolating the delta F508 CFTR protein for degradation. The experiments serve to prove the hypothesis that delta F508 CFTR protein which is not isolated and degraded immediately upon its formation is transported to the cell membrane where, as a functioning transmembrane protein, it regulates the transport of water and salt through the plasma membrane of the cells.

For this purpose, the CCD-186Sk cells are seeded at a density of 100,000 cells/ml and incubated with:
2-(3-trichlorovinylphenylamino)-1,9-dihydropurin-6-one
2-(4-butylphenylamino)-9-(2-hydroxyethoxymethyl)-1,9-dihydropurin-6-one
2-(3-hydroxymethyl-phenylamino)-3,7-dihydropurin-6-one as representatives of the purine derivatives in the respective concentration. Every 24 hours, cells are harvested and tests are performed to see whether the treated cells present more CFTR at the cell surface than untreated cells. To detect the CFTR protein at the cell surface, an antibody is used which specifically labels the extracellular "loop" (amino acids 103-117) of the CFTR protein. This antibody is labelled with the fluorescent dye FITC and detected by flow cytometry.

EXAMPLE 10—BIO-LAYER INTERFEROMETRY

For measurements by bio-layer interferometry, biotinylated HSP27 protein was first bound to Super-Streptavidin sensors (SSA, Fortebio). The loaded sensors were then incubated ("quenched") with biocytin. As reference, unloaded SSA sensors were incubated with biocytin. In the case of a specific binding to HSP27 of the analyte to be measured, the loaded HSP27 sensor generates a stronger signal (response) than the concurrent reference sensor. After the "baseline" has been established by incubation with the reaction buffer (PBST 0.1% Tween 20 plus 3% DMSO), first the association and then the dissociation of the respective analyte is measured in real time. The analytes were measured in increasing concentrations in each case: 1.23-3.7-11.11-33.33-100-300 µM/l.

Results:

| Substance | Dissociation constant $K_D$ [µM] |
|---|---|
| Chlorpromazine | 770 |
| Acepromazine | 72 |
| 5-Phenyl-2'-deoxyuridine | 60 |
| 2-(3-Hydroxymethylphenylamino)-3,7-dihydropurin-6-one | 710 |

-continued

| Substance | Dissociation constant $K_D$ [µM] |
|---|---|
| 2-(4-Butylphenylamino)-9-(2-hydroxyethoxymethyl)-1,9-dihydropurin-6-one | 15 |
| 9H-Xanthene-9-carboxylic acid [4-(5-methyl-2,4-dioxo-3,4-dihydro-2H-pyrimidin-1-yl)-but-2-enyl]amide | 267 |
| 2-Biphenyl-4-yl-N-[4-(5-methyl-2,4-dioxo-3,4-dihydro-2H-pyrimidin-1-yl)-but-2-enyl]acetamide | 424 |

EXAMPLE 11—INHIBITION OF THE DEVELOPMENT OF RESISTANCE OF THE TUMOUR CELL LINE RPMI-8226 BY ACEPROMAZINE

The cell line RPMI-8226 (DMSZ 402) is a "multiple myeloma" cell line and was chosen because bortezomib is employed as a standard therapy for multiple myeloma. RPMI-8226 cells respond to bortezomib, express HSP27 and develop resistance to Velcade.

RPMI-8226 cells were seeded at a cell count of 100,000 cells/ml in each case and regularly passaged. FIG. 4a shows that, as a result of the treatment with 0.75 µmol/L acepromazine, the development of resistance to the cytostatic agent bortezomib was significantly inhibited and only 30,000 living cells per ml medium could be detected at the end of the experiment. In contrast, for RPMI 8226 cells that were treated with 30 µmol/L BVDU, a final cell count of 160,000 cells/ml was detected whereas the final cell count for the culture without the addition of an HSP27 inhibitor amounted to 350,000 cells/ml. As a control, RPMI 8226 cells were treated with the respective test substances alone, FIG. 4b. At the same dosage, the test substances alone do not affect cell growth, since HSP27 is not needed in a large quantity by the cancer cells without the pressure from the cytostatic agent.

EXAMPLE 12—INHIBITION OF THE DEVELOPMENT OF RESISTANCE OF THE TUMOUR CELL LINE RPMI-8226 BY CHLORPROMAZINE

RPMI-8226 cells were seeded with a cell count of 100,000 cells/ml in each case and regularly passaged. FIG. 5a shows that, as a result of the treatment with 0.5 µmol/L chlorpromazine, the development of resistance to the cytostatic agent bortezomib was significantly inhibited and only 70,000 living cells per ml medium could be detected at the end of the experiment. In contrast, for RPMI 8226 cells that were treated with 30 µmol/L BVDU, a final cell count of 160,000 cells/ml was detected whereas the final cell count in the culture without the addition of an HSP27 inhibitor amounted to 350,000 cells/ml. As a control, RPMI 8226 cells were treated with the respective test substances alone, FIG. 5b. At the same dosage, the test substances alone do not affect cell growth.

EXAMPLE 13—INHIBITION OF THE DEVELOPMENT OF RESISTANCE OF THE TUMOUR CELL LINE RPMI-8226 BY 2-(4-BUTYLPHENYLAMINO)-9-(2-HYDROXYETHOXYMETHYL)-1,9-DIHYDROPURIN-6-ONE

RPMI-8226 cells were seeded with a cell count of 100,000 cells/ml in each case and regularly passaged. FIG. 6a shows that, as a result of the treatment with 1 µM/L 2-(4-butylphenylamino)-9-(2-hydroxyethoxymethyl)-1,9-dihydropurin-6-one, the development of resistance to the cytostatic agent bortezomib was significantly inhibited. At the end of the experiment, 240,000 living cells per ml medium could be detected. For the treatment with 30 µM/L BVDU, a final cell count of 290,000 cells/ml was detected whereas the final cell count in the culture without the addition of an HSP27 inhibitor amounted to 950,000 cells/ml. As a control, RPMI 8226 cells were treated with the respective test substances alone, FIG. 6b. At the same dosage, the test substances alone do not affect cell growth.

EXAMPLE 14—INHIBITION OF THE DEVELOPMENT OF RESISTANCE OF THE TUMOUR CELL LINE RPMI-8226 BY 2-(3-TRICHLOROVINYLPHENYLAMINO)-1,9-DIHYDROPURIN-6-ONE

RPMI-8226 cells were seeded with a cell count of 100,000 cells/ml in each case and regularly passaged. FIG. 7a shows that, as a result of the treatment with 1 µmol/L 2-(3-trichlorovinylphenylamino)-1,9-dihydropurin-6-one, the development of resistance to the cytostatic agent bortezomib was significantly inhibited. At the end of the experiment, 270,000 living cells per ml medium could be detected. For the treatment with 30 µmol/L BVDU, a final cell count of 290,000 cells/ml was detected whereas the final cell count in the culture without the addition of an HSP27 inhibitor amounted to 950,000 cells/ml. As a control, RPMI 8226 cells were treated with the respective test substances alone, FIG. 7b. At the same dosage, the test substances alone do not affect cell growth.

EXAMPLE 15—INHIBITION OF THE DEVELOPMENT OF RESISTANCE OF THE TUMOUR CELL LINE RPMI-8226 BY 9H-XANTHENE-9-CARBOXYLIC ACID[4-(5-METHYL-2,4-DIOXO-3,4-DIHYDRO-2H-PYRIMIDIN-1-YL)-BUT-2-ENYL]AMIDE

RPMI-8226 cells were seeded with a cell count of 100,000 cells/ml in each case and regularly passaged. FIG. 8a shows that, as a result of the treatment with 1 µmol/L 9H-xanthene-9-carboxylic acid[4-(5-methyl-2,4-dioxo-3,4-dihydro-2H-pyrimidin-1-yl)-but-2-enyl]amide, the development of resistance to the cytostatic agent bortezomib was significantly inhibited. At the end of the experiment, 290,000 living cells per ml medium could be detected. For the treatment with 30 µmol/L BVDU, a final cell count of 340,000 cells/ml was detected whereas the final cell count in the culture without the addition of an HSP27 inhibitor amounted to 510,000 cells/ml. As a control, RPMI 8226 cells were treated with the respective test substances alone, FIG. 8b. At the same dosage, the test substances alone do not affect cell growth.

EXAMPLE 16—INHIBITION OF THE DEVELOPMENT OF RESISTANCE OF THE TUMOUR CELL LINE RPMI-8226 BY 2-BIPHENYL-4-YL-N[4-(5-METHYL-2,4-DIOXO-3,4-DIHYDRO-2H-PYRIMIDIN-1-YL)-BUT-2-ENYL]-ACETAMIDE

RPMI-8226 cells were seeded with a cell count of 100,000 cells/ml in each case and regularly passaged. FIG. 9a shows that, as a result of the treatment with 1 µmol/L 2-biphenyl-4-yl-N-[4-(5-methyl-2,4-dioxo-3,4-dihydro-2H- pyrimidin-1-yl)-but-2-enyl]-acetamide, the development of resistance to the cytostatic agent bortezomib was significantly inhibited. At the end of the experiment, 380,000 living cells per ml medium could be detected. For the treatment with 30 µmol/L BVDU, a final cell count of 340,000 cells/ml was detected whereas the final cell count in the culture without the addition of an HSP27 inhibitor amounted to 510,000 cells/ml. As a control, RPMI 8226 cells were treated with the respective test substances alone, FIG. 9b. At the same dosage, the test substances alone do not affect cell growth.

EXAMPLE 17—INHIBITION OF THE DEVELOPMENT OF RESISTANCE OF THE TUMOUR CELL LINE U-937 BY ACEPROMAZINE

The cell line U-937 is a histiocytic lymphoma (DSMZ ACC 5). This cell line also responds to treatment with bortezomib, expresses HSP27 and develops resistance to bortezomib. Bortezomib is not the standard therapy for this lymphoma, but is being discussed as a possible therapeutic agent.

U-937 cells were seeded with a cell count of 100,000 cells/ml in each case and regularly passaged. FIG. 10a shows that, as a result of the treatment with 0.75 µmol/L acepromazine, the development of resistance to the cytostatic agent bortezomib was significantly inhibited. At the end of the experiment, 70,000 living cells per ml medium could be detected. For the treatment with 30 µmol/L BVDU, a final cell count of 250,000 cells/ml was detected whereas the final cell count in the culture without the addition of an HSP27 inhibitor amounted to 450,000 cells/ml. As a control, U-937 cells were treated with the respective test substances alone, FIG. 10b. At the same dosage, the test substances alone do not affect cell growth.

EXAMPLE 18—INHIBITION OF THE DEVELOPMENT OF RESISTANCE OF THE TUMOUR CELL LINE U-937 BY 2-(4-BUTYLPHENYLAMINO)-9-(2-HYDROXYETHOXYMETHYL)-1,9-DIHYDROPURIN-6-ONE

U-937 cells were seeded with a cell count of 100,000 cells/ml in each case and regularly passaged. FIG. 11a shows that, as a result of the treatment with 0.75 µmol/L 2-(4-butyl-phenylamino)-9-(2-hydroxyethoxymethyl)-1,9-dihydropurin-6-one, the development of resistance to the cytostatic agent bortezomib was significantly inhibited. At the end of the experiment, 30,000 living cells per ml medium could be detected. For the treatment with 30 µmol/L BVDU, a final cell count of 250,000 cells/ml was detected whereas the final cell count in the culture without the addition of an HSP27 inhibitor amounted to 450,000 cells/ml. As a control, U-937 cells were treated with the respective test substances alone, FIG. 11b. At the same dosage, the test substances alone do not affect cell growth.

REFERENCES

Straume O, Shimamura T, Lampa M J, Carretero J, Øyan A M, Jia D, Borgman C L, Soucheray M, Downing S R, Short S M, Kang S Y, Wang S, Chen L, Collett K, Bachmann I, Wong K K, Shapiro G I, Kalland K H, Folkman J, Watnick R S, Akslen L A, Naumov G N. (2012) Suppression of heat shock protein 27 induces long-term dormancy in human breast cancer. Proc Natl Acad Sci USA. 2012 May 29; 109(22):8699-704.

Jakob U, Gaestel M, Engel K, and Buchner J. (1993) Small Heat Shock Proteins Are Molecular Chaperones. J Biol Chem 268(3): 1517-1520.

Muckenschnabel I, Falchetto R, Mayr L M, Filipuzzi I. (2004) SpeedScreen: label-free liquid chromatography-mass spectrometry-based high-throughput screening for the discovery of orphan protein ligands. Anal Biochem. 2004 Jan. 15; 324(2):241-9.

Chauhan D, Li G, Auclair D, Hideshima T, Podar K, Mitsiades N, Mitsiades C, Chen L B, Munshi N, Saxena S, Anderson K C. (2004) 2-Methoxyestardiol and bortezomib/proteasome-inhibitor overcome dexamethasone-resistance in multiple myeloma cells by modulating Heat Shock Protein-27. Apoptosis. 2004 March; 9(2): 149-55.

The invention claimed is:
1. A method for treating cancer comprising administering a pharmaceutically effective amount of a thymine derivative to a patient having cancer who is undergoing chemotherapy, radiotherapy and/or cancer immunotherapy,
wherein the thymine derivative is a thymine derivative of general formula (VI) and/or of general formula (VI')

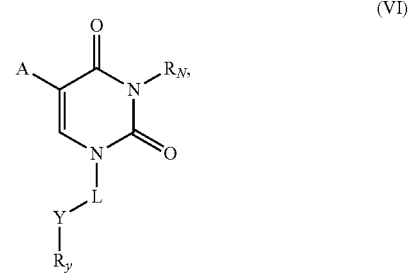

(VI)

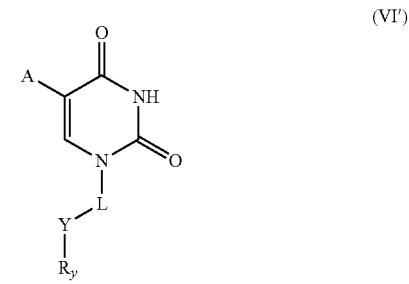

(VI')

wherein:
the substituent A is —H, halogen, —CH$_3$, an alkynyl residue, phenyl or a thiophene residue,
the linker L is an optionally substituted C1 to C6 alkyl residue, an optionally substituted phenyl, benzyl or pyridine residue,

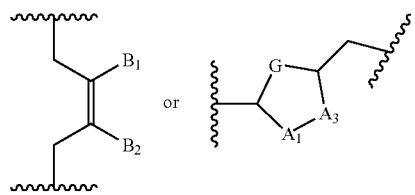

for thymine derivative of general formula (VI) and L is an optionally substituted C1 to C6 alkyl residue, an optionally substituted phenyl, benzyl or pyridine residue, or

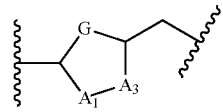

for thymine derivative of general formula (VI')
wherein
the substituents $B_1$ and $B_2$ independently of one another are —H, —$CH_3$, —$CF_3$, —F or —Cl,
$A_1$ is —$CH_2$—, —CHOR, —CHF— or —CHOC(=O)R,
$A_3$ is —$CH_2$—, —CHOR, —CHF—, —CHOC(=O)R or —CHK—, wherein K is an optionally substituted five-membered ring nitrogen heterocycle,
G is —$CH_2$—, —$CH_2O$— or —O—,
Y is S, NR, carboxyl, carbonyl or amide,
wherein R is H or a $C_1$ to $C_8$ alkyl residue,
the substituent $R_y$ is H, OH, —$CR_aR_bR_c$, an optionally substituted cyclic or polycyclic aryl residue or an optionally substituted oxygen or nitrogen heterocycle,
wherein $R_a$, $R_b$ and $R_c$ independently of one another are selected from H and cyclic residues,
the substituent $R_N$ is a benzoyl residue
wherein at least one of the residues $R_a$, $R_b$ and $R_c$ is H and at least one of the residues is a cyclic residue, selected from optionally substituted cyclic or polycyclic aryl residues and optionally substituted heterocycles.

2. The method for treating cancer according to claim 1, wherein $R_y$ is selected from H, general formula (III) or formula (IV)

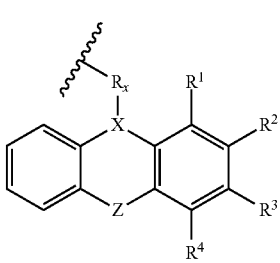

(III)

(IV)

wherein ⌇ is a covalent linkage to general formula (VI) or (VI'),
X is N or CH,
Z is a single bond, $CH_2$, O, C(=O), S or $NR_x$,
$R_x$ is an optionally substituted and/or branched $C_1$ to $C_4$ alkyl residue,
$R^1$, $R^2$, $R^3$ and $R^4$ each independently of one another are —H, -halogen, —$NO_2$, —CN, —$NR_2$ and —SR,
—OR, —COOR, —COR, —R, a $C_2$ to $C_4$ vinyl residue or an aryl residue, wherein R is H or $C_1$ to $C_8$ alkyl residue.

3. The method for treating cancer according to claim 2, wherein $R_y$ is selected from H and OH and $A_3$ is —CHK—, where K is an optionally substituted five-membered ring nitrogen heterocycle.

4. The method for treating cancer according to claim 2, wherein Z is O, C(=O) or S and X is N or CH.

5. The method for treating cancer according to claim 1, wherein Y is NR or an amide group, where R is H or $C_1$ to $C_8$ alkyl residue.

6. The method for treating cancer according to claim 2, wherein $R^1$, $R^3$ and optionally $R^4$ are H.

7. The method for treating cancer according to claim 2, wherein $R_y$ according to formula (IV), $R^1$ is H, $R^2$ and $R^3$ independently of one another are H or an optionally OH-functionalized $C_1$ to $C_5$ alkyl residue or an optionally substituted $C_2$ to $C_4$ vinyl residue.

8. The method for treating cancer according to claim 2, wherein $R_y$ according to formula (III), $R^1$, $R^3$ and $R^4$ are H and $R^2$ is H, -halogen, —COR or an optionally substituted phenyl residue, wherein this R in formula (III) is H or an optionally OH-functionalized $C_1$ to $C_5$ alkyl residue.

9. The method for treating cancer according to claim 1, wherein the thymine derivative is already administered before the start of the chemotherapy, radiotherapy and/or cancer immunotherapy and the administration of the thymine derivative is continued during these therapies.

10. The method for treating cancer according to claim 9, wherein the administration of the thymine derivative is started 15 min to 4 hours before the start of the chemotherapy, radiotherapy and/or cancer immunotherapy.

11. The method for treating cancer according to claim 1 comprising administering a pharmaceutically effective amount of a pharmaceutical formulation containing the thymine derivative to a patient having cancer who is undergoing chemotherapy, radiotherapy and/or cancer immunotherapy.

12. The method for treating cancer according to claim 1, wherein the thymine derivative is a thymine derivative of general formula (VI')

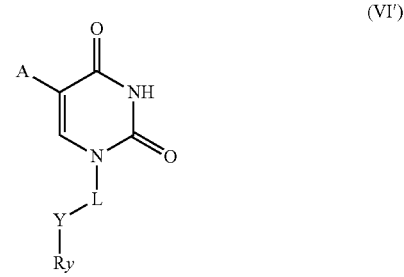

(VI')

wherein:
the substituent A is —H, halogen, —$CH_3$, —C=O, an alkynyl residue, phenyl or a thiophene residue,
the linker L is an optionally substituted $C_1$ to $C_6$ alkyl residue, an optionally substituted phenyl, benzyl or pyridine residue,

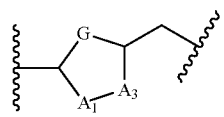

or
wherein
the substituents $B_1$ and $B_2$ independently of one another are —H, —CH$_3$, —CF$_3$, —F or —Cl,
$A_1$ is —CH$_2$—, —CHOR, —CHF— or —CHOC(=O)R,
$A_3$ is —CH$_2$—, —CHOR, —CHF—, —CHOC(=O)R or —CHK—, wherein K is an optionally substituted five-membered ring nitrogen heterocycle,
G is —CH$_2$—, —CH$_2$O— or —O—,
Y is S, NR, carboxyl, carbonyl or amide,
wherein R is H or a $C_1$ to $C_8$ alkyl residue,
the substituent $R_y$ is H, OH, —CR$_a$R$_b$R$_c$, an optionally substituted cyclic or polycyclic aryl residue or an optionally substituted oxygen or nitrogen heterocycle,
wherein $R_a$, $R_b$ and $R_c$ independently of one another are selected from H and cyclic residues,
wherein at least one of the residues $R_a$, $R_b$ and $R_c$ is H and at least one of the residues is a cyclic residue, selected from optionally substituted cyclic or polycyclic aryl residues and optionally substituted heterocycles.

\* \* \* \* \*